United States Patent
Drivas et al.

(10) Patent No.: US 10,155,794 B2
(45) Date of Patent: Dec. 18, 2018

(54) COMPOSITIONS AND METHODS FOR TREATMENT OF DISORDERS RELATED TO CEP290

(71) Applicant: The Trustees of the University of Pennsylvania, Philadelphia, PA (US)

(72) Inventors: Theodore G. Drivas, Philadelphia, PA (US); Jean Bennett, Bryn Mawr, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/904,447

(22) PCT Filed: Jul. 11, 2014

(86) PCT No.: PCT/US2014/046408
§ 371 (c)(1),
(2) Date: Jan. 12, 2016

(87) PCT Pub. No.: WO2015/009575
PCT Pub. Date: Jan. 22, 2015

(65) Prior Publication Data
US 2016/0185832 A1 Jun. 30, 2016

Related U.S. Application Data

(60) Provisional application No. 61/847,016, filed on Jul. 16, 2013.

(51) Int. Cl.
*C07K 14/47* (2006.01)
*C12Q 1/6883* (2018.01)
*A61K 38/00* (2006.01)
*A61K 48/00* (2006.01)

(52) U.S. Cl.
CPC ............ *C07K 14/47* (2013.01); *C12Q 1/6883* (2013.01); *A61K 38/00* (2013.01); *A61K 48/00* (2013.01); *C12Q 2600/156* (2013.01)

(58) Field of Classification Search
CPC .............................. C12Q 1/6883; C07K 14/47
See application file for complete search history.

(56) References Cited

U.S. PATENT DOCUMENTS

| | | |
|---|---|---|
| 2008/0044831 A1 | 2/2008 | Hidebrandt et al. |
| 2011/0117058 A1 | 5/2011 | Auricchio |

FOREIGN PATENT DOCUMENTS

| | | |
|---|---|---|
| WO | WO-2009/121536 | 10/2009 |
| WO | WO-2013/036105 | 3/2013 |

OTHER PUBLICATIONS

International Preliminary Report on Patentability dated Jan. 19, 2016 in corresponding International Patent Application No. PCT/US2014/046408, filed Jul. 11, 2014.
Uni Prot database Accession Nos, Q05BJ6-Q05BJ6_Human, CEP290 Protein, Nov. 2006.
Drivas, T.G. et al., Disruption of CEP290 Microtubule/Membrane-Binding Domains Causes Retinal Degeneration, The Journal of Clinical Investigation, Oct. 2013, 123(10): 4525-4539.
Drivas, T.G., Bridging the Gap: Defining the Molecular Mechanisms of CEP290 Disease Pathogenesis, Jan. 2013, Abstract only.
Drivas, T.G. et al., International Symposium on Retinal Degeneration, presented as poster on Jul. 16, 2012, no publication of abstract.
Baye, L.M. et al., The N-Terminal Region of Centrosomal Protein 290 (CEP290) Restores Vision in a Zebrafish Model of Human Blindness, Human Molecular Genetics, Jan. 2011, 20(8): 1467-1477.
Cideciyan, A.V. et al., Cone Photoreceptors Are the Main Targets for Gene Therapy of NPHP5 (IQCB1) or NPHP6 (CEP290) Blindness: Generation of an All-Cone Nphp6 Hypomorph Mouse that Mimics the Human Retinal Ciliopathy, Human Molecular Genetics, Jan. 2011, 20(7): 1411-1423.
International Search Report dated Dec. 17, 2014 in corresponding International Patent Application No. PCT/US2014/046408, filed Jul. 11, 2014.
Written Opinion dated Dec. 17, 2014 in corresponding International Patent Application No. PCT/US2014/046408, filed Jul. 11, 2014.
Brancati, F. et al., CEP290 mutations are frequently identified in the oculo-renal form of Joubert syndrome-related disorders, The American Journal of Human Genetics, Jul. 2007, 81(1):104-113.
Coppieters, F. et al., CEP290, a gene with many faces: mutation overview and presentation of CEP290base, Human Mutation, Aug. 2010, 31(10):1097-1108.
Craige, B. et al., CEP290 tethers flagellar transition zone microtubules to the membrane and regulates flagellar protein content, The Journal of Cell Biology, Sep. 2010, 190(5):927-940.
Kim, J. et al., CEP290 interacts with the centriolar satellite component PCM-1 and is required for Rab8 localization to the primary cilium, Human Molecular Genetics, Sep. 2008, 17(23):3796-3805.
Moradi, P. et al., Focus on molecules: centrosomal protein 290 (CEP290), Experimental Eye Research, May 2011, 92(5):316-7.
Perrault, E. et al. Spectrum of NPHP6/CEP290 mutations in Leber congenital amaurosis and delineation of the associated phenotype, Human Mutation, Mar. 2007, 28(4):416 (10 pages).
Valente, E. M et al., Mutations in CEP290, which encodes a centrosomal protein, cause pleiotropic forms of Joubert syndrome, Nature Genetics, May 2006, 38(6):623-625.
Baala, L. et al, Pleiotropic effects of CEP290 (NPHP6) mutations extend to Meckel syndrome, The American Journal of Human Genetics, Jul. 2007. 81(1):170-179.

(Continued)

*Primary Examiner* — Antonio Galisteo Gonzale
(74) *Attorney, Agent, or Firm* — Howson & Howson LLP

(57) ABSTRACT

Compositions are provided that comprise a recombinant vector carrying a nucleic acid sequence encoding a fragment of CEP290 lacking all or part of its N-terminal and C-terminal inhibitory regions, under the control of regulatory sequences which express the product of said gene in a selected cell of a mammalian subject, and a pharmaceutically acceptable carrier. These and other compositions are disclosed with are useful in methods for treating a mammalian subject having a disease associated with a CEP290 mutation, such as Lebers Congenital Amaurosis.

6 Claims, 30 Drawing Sheets
Specification includes a Sequence Listing.

(56) References Cited

OTHER PUBLICATIONS

Barral, D. C. et al., Arl13b regulates endocytic recycling traffic, PNAS, Dec. 2012, 109(52):21354-21359.

Berbari, N. F. et al., Bardet-Biedl syndrome proteins are required for the localization of G protein-coupled receptors to primary cilia, PNAS, Mar. 2008, 105(11):4242-4246.

Cevik, S. et al., Joubert syndrome Arl13b functions at ciliary membranes and stabilizes protein transport in Caenorhabditis elegans, The Journal of Cell Biology, Mar. 2010, 188(6):953-969.

Chang, B et al., In-frame deletion in a novel centrosomal/ciliary protein CEP290/NPHP6 perturbs its interaction with RPGR and results in early-onset retinal degeneration in the rd16 mouse, Human Molecular Genetics, Jun. 2006, 15(11):1847-1857.

D'Angelo A. and Franco, B., The dynamic cilium in human diseases, Pathogenetics, May 2009, 2(1):3.

D'Angiolella, V. et al., $SCF^{(Cyclin\ F)}$ controls centrosome homeostasis and mitotic fidelity through CP110 degradation, Nature, Jul. 2010, 466(7302):138-142.

Davenport, J. R. et al., Disruption of intraflagellar transport in adult mice leads to obesity and slow onset cystic kidney disease, Current Biology, Sep. 2007, 17(18):1586-1594.

Gilula, N. B. and Satir, P., The ciliary necklace. A ciliary membrane specialization, The Journal of Cell Biology, May 1972, 53(2):494-509.

Goetz, S. C. et al., The spinocerebellar ataxia-associated gene Tau tubulin kinase 2 controls the initiation of ciliogenesis, Cell, Nov. 2012,151(4):847-858.

Gorden, N. T. et al., CC2D2A is mutated in Joubert syndrome and interacts with the ciliopathy associated basal body protein CEP290, The American Journal of Human Genetics, Nov. 2008, 83(5):559-571.

Han, Y-G. et al., Dual and opposing roles of primary cilia in medulloblastoma development, Nature Medicine, Aug. 2009, 15(9):1062-1065.

Helou, J. et al., Mutation analysis of NPHP6/CEP290 in patients with Joubert syndrome and Senior-Løken syndrome, Journal of Medical Genetics, Oct. 2007, 44(10):657-663.

Hu, Q. and Nelson, W. J., Ciliary diffusion barrier: the gatekeeper for the primary cilium compartment, Cytoskeleton (Hoboken), Jun. 2011, 68(6):313-324.

Kee, H. L. et al., A size-exclusion permeability barrier and nucleoporins characterize a ciliary pore complex that regulates transport into cilia, Nature Cell Biology, Mar. 2012, 14(4):431-437.

Kikkawa, M. et al., 15 A resolution model of the monomeric kinesin motor, KIF1A, Cell, Jan. 2000, 100(2):241-252.

Kobayashi, T. and Dynlacht, B. D., Regulating the transition from centriole to basal body, The Journal of Cell Biology, May 2011, 193(3):435-444.

Lancaster, M. A. et al., Defective Wnt-dependent cerebellar midline fusion in a mouse model of Joubert syndrome, Nature Medicine, Jun. 2011, 17(6):726-731.

Li, Y. et al., The small GTPases ARLto13 and ARLto3 coordinate intraflagellar transport and ciliogenesis, The Journal of Cell Biology, Jun. 2010, 189(6):1039-1051.

Moen, R. J. et al., Characterization of a myosin VII MyTH/FERM domain, Journal of Molecular Biology, Oct. 2011, 413(1):17-23.

Mu, F. T. et al., EEA1, an early endosome-associated protein. EEA1 is a conserved alpha-helical peripheral membrane protein flanked by cysteine "fingers" and contains a calmodulin-binding IQ motif, The Journal of Biological Chemistry, Jun. 1995, 270(22):13503-13511.

Schäfer, T. et al., Genetic and physical interaction between the NPHP5 and NPHP6 gene products, Human Molecular Genetics, Aug. 2008, 17(23):3655-3662.

Seaman, M. N. et al., Cytosolic and membrane-associated proteins involved in the recruitment of AP-1 adaptors onto the trans-Golgi network, The Journal of Biological Chemistry, Oct. 1996, 271(41):25446-25451.

Smith, W. J. et al., Structure of the active N-terminal domain of Ezrin. Conformational and mobility changes identify keystone interactions, The Journal of Biological Chemistry, Feb. 2003, 278(7):4949-4956.

Song, X. et al., A novel membrane-dependent on/off switch mechanism of talin FERM domain at sites of cell adhesion, Cell Research, Jun. 2012, 22(11):1533-1545.

Spektor. A. et al., Cep97 and CP110 suppress a cilia assembly program, Cell, Aug. 2007, 130(4):678-690.

Stowe, T. R. et al., The centriolar satellite proteins Cep72 and Cep290 interact and are required for recruitment of BBS proteins to the cilium, Molecular Biology of the Cell, Sep. 2012, 23(17):3322-3335.

Tsang, W. Y. et al., CP110 suppresses primary cilia formation through its interaction with CEP290, a protein deficient in human ciliary disease, Developmental Cell, Aug. 2008, 15(2):187-197.

Waters, A. M. and Beales, P. L., Ciliopathies: an expanding disease spectrum, Pediatric Nephrology, Jul. 2011, 26(7):1039-1056.

Williams, C. L. et al., MKS and NPHP modules cooperate to establish basal body/transition zone membrane associations and ciliary gate function during ciliogenesis, The Journal of Cell Biology, Mar. 2011, 192(6):1023-1041.

Wong, S. Y. et al., Primary cilia can both mediate and suppress Hedgehog pathway-dependent tumorigenesis, Nature Medicine, Sep. 2009, 15(9):1055-1061.

Alieva IB, et al. Experimental model for studying the primary cilia in tissue culture cells. Membr Cell Biol. 1999; 12(6):895-905.

Bennicelli JL, et al. 430. CEP290 Minigene Model of Common Splice Site Mutation in Leber Congenital Amaurosis. Neurologic & Ophthalmic Gene & Cell Therapy II. DOI: https://doi.org/10.1016/S1525-0016(16)36234-7. Molecular Therapy vol. 20,.Supplement 1, p. S167-S168, May 2012.

Boye, SE et al, The human rhodopsin kinase promoter in an AAV5 vector confers rod- and conespecific expression in the primate retina. 2012 Human Gene Ther., 23(10):1101-15 (Published online: Jul. 30, 2012).

Collin RW et al. Antisense Oligonucleotide (AON)-based Therapy for Cep290-associated LCA. ARVO Annual Meeting Abstract, Apr. 2011. Invest. Ophthalmol. Vis. Sci. 2011; 52(14):3324.

Collin RW et al. Antisense Oligonucleotide (AON)-based Therapy for Leber Congenital Amaurosis Caused by a Frequent Mutation in CEP290. Mol Ther Nucleic Acids. Mar. 27, 2012; 1:e14. doi: 10.1038/mtna.2012.3. (Published online Mar. 27, 2012).

Cornell RB, Taneva SG. Amphipathic helices as mediators of the membrane interaction of amphitropic proteins, and as modulators of bilayer physical properties. Curr Protein Pept Sci. 2006; 7(6):539-552 (Dec. 2006).

Den Hollander, AI, et al. Leber congenital amaurosis: genes, proteins and disease mechanisms. Prog Retin Eye Res. 2008; 27(4):391-419. (Epub Jun. 1, 2008.).

Drivas TG, Bennett J. CEP290 and the primary cilium. Adv Exp Med Biol. 2014; 801:519-25. doi: 10.1007/978-1-4614-3209-8_66. (First Online: Mar. 25, 2014).

Drivas TG, et al. Basal exon skipping and genetic pleiotropy: A predictive model of disease pathogenesis. Sci Transl Med. Jun. 10, 2015; 7(291):291ra97. doi: 10.1126/scitranslmed.aaa5370. (Jun. 2015).

Drivas, TG and Bennett, J., CEP290 Directly Anchors Microtubules to the Membrane and Its N- and C-Termini Inhibit Protein Function and Ciliogenesis. Abstract, American Society of Gene & Cell Therapy 16th Annual Meeting, May 15-May 18, 2013, Molecular Therapy vol. 21, Supplement 1, May 2013.

Drivas, Theodore George, "Bridging the Gap: Defining the Molecular Mechanisms of Cep290 Disease Pathogenesis" Publicly Accessible Penn Dissertations. 851. https://repository.upenn.edu/edissertations/851; full text first accessible to public by University of Pennsylvania Franklin Library Mar. 2014.

Garanto A, et al. In vitro and in vivo rescue of aberrant splicing in CEP290-associated LCA by antisense oligonucleotide delivery. Hum Mol Genet. Jun. 15, 2016; 25(12):2552-2563. Epub Apr. 22, 2016.

Gustke N, et al. Domains of tau protein and interactions with microtubules. Biochemistry. 1994; 33(32):9511-9522 (Aug. 1994).

(56) References Cited

OTHER PUBLICATIONS

Klee CB. Ca2+-dependent phospholipid- (and membrane-) binding proteins. Biochemistry. 1988; 27(18):6645-6653 (Sep. 1988).
Pedersen LB, Rosenbaum JL. Intraflagellar transport (IFT) role in ciliary assembly, resorption and signalling. Curr Top Dev Biol. Jan. 2008; 85:23-61.
Sayer JA et al. The centrosomal protein nephrocystin-6 is mutated in Joubert syndrome and activates transcription factor ATF4. Nat Genet. 2006;38(6):674-681. (Epub May 7, 2006.).
Weber KL, et al. A microtubule-binding myosin required for nuclear anchoring and spindle assembly. Nature. 2004; 431(7006): 325-329 (Sep. 2004).

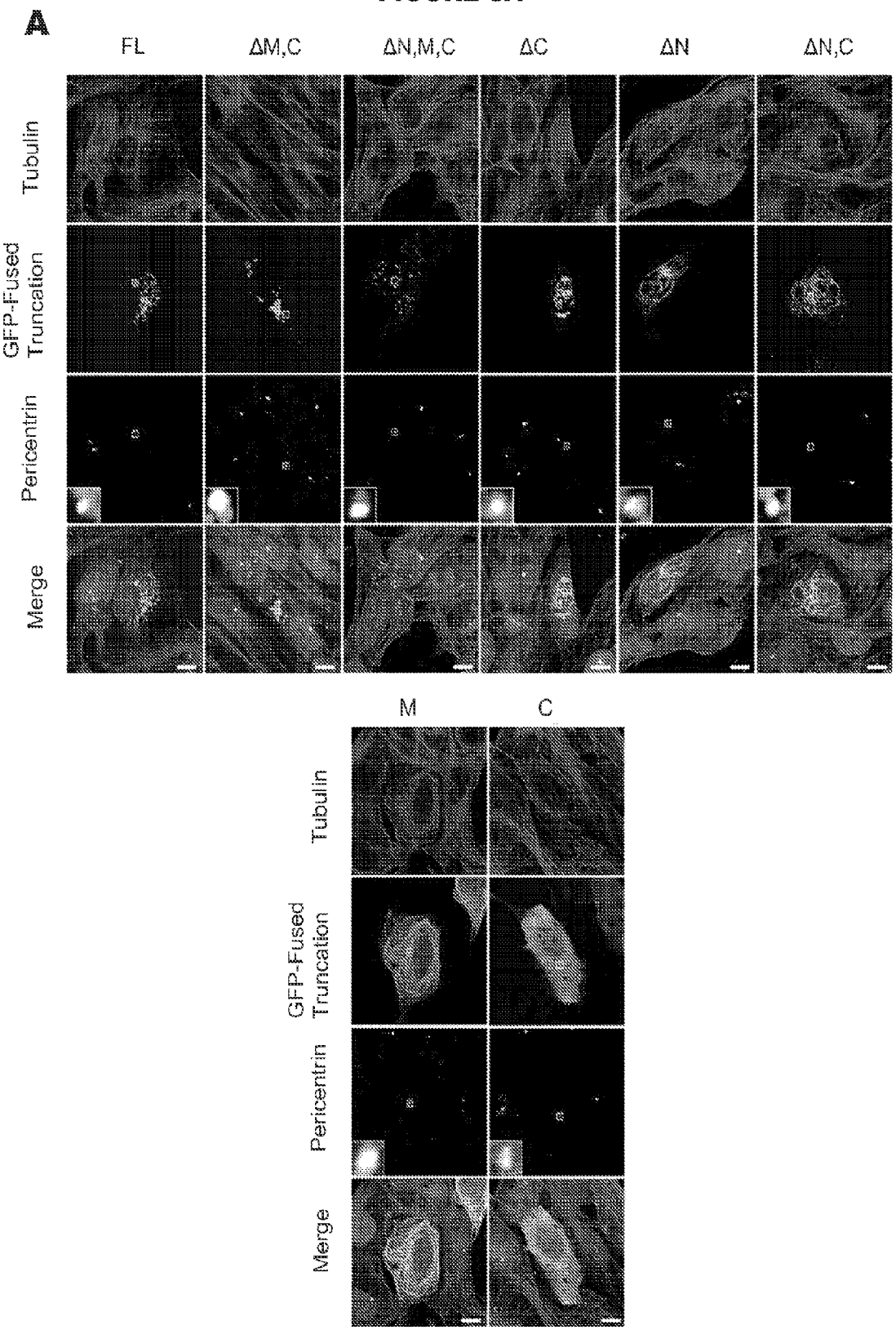

| Name | Schematic of truncated domains of CEP290 | Tubulin Colocalization |
|---|---|---|
| FL | | +/- |
| ΔM,C | | - |
| ΔN,M,C | | - |
| ΔC | | + |
| ΔN | | ++ |
| ΔN,C | | +++ |
| M | | +++ |
| C | | - |

Amino Acid: 1    580        1695  1966   2479

■ Homo/heterodimerization domain   ■ PCM1 and CP110 Binding   ■ CC2D2A binding
■ Rab8a binding                    ■ Myosin tail homology domain

FIGURES 5A-5B
A
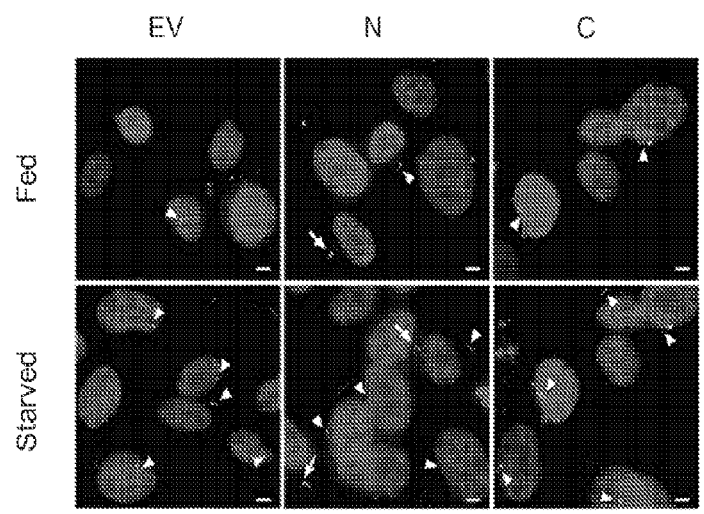
B
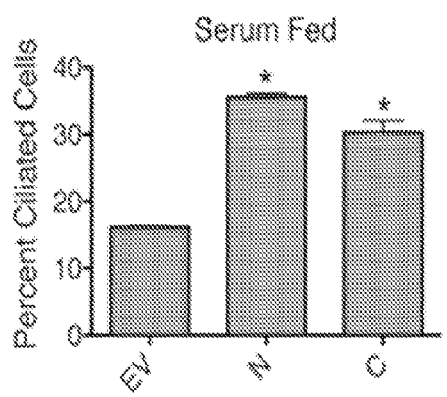 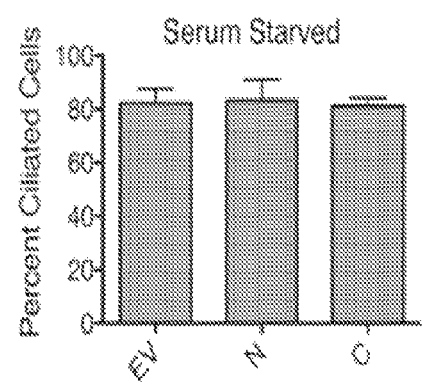

FIGURES 5E-5G
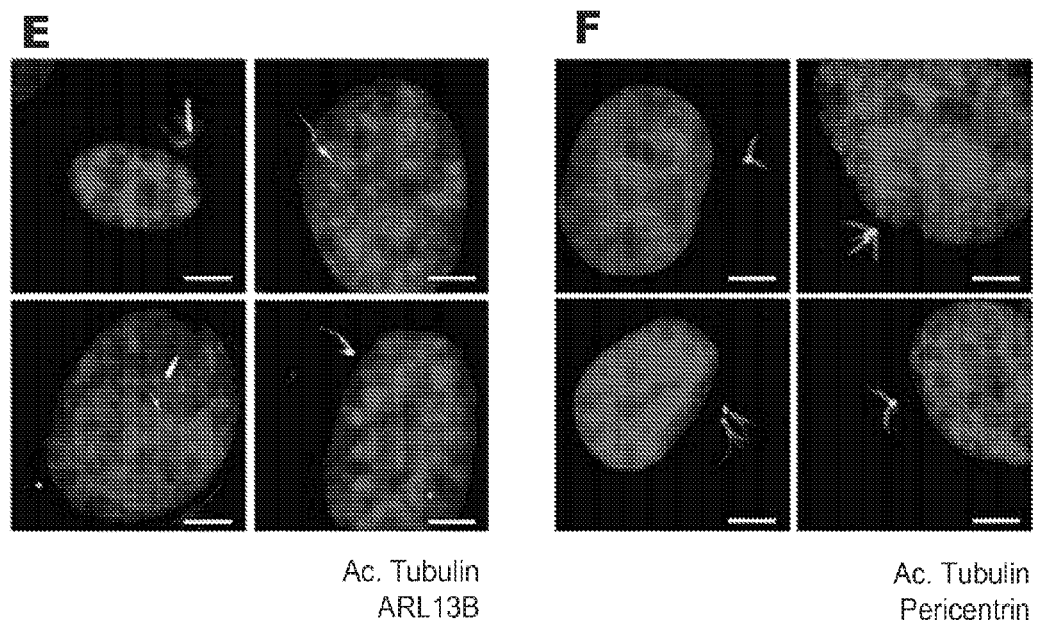
Ac. Tubulin
ARL13B
Ac. Tubulin
Pericentrin
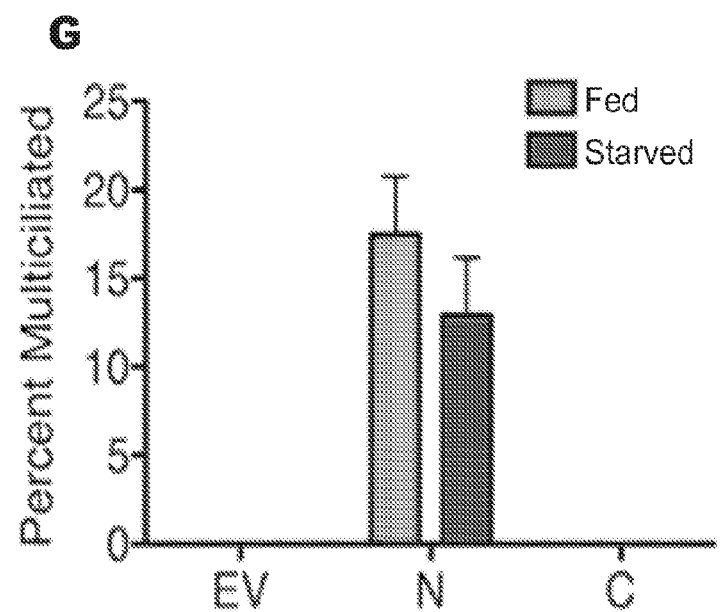

FIGURE 9A

SEQ ID NO: 1

```
atgccacctaatataaactggaaagaaataatgaaagttgacccagatgacctgcccgtcaagaagaac
tggcagataatttattgatttccttatccaagctggaagtaaatcagctaaaaagtgaaaagcaagaaa
tgtgatacacctttcagaattactcagtcactaatgaagatgaaagctcaagaagtggagctggctttg
gaagaagtagaaaaagctggagaagaacaagcaaaatttgaaaatcaattaaaaactaaagtaatgaaac
tggaaaatgaactggagatggctcagcagtctccaggtggacgacatactcggtttttacgtaatgaaat
ttgccaacttgaaaaacaattagaacaaaaagatagagaattggaggacatggaaaaggagttggagaaa
gagaagaaagttaatgagcaattggctcttcgaaatgaggaggcagaaaatgaaaacagcaaattaagaa
gagagaacaaacgtctaaagaaaaagaatgaacaactttgtcagcatattattgactaccagaaacaaat
agattcacagaaagaaacacttttatcaagaacaggggaagacagtgactaccgatcacagttgtctaaa
aaaaactatgagcttatccaatatcttgatgaaattcagactttaacagaagctaatgagaaaattgaag
ttcagaatcaagaaatgagaaaaaatttagaacagtctgtacagcaaatggagaagatgactgatgaata
taatagaatgaaagctattgtgcatcagacagataatgtaatagatcagttaaaaaagaaaacgatcat
tatcaacttcaagtgcaggagcttacagatcttctgaaatcaaaaaatgaagaagatgatccaattatgg
tagctgtcaatgcaaaagtagaagaatggaagctaatttgtcttctaaagatgatgaaattattgagta
tcagcaaatgttacataacctaagggagaaacttaagaatgctcagcttgatgctgataaaagtaatgtt
atggctctacagcagggtatacaggaacgagacagtcaaattaacatgctcaccgaacaagtagaacaat
atacaaaagaaatggaaaagaatacttgtattattgaagatttgaaaaatgagctccaaagaaacaaagg
tgcttcaacccttctcaacagactcatatgaaaattcagtcaacgttagacattttaaaagagaaaact
aaagaggctgagagaacagctgaactggctgacgctgatgctagcgaaaaggataaagaattagttgagg
ctctgaagaggttaaaagattatgaatcgggactatatggtttacaagatgctgtcgttgaaataaagaa
ttgtaaaaaccaaattaaaataagagatcgagagattgaaatattaacaaaggaaatcaataaacttgaa
ttgaagatcagtgatttccttgatgaaaatgacgcacttagagacgtgtgggccttgaaccaaagacaa
tgattgatttaactgaatttagaaatagcaaacacttaaaacagcagcagtacagagctgaaaaccagat
tcttttgaaagagattgaaagtctagaggaagaacgacttgatctgaaaaaaaaaattcgtcaaatggct
caagaaagaggaaaaagaagtgcaacttcaggattaaccactgacgacctgaacctaactgaaaacattt
ctcaaggagatagaataagtgaaagaaaattgcatttattgagcctcaaaaatatgagtgaagcacaatc
aaagaatgaatttctttcaagagaactaattgaaaagaaagagatttagaaaggagtaggacagtgata
gccaaatttcagaataaattaaaagaattagttgaagaaaataagcaacttgaagaaggtatgaaagaaa
tattgcaagcaattaaggaaatgcagaaagatcctgatgttaaacgaggagaaacatctctaattatccc
tagccttgaaagactagttaatgctatagaatcaaagaatgcagaaggaatctttgatgcgagtctgcat
ttgaaagcccaagttgatcagcttaccggaagaaatgaagaattaagacaggagctcagggaatctcgga
aagaggctataaattattcacagcagttggcaaaagctaatttaaagatagaccatcttgaaaaagaaac
tagtcttttacgacaatcagaaggatcgaatgttgtttttaaagcaattgacttacctgatgggatagca
ccatctagtgccagtatcattaattctcagaatgaatatttaatacatttgttacaggaactagaaaata
aagaaaaaaagttaaagaatttagaagattctcttgaagattacaacagaaaatttgctgtaattcgtca
tcaacaaagtttgttgtataaagaatacctaactgaaaaggagacctggaaaacagaatctaaaacaata
aaagaggaaaagagaaaacttgaggatcaagtccaacaagatgctataaaagtaaaagaatataataatt
tgctcaatgctcttcagatggattcggatgaaatgaaaaaaatacttgcagaaaatagtaggaaaattac
tgttttgcaagtgaatgaaaaatcacttataacgcaatatacaaccttagtagaattggagcgacaactt
agaaaagaaaatgagaagcaaaagaatgaattcttgtcaatggacgctgaagtttgtgaaaaaattgggt
```

FIGURE 9A (cont'd)

```
gtttgcaaagatttaaggaaatggccattttcaagattgcagctctccaaaaagttgtagataatagtgt
ttctttgtctgaactagaactggctaataaacagtacaatgaactgactgctaagtacagggacatcttg
caaaaagataatatgcttgttcaaagaacaagtaacttggaacacctggagtgtgaaaacatctccttaa
aagaacaagtggagtctataaataaagaactggagattaccaaggaaaaacttcacactattgaacaagc
ctgggaacaggaaactaaattaggtaatgaatctagcatggataaggcaagaaatcaataaccaacagt
gacattgtttccatttcaaaaaaataactatgctgcaaatgaaggaattaaatgaaaggcagcgggctg
aacattgtcaaaaatgtatgaacacttacggacttcgttaaagcaaatggaggaacgtaattttgaatt
ggaaaccaaatttgctgagcttaccaaaatcaatttcgatgcacagaaggtggaacagatgttaagagat
gaattagctgatagtgtgagcaaggcagtaagtgatgctgataggcaacggattctagaattagagaaga
atgaaatggaactaaaagttgaagtgtcaaaactgagagagatttctgatattgccagaagacaagttga
aattttgaatgcacaacaacaatctagggacaaggaagtagagtccctcagaatgcaactgctagactat
caggcacagtctgatgaaaagtcgctcattgccaagttgcaccaacataatgtctctcttcaactgagtg
aggctactgctcttggtaagttggagtcaattacatctaaactgcagaagatggaggcctacaacttgcg
cttagagcagaaacttgatgaaaagaacaggctctctattatgctcgtttggagggaagaaacagagca
aaacatctgcgccaaacaattcagtctctacgacgacagtttagtggagctttaccttggcacaacagg
aaaagttctccaaaacaatgattcaactacaaaatgacaaacttaagataatgcaagaaatgaaaaattc
tcaacaagaacatagaaatatggagaacaaaacattcgagatggaattaaaattaaagggcctggaagag
ttaataagcactttaaaggataccaaaggagcccaaaaggtaatcaactggcatatgaaaatagaagaac
ttcgtcttcaagaacttaaactaaatcgggaattagtcaaggataaagaagaaataaaatatttgaataa
cataatttctgaatatgaacgtacaatcagcagtcttgaagaagaaattgtgcaacagaacaagtttcat
gaagaaagacaaatggcctgggatcaaagagaagttcacctggaacgccaactagacattttgaccgtc
agcaaaatgaaatactaaatgcggcacaaaagtttgaagaagctacaggatcaatccctgaccctagttt
gcccttccaaatcaacttgagatcgctctaaggaaaattaaggagaacattcgaataattctagaaaca
cgggcaacttgcaaatcactagaagagaaactaaaacagaaagaatctgctttaaggttagcagaacaaa
atatactgtcaagagacaaagtaatcaatgaactgacggttcgattgcctgccactgcagaaagagaaaa
gctcatagctgagctaggcagaaaagagatggaaccaaaatctcaccacacattgaaaattgctcatcaa
accattgcaaacatgcaagcaaggttaaatcaaaaacaagaagtattaaagaagtatcaacgtcttctag
aaaaagccagagaggagcaaagagaaattgtgaagaaacatgaggaagaccttcatattcttcatcacag
attagaactacaggctgatagttcactaaataaattcaaacaaacggcttgggatttaatgaaacagtct
cccactccagttcctaccaacaagcattttattcgtctggctgagatggaacagacagtagcagaacaag
atgactctctttcctcactcttggtcaaactaaagaaagtatcacaagatttggagagacaaagagaaat
cactgaattaaaagtaaaagaatttgaaaatatcaaattacagcttcaagaaaaccatgaagatgaagtg
aaaaaagtaaaagcggaagtagaggatttaaagtatcttctggaccagtcacaaaaggagtcacagtgtt
taaaatctgaacttcaggctcaaaaagaagcaaattcaagagctccaacaactacaatgagaaatctagt
agaacggctaaagagccaattagccttgaaggagaaacaacagaaagcacttagtcgggcacttttagaa
ctccgggcagaaatgacagcagctgctgaagaacgtattatttctgcaacttctcaaaagaggcccatc
tcaatgttcaacaaatcgttgatcgacatactagagagctaaagacacaagttgaagatttaaatgaaaa
tcttttaaaattgaaagaagcacttaaaacaagtaaaaacagagaaaactcactaactgataatttgaat
gacttaaataatgaactgcaaaagaaacaaaaagcctataataaaatacttagagagaagaggaaattg
atcaagagaatgatgaactgaaaaggcaaattaaaagactaaccagtggattacagggcaaacccctgac
agataataaacaaagtctaattgaagaactccaaagcaaagttaaaaaactagagaaccaattagaggga
aaggtggaggaagtagacctaaaacctatgaaagaaaagaatgctaaagaagaattaattaggtgggaag
aaggtaaaaagtggcaagccaaaatagaaggaattccaaacaagttaaaagagaaagagggggaagtctt
```

FIGURE 9A (cont'd)

```
tactttaacaaagcagttgaatactttgaaggatcttttttgccaaagccgataaagagaaacttactttg
cagaggaaactaaaaacaactggcatgactgttgatcaggttttgggaatacgagctttggagtcagaaa
aagaattggaagaattaaaaaagagaaatcttgacttagaaaatgatatattgtatatgagggcccacca
agctcttcctcgagattctgttgtagaagatttacatttacaaaatagatacctccaagaaaaacttcat
gctttagaaaaacagttttcaaaggatacatattctaagccttcaatttcaggaatagagtcagatgatc
attgtcagagagaacaggagcttcagaaggaaaacttgaagttgtcatctgaaaatattgaactgaaatt
tcagcttgaacaagcaaataaagatttgccaagattaaagaatcaagtcagagatttgaaggaaatgtgt
gaatttcttaagaaagaaaaagcagaagttcagcggaaacttggccatgttagagggtctggtagaagtg
gaaagacaatcccagaactggaaaaaaccattggtttaatgaaaaaagtagttgaaaaagtccagagaga
aaatgaacagttgaaaaaagcatcaggaatattgactagtgaaaaaatggctaatattgagcaggaaaat
gaaaaattgaaggctgaattagaaaaacttaaagctcatcttgggcatcagttgagcatgcactatgaat
ccaagaccaaaggcacagaaaaaattattgctgaaaatgaaaggcttcgtaaagaacttaaaaaagaaac
tgatgctgcagagaaattacggatagcaaagaataatttagagatattaaatgagaagatgacagttcaa
ctagaagagactggtaagagattgcagtttgcagaaagcagaggtccacagcttgaaggtgctgacagta
agagctggaaatccattgtggttacaagaatgtatgaaaccaagttaaaagaattggaaactgatattgc
caaaaaaatcaaagcattactgaccttaaacagcttgtaaaagaagcaacagagagagaacaaaaagtt
aacaaatacaatgaagaccttgaacaacagattaagattcttaaacatgttcctgaaggtgctgagacag
agcaaggccttaaacgggagcttcaagttcttagattagctaatcatcagctggataaagagaaagcaga
attaatccatcagatagaagctaacaaggaccaaagtggagctgaaagcaccatacctgatgctgatcaa
ctaaaggaaaaaataaaagatctagagacacagctcaaaatgtcagatctagaaaagcagcatttgaagg
aggaaataaagaagctgaaaaaagaactggaaaattttgatccttcattttttgaagaaattgaagatct
taagtataattacaaggaagaagtgaagaagaatattctcttagaagagaaggtaaaaaaactttcagaa
caattgggagttgaattaactagccctgttgctgcttctgaagagtttgaagatgaagaagaaagtcctg
ttaatttccccatttac
```

FIGURE 9B

SEQ ID NO: 2 - Full Length naturally occurring Human CEP290 Protein Sequence

```
MPPNINWKEI MKVDPDDLPR QEELADNLLI SLSKVEVNEL KSEKQENVIH LFRITQSLMK
MKAQEVELAL EEVEKAGEEQ AKFENQLKTK VMKLENELEM AQQSAGGRDT RFLRNEICQL
EKQLEQKDRE LEDMEKELEK EKKVNEQLAL RNEEAENENS KLRRENKRLK KKNEQLCQDI
IDYQKQIDSQ KETLLSRRGE DSDYRSQLSK KNYELIQYLD EIQTLTEANE KIEVQNQEMR
KNLEESVQEM EKMTDEYNRM KAIVHQTDNV IDQLKKENDH YQLQVQELTD LLKSKNEEDD
PIMVAVNAKV EEWKLILSSK DDEIIEYQQM LHNLREKLKN AQLDADKSNV MALQQGIQER
DSQIKMLTEQ VEQYTKEMEK NTCIIEDLKN ELQRNKGAST LSQQTHMKIQ STLDILKEKT
KEAERTAELA EADAREKDKE LVEALKRLKD YESGVYGLED AVVEIKNCKN QIKIRDREIE
ILTKEINKLE LKISDFLDEN EALRERVGLE PKTMIDLTEF RNSKHLKQQQ YRAENQILLK
EIESLEEERL DLKKKIRQMA QERGKRSATS GLTTEDLNLT ENISQGDRIS ERKLDLLSLK
NMSEAQSKNE FLSRELIEKE RDLERSRTVI AKFQNKLKEL VEENKQLEEG MKEILQAIKE
MQKDFDVKGG ETSLIIPSLE RLVNAIESKN AEGIFDASLH LKAQVDQLTG RNEELRQELR
ESRKEAINYS QQLAKANLKI DHLEKETSLL RQSEGSNVVF KGIDLPDGIA PSSASIINSQ
NEYLIHLLQE LENKEKKLKN LEDSLEDYNR KFAVIRHQQS LLYKEYLSEK ETWKTESKTI
KEEKRKLEDQ VQQDAIKVKE YNNLLNALQM DSDEMKKILA ENSRKITVLQ VNEKSLIRQY
TTLVELERQL RKENEKQKNE LLSMEAEVCE KIGCLQRFKE MAIFKIAALQ KVVDNSVSLS
ELELANKQYN ELTAKYRDIL QKDNMLVQRT SNLEHLECEN ISLKEQVESI NKELEITKEK
LHTIEQAWEQ ETKLGNESSM DKAKKSITNS DIVSISKKIT MLEMKELNER QRAEHCQKMY
EHLRTSLKQM EERNFELETK FAELTKINLD AQKVEQMLRD ELADSVSKAV SDADRQRILE
LEKNEMELKV EVSKLREISD IARRQVEILN AQQQSRDKEV ESLRMQLLDY QAQSDEKSLI
AKLHQHNVSL QLSEATALGK LESITSKLQK MEAYNLRLEQ KLDEKEQALY YARLEGRNRA
KHLRQTIQSL RRQFSGALPL AQQEKFSKTM IQLQNDKLKI MQEMKNSQQE HRNMENKTLE
MELKLKGLEE LISTLKDTKG AQKVINWHMK IEELRLQELK LNRELVKDKE EIKYLNNIIS
EYERTISSLE EEIVQQNKFH EERQMAWDQR EVDLERQLDI FDRQQNEILN AAQKFEEATG
SIPDPSLPLP NQLEIALRKI KENIRIILET RATCKSLEEK LKEKESALRL AEQNILSRDK
VINELRLRLP ATAEREKLIA ELGRKEMEPK SHETLKIAHQ TIANMQARLN QKEEVLKKYQ
RLLEKAREEQ REIVKKHEED LHILHHRLEL QADSSLNKFK QTAWDLMKQS PTPVPTNKHF
IRLAEMEQTV AEQDDSLSSL LVKLKKVSQD LERQREITEL KVKEFENIKL QLQENHEDEV
KKVKAEVEDL KYLLDQSQKE SQCLKSELQA QKEANSRAPT TTMRNLVERL KSQLALKEKQ
QKALSRALLE LRAEMTAAAE ERIISATSQK EAHLNVQQIV DRHTRELKTQ VEDLNENLLK
LKEALKTSKN RENSLTDNLN DLNNELQKKQ KAYNKILREK EEIDQENDEL KRQIKRLTSG
LQGKPLTDNK QSLIEELQRK VKKLENQLEG KVEEVDLKPM KEKNAKEELI RWEEGKKWQA
KIEGIRNKLK EKEGEVFTLT KQLNTLKDLF AKADKEKLTL QRKLKTTGMT VDQVLGIRAL
ESEKELEELK KRNLDLENDI LYMRAHQALP RDSVVEDLHL QNPRYLQEKLH ALEKQFSKDT
YSKPSISGIE SDDHCQREQE LQKENLKLSS ENIELKFQLE QANKDLPRLK NQVRDLKEMC
EFLKKEKAEV QRKLGHVRGS GRSGKTIPEL EKTIGLMKKV VEKVQRENEQ LKKASGILTS
EKMANIEQEN EKLKAELEKL KAHLGHQLSM HYESKTKGTE KIIAENERLR KELKKETDAA
EKLRIAKNNL EILNEKMTVQ LEETGKRLQF AESRGPQLEG ADSKSWKSIV VTRMYETKLK
ELETDIAKKN QSITDLKQLV KEATEREQKV NKYNEDLEQQ IKILKHVPEG AETEQGLKRE
LQVLRLANHQ LDKEKAELIH QIEANKDQSG AESTIPDADQ LKEKIKDLET QLKMSDLEKQ
HLKEEIKKLK KELENFDPSF FEEIEDLKYN YKEEVKKNIL LEEKVKKLSE QLGVELTSPV
AASEEFEDEE ESPVNFPIY
```

FIGURE 10A

SEQ ID NO: 3 atgccccaaacatcaattggaaagagattatcaaggtagaccccgatgatcttcctagacaggaagagc
ttgctgataatcttttgatctccctcagtaaggtggaggtgaacgagctgaaatcagaaaagcaggagaa
tgttatacatctttttcgcatcacccagtctctcatgaagatgaaagcacaagaagtggaactcgcattg
gaagaggttgagaaagcgggcgaggagcaggctaagtttgaaaaccagctgaaaacgaaggttatgaagc
tggagaacgagctcgagatggcgcagcagtcaccggaggtagggatacaaggttttgagaaatgagat
atgtcagttggagaaacagcttgagcagaaagatcgggagttggaggacatggaaaggagctcgaaaaa
gaaaagaaagtgaatgagcagctcgccctgcgcaacgaagaagccgaaaacgaaacagtaagctgagaa
gggaaaacaaacggctgaaaagaagaacgagcagctctgtcaggatatcatagattaccagaaacagat
cgattcacaaaagaaactttgctctcacgaacgggagaagatagcgactatagatcacagctcagtaag
aagaactacgagctgattcagtacttggatgaaattcagaccctgacagaagccaatgagaaaatcgaag
tacagaaccaagaaatgcggaaaaacctcgagcagagcgtgcaagagatggagaagatgaccgacgaata
caaccggatgaaagctattgtacatcagactgacaacgtcatcgatcaattgaagaaagaaaacgaccac
taccaattgcaagttcaagagctgaccgatctcctcaaatccaaaaacgaggaggacgacccataatgg
tggccgtgaacgctaaagtcgaagagtggaaactgatcctctcctcaaggatgacgagattatcgaata
tcagcagatgctgcacaatctgcgcgagaagttgaagaatgcacagctcgacgccgacaaatctaatgta
atggccctgcagcagggaatccaagaaagggatagtcaaatcaaaatgcttactgagcaagtcgaacagt
acaccaaagagatggagaaaaacacttgatcattgaggacctcaagaacgaattgcagcgaaacaaggg
ggcttctacactcagtcagcaaactcatatgaaaatccagagcactctggacatcctcaaggagaaaaca
aaggaagccgagcgcacagccgaactggcagaagccgatgcacgcgagaaggacaaagagcttgtggagg
ctcttaagcggctcaaggactacgaatccgggctttacggactcgaggacgccgtcgtggaaatcaagaa
ctgcaagaaccagattaagattcgggacagagagatcgaaatcctgaccaaggaaatcaataagctggaa
ctcaagattagtgatttcctcgatgagaacgaagccctgcgggaacgcgtaggactggaacccaaaacaa
tgatcgatctgaccgaattccgcaattctaagcaccttaaacagcagcagtaccgagcggagaaccagat
tctgctgaaagaaattgagtcacttgaggaggagagacttgatcttaagaagaagattaggcaaatggct
caagaacggggaaaacggtccgcaacgagtggcctgactaccgaggatctgaatcttacggagaacataa
gccaaggcgacaggatttcagaacggaaattgcatttgcttagcctcaagaatatgagtgaagcccagag
caagaatgagtttctgtccagggaactgattgaaaagagcgggaccttgaacggagcagaacagtcatc
gccaagttccagaacaaactgaaagagctggtcgaggaaaacaagcagctggaggaaggcatgaaggaaa
ttctccaggcaatcaaggagatgcaaaaggacccagatgtcaaaggcggagaaacgtccctgattatcc
ctcactcgagcggctggtgaatgccattgaatctaagaacgcagagggtatctttgacgcttcactgcac
cttaaggcccaagtcgatcagctgacaggcagaaatgaggagcttcgccaggaactccgcgagtcccgca
agaagcaatcaactatagtcagcagctggcaaaagctaacctcaaaatcgaccatctcgaaaaagaaac
gtccctgctcagacagtccgagggcagcaatgttgtgttcaagggcatagatctcccggacggcattgcc
cccagtagtgcttccatcataaactcccaaaacgaatacttgatccatctgctgcaagagcttgagaaca
aggagaagaaacttaagaatttggaggacagcctcgaggactacaataggaagttcgctgtcatccggca
ccagcagagcttgttgtataaggaatatcttactgagaaggagacttggaaaacagagagtaaaacgata
aaggaagagaagcgcaaactggaggaccaggttcagcaggatgccattaaggtgaaagagtacaataacc
ttctgaatgcgttgcagatggacagcgacgagatgaagaaaatcttggctgagaattcccggaaaatcac
cgtgctccaagtcaatgagaagtccctcataacacagtacaccacactcgtcgaactggaaagacagctg
aggaaggagaacgaaaaacagaaaaacgagctgcttagcatggaggccgaagtatgcgagaagataggat
gtctgcaaaggttcaaagagatggccatattcaagatcgcggcactccagaaagtggtcgataactctgt

FIGURE 10A (cont'd)

```
gtctctcagcgagttggaactggccaataagcagtacaatgagctgacagccaagtatagagatattctc
caaaaggacaatatgttggtccagaggacttcaaatcttgagcacttggagtgtgagaacatttcactta
aagaacaagtagagtccatcaataaggagctgaaatcacaaaagaaaaactgcacacaatagaacaagc
atgggaacaggaaactaaactgggcaacgaaagcagcatggacaaggccaagaaatcaatcactaacagc
gacattgtgagtatttctaagaagatcactatgctggagatgaaagagttgaacgagaggcagagagccg
agcactgtcagaagatgtatgaacaccttagaacatccctcaaacagatggaggaaagaaacttcgagct
ggaaaccaagtttgctgagctgaccaagattaaccttgacgcccagaaggtggagcagatgctgcgcgat
gaactggccgacagtgtaagcaaggcggtcagcgacgcagaccgccagcggattttggagctggaaaaga
acgaaatggagctcaaagtcgaggtcagtaagcttcgcgaaatcagcgatatcgctaggcggcaggtgga
gattcttaatgccagcaacagtccgagataaagaggttgagtcactccggatgcaactcctcgattac
caggcccagagcgacgaaaagtcactcatcgcaaagttgcaccagcacaacgtttcccttcagctgtccg
aagccacagccttggggaaattggaatccattaccagcaagctgcagaaaatggaggcgtacaatctgcg
cctcgagcagaagctggacgagaaggagcaggccctgtattacgtcgcctggaaggacggaaccgagct
aagcatctgcggcagactattcagagcctgcggaggcaattcagcggagccctgcctctcgctcagcaag
agaagtttctaaaacaatgatacagctgcaaaatgataaactcaaaatcatgcaagagatgaagaactc
tcagcaggagcacagaaacatggagaacaagacactggagatggaactcaagttgaaagggctggaggag
ttgatttctacccttaaggatacaaaaggggcacaaaaggtcattaactggcatatgaagatagaggaac
tgagactgcaagaactcaaactgaatagagagttggtgaaggacaaagaagagatcaagtaccttaacaa
tatcatctcagaatacgagcggactatcagttcactggaggaggagattgttcagcagaacaaattccat
gaggaaaggcagatggcttgggatcagagagaagtggatttggagaggcagctggacatctttgatagac
aacagaatgagatcctcaacgcggcacagaaattcgaagaagcgacaggttcaatccccgatccatctct
tccactcccaaatcagcttgagattgctctgagaaagatcaaggaaaacatacggattatccttgagact
agagctacttgcaagagcctcgaagaaaaactgaaggagaaggagtctgcactgcggcttgcagagcaga
atatcctgtctcgggataaggttatcaacgaactgcgcctgaggcttcctgctaccgccgagagagagaa
actgattgctgaacttggacgaaaagaaatggaaccgaaatctcatcacacgctcaagattgcccaccag
acaatagccaatatgcaggccaggctgaatcagaaagaggaggtgctgaagaagtatcaacgcctgctgg
agaaagctaggaggagcagagagagattgtgaaaaagcacgaagaggacctccatatcctccatcatcg
gttggagcttcaggcagattcctccctgaacaagtttaagcagacagcctgggaccttatgaaacagtct
ccaacaccgtgccgactaacaagcatttcatccgcttggcggagatggaacagaccgtggccgagcagg
acgactcactgtcctcccttctggtaaagctgaagaaagtaagccaggacctgagcgacagagggagat
taccgagctgaaggtcaaggaattcgagaacatcaagctgcaactccaagagaaccacgaagatgaggtc
aagaaggtgaaggcagaagttgaggatttgaagtatctgctggatcagtcccagaaggagtcacagtgct
tgaaaagcgaactgcaggcacagaaggaagccaatagccgagcccctaccacgactatgagaaacttggt
ggaacggctcaaatcccagctcgccttgaaagagaagcagcagaaagcactgtcccgagcgttgcttgag
ctgcgagctgagatgacggcagcagccgaggagcgcatcatttctgctaccagccaaaaagaggccatc
tgaacgttcaacagattgttgaccgccacaccagggagctcaagacccaagtagaggaccttaatgagaa
cctgctgaaattgaaagaggcacttaagacctccaagaaccgggagaactctctgaccgacaatctgaac
gatctgaacaatgagctgcagaagaaacagaaagcctacaataagatactgcgagaaaagaagaaatag
accaggagaacgatgagctcaaacggcagatcaaaaggctgacaagcggcctgcaaggcaaacctctcac
cgacaataagcagtccctgatcgaggaactgcagcggaaagtgaagaaactcgaaaaccaacttgaaggg
aaggtgaagaagttgaccttaagcccatgaaagagaaaaacgcaaaggaggaactcattagatgggagg
agggcaaaaagtggcaggccaaaatcgaagggataaggaacaaattgaaagagaaggaaggggaagtgtt
tactctgaccaagcagctcaatactctcaaggaccttttttgctaaagccgacaaagagaaactgaccctg
cagagaaagctgaaaacaacaggcatgaccgtggaccaggtgttggggattagggccttggagagtgaaa
aggagctggaggagctgaaaaagcgcaatctggacttggagaatgatatctgtatatgcgcgctcacca
```

FIGURE 10A (cont'd)

```
ggctctgccgagggacagcgtggtggaggacctccatttgcaaaatcgatatctccaagagaagctccat
gcgctggaaaaacagttctctaaagatacctattccaaaccttctattagcggcattgaatcagacgatc
attgccaaagggagcaggaactgcagaaggaaaacttgaagctgagctctgagaacattgagctgaagtt
ccagctggagcaagccaataaggatctccctcggctgaagaaccaggttcgggacttgaaggagatgtgc
gagtttctcaaaaaggaaaaggcagaggttcagcgcaagctcgggcacgtgagaggctctgggaggagtg
gaaaaaccataccagagcttgagaaaactatcggtttgatgaaaaaggtcgtggagaaagtccagagaga
aaatgagcagctgaaaaaggccagtggcattctgacctcagagaagatggcaaacatcgaacaagagaac
gagaagctcaaggctgaactggaaaagcttaaggctcatctggggcaccagctgtctatgcactatgaaa
gcaagacaaaaggcaccgagaagataatcgccgagaatgagcgcctgagaaaagaactgaagaaggagac
tgatgccgctgaaaagctgagaatcgcaaagaataaccttgaaatactgaatgagaagatgaccgtgcag
ctcgaggaaaccggaaagcgactgcagttcgctgaatctcgagggccacaactcgagggagcggactcta
aaagctggaagagtatagtcgtcactaggatgtatgaaaccaagctgaaggaactggaaacggacattgc
taagaaaaaccagtccatcacagatctgaaacagttggtaaaagaggctactgaaagggagcagaaagtc
aataagtataacgaggacctcgaacagcagatcaagatactgaaacacgtgccagaaggggcggaaacgg
agcaaggcctgaaacgagaactgcaagtgctgcgactggctaatcaccagctggataaggagaaagcaga
gctgatccatcagatagaagcgaataaggatcaatctggtgcggaatctaccatacccgacgccgatcag
cttaaggagaagattaaggatctcgaaactcagttgaagatgagcgacttggaaaaacagcacttgaagg
aagagattaagaaactcaagaaggaactcgagaacttcgaccctagtttctttgaggaaatcgaggatct
gaaatacaactataaggaggaagtgaagaagaatatcttgctggaagaaaaggtgaaaaagctttcagag
caactcggcgtggagctgacctctcccgtagccgcaagtgaggagtttgaggatgaagaagaaagccctg
ttaacttcccgatctat
```

FIGURE 10B

SEQ ID NO: 4

```
MPPNINWKEI MKVDPDDLPR QEELADNLLI SLSKVEVNEL KSEKQENVIH LFRITQSLMK
MKAQEVELAL EEVEKAGEEQ AKFENQLKTK VMKLENELEM AQQSAGGRDT RFLRNEICQL
EKQLEQKDRE LEDMEKELEK EKKVNEQLAL RNEEAENENS KLRRENKRLK KKNEQLCQDI
IDYQKQIDSQ KETLLSRRGE DSDYRSQLSK KNYELIQYLD EIQTLTEANE KIEVQNQEMR
KNLEESVQEM EKMTDEYNRM KAIVHQTDNV IDQLKKENDH YQLQVQELTD LLKSKNEEDD
PIMVAVNAKV EEWKLILSSK DDEIIEYQQM LHNLREKLKN AQLDADKSNV MALQQGIQER
DSQIKMLTEQ VEQYTKEMEK NTCIIEDLKN ELQRNKGAST LSQQTHMKIQ STLDILKEKT
KEAERTAELA EADAREKDKE LVEALKRLKD YESGVYGLED AVVEIKNCKN QIKIRDREIE
ILTKEINKLE LKISDFLDEN EALRERVGLE PKTMIDLTEF RNSKHLKQQQ YPAENQILLK
EIESLEEERL DLKKKIRQMA QERGKRSATS GLTTEDLNLT ENISQGDRIS ERKLDLLSLK
NMSEAQSKNE FLSRELIEKE RDLERSRTVI AKFQNKLKEL VEENKQLEEG MKEILQAIKE
MQKDPDVKGG ETSLIIPSLE RLVNAIESKN AEGIFDASLH LKAQVDQLTG RNEELRQELR
ESRKEAINYS QQLAKANLKI DHLEKETSLL RQSEGSNVVF KGIDLPDGIA PSSASIINSQ
NEYLIHLLQE LENKEKKLKN LEDSLEDYNR KFAVIRHQQS LLYKEYLSEK ETWKTESKTI
KEEKRKLEDQ VQQDAIKVKE YNNLLNALQM DSDEMKKILA ENSRKITVLQ VNEKSLIRQY
TTLVELERQL RKENEKQKNE LLSMEAEVCE KIGCLQRFKE MAIFKIAALQ KVVDNSVSLS
ELELANKQYN ELTAKYRDIL QKDNMLVQRT SNLEHLECEN ISLKEQVESI NKELEITKEK
LHTIEQAWEQ ETKLGNESSM DKAKKSITNS DIVSISKKIT MLEMKELNER QRAEHCQKMY
EHLRTSLKQM EERNFELETK FAELTKINLD AQKVEQMLRD ELADSVSKAV SDADRQRILE
LEKNEMELKV EVSKLREISD IARRQVEILN AQQQSRDKEV ESLPMQLLDY QAQSDEKSLI
AKLHQHNVSL QLSEATALGK LESITSKLQK MEAYNLRLEQ KLDEKEQALY YARLEGRNPA
KHLRQTIQSL RRQFSGALPL AQQEKFSKTM IQLQNDKLKI MQEMKNSQQE HRNMENKTLE
MELKLKGLEE LISTLKDTKG AQKVINWHMK IEELRLQELK LNRELVKDKE EIKYLNNIIS
EYERTISSLE EEIVQQNKFH EERQMAWDQR EVDLERQLDI FDRQQNEILN AAQKFEEATG
SIPDPSLPLP NQLEIALRKI KENIRIILET RATCKSLEEK LKEKESALRL AEQNILSRDK
VINELRLRLP ATAEREKLIA ELGRKEMEPK SHHTLKIAHQ TIANMQARLN QKEEVLKKYQ
RLLEKAREEQ REIVKKHEED LHILHHRLEL QADSSLNKFK QTAWDLMKQS PTPVPTNKHF
IRLAEMEQTV AEQDDSLSSL LVKLKKVSQD LERQREITEL KVKEFENIKL QLQENHEDEV
KKVKAEVEDL KYLLDQSQKE SQCLKSELQA QKEANSRAPT TTMRNLVERL KSQLALKEKQ
QKALSRALLE LRAEMTAAAE ERIISATSQK EAHLNVQQIV DRHTRELKTQ VEDLNENLLK
LKEALKTSKN RENSLTDNLN DLNNELQKKQ KAYNKILREK EEIDQENDEL KRQIKRLTSG
LQGKPLTDNK QSLIEELQRK VKKLENQLEG KVEEVDLKPM KEKNAKEELI RWEEGKKWQA
KIEGIPNKLK EKEGEVFTLT KQLNTLKDLF AKADKEKLTL QRKLKTTGMT VDQVLGIRAL
ESEKELEELK KPNLDLENDI LYMRAHQALP RDSVVEDLHL QNRYLQEKLH ALEKQFSKDT
YSKPSISGIE SDDHCQREQE LQKENLKLSS ENIELKFQLE QANKDLPRLK NQVRDLKEMC
EFLKKEKAEV QRKLGHVRGS GRSGKTIPEL EKTIGLMKKV VEKVQRENEQ LKKASGILTS
EKMANIEQEN EKLKAELEKL KAHLGHQLSM HYESKTKGTE KIIAENERLR KELKKETDAA
EKLRIAKNNL EILNEKMTVQ LEETGKRLQF AESRGPQLEG ADSKSWKSIV VTRMYETKLK
ELETDIAKKN QSITDLKQLV KEATEREQKV NKYNEDLEQQ IKILKHVPEG AETEQGLKRE
LQVLRLANHQ LDKEKAELIH QIEANKDQSG AESTIPDADQ LKEKIKDLET QLKMSDLEKQ
HLKEEIKKLK KELENFDPSF FEEIEDLKYN YKEEVKKNIL LEEKVKKLSE QLGVELTSPV
AASEEFEDEE ESPVNFPIY
```

FIGURE 11A

SEQ ID NO: 5 atggagttggaggacatggaaaaggagctcgaaaagaaaagaaagtgaatgagcagctcgccctgcgga
acgaagaagccgaaaacgaaaacagtaagctgagaagggaaaacaaacggctgaaaaagaagaacgagca
gctctgtcaggatatcatagattaccagaaacagatcgattcacaaaaagaaactttgctctcacgaagg
ggagaagatagcgactatagatcacagctcagtaagaagaactacgagctgattcagtacttggatgaaa
ttcagaccctgacagaagccaatgagaaaatcgaagtacagaaccaagaaatgcggaaaaacctcgagga
gagcgtgcaagagatggagaagatgaccgacgaatacaaccggatgaaagctattgtacatcagactgac
aacgtcatcgatcaattgaagaagaaaacgaccactaccaattgcaagttcaagagctgaccgatctcc
tcaaatccaaaaacgaggaggacgacccataatggtggccgtgaacgctaaagtcgaagagtggaaact
gatcctctcctccaaggatgacgagattatcgaatatcagcagatgctgcacaatctgcgcgagaagttg
aagaatgcacagctcgacgccgacaaatctaatgtaatggccctgcagcagggaatccaagaaagggata
gtcaaatcaaaatgcttactgagcaagtcgaacagtacaccaaagagatggagaaaCaccttaaggccca
agtcgatcagctgacaggcagaaatgaggagcttcgccaggaactccgcgagtccgcaaagaagcaatc
aactatagtcagcagctggcaaaagctaacctcaaaatcgaccatctcgaaaaagaaacgtccctgctca
gacagtccgagggcagcaatgttgtgttcaagggcatagatctcccggacggcattgccccagtagtgc
ttccatcataaactcccaaaacgaatacttgatccatctgctgcaagagcttgagaacaaggagaagaaa
cttaagaatttggaggacagcctcgaggactacaataggaagttcgctgtcatccggcaccagcagagct
tgttgtataaggaatatcttagtgagaaggagacttggaaaacagagagtaaaacgataaaggaagagaa
gcgcaaactggaggaccaggttcagcaggatgccattaaggtgaaagagtacaataaccttctgaatgcg
ttgcagatggacagcgacgagatgaagaaaatcttggctgagaattcccggaaaatcaccgtgctccaag
tcaatgagaagtccctcataagacagtacaccacactcgtcgaactggaaagacagctgaggaaggagaa
cgaaaaacagaaaacgagctgcttagcatggaggcgaagtatgcgagaagataggatgtctgcaaagg
ttcaaagagatggccatattcaagatcgcggcactccagaaagtggtcgataactctgtgtctctcagcg
agttggaactggccaataagcagtacaatgagctgacagccaagtatagagatattctccaaaaggacaa
tatgttggtccagaggacttcaaatcttgagcacttggagtgtgagaacatttcacttaaagaacaagta
gagtccatcaataaggagctggaaatcacaaaagaaaaactgcacacaatagaacaagcatgggaacagg
aaactaaactgggcaacgaaagcagcatggctaagcatctgcggcagactattcagagcctgcggaggca
attcagcggagccctgcctctcgctcagcaagagaagttttctaaaacaatgatacagctgcaaaatgat
aaactcaaaatcatgcaagagatgaagaactctcagcaggagcacagaaacatggagaacaagacactgg
agatggaactcaagttgaaagggctggaggagttgatttctaccctaaggatacaaaaggggcacaaaa
ggtcattaactggcatatgaagatagaggaactgagactgcaagaactcaaactgaatagagagttggtg
aaggacaaagaagagatcaagtaccttaacaatatcatctcagaatacgagcggactatcagttcactgg
aggaggagattgttcagcagaacaaattccatgaggaaaggcagatggcttgggatcagagagaagtgga
tttggagaggcagctggacatctttgatagacaacagaatgagatcctcaacgcggcacagaaattcgaa
gaagcgacaggttcaatccccgatccatctcttccactcccaaatcagcttgagattgctctgagaaaga
tcaaggaaaacatacggattatccttgagactagagctacttgcaagagcctcgaagaaaactgaagga
gaaggagtctgcactgcggcttgcagagcagaatatcctgtctcgggataaggttatcaacgaactgcgc
ctgaggcttcctgctaccgccgagagagagaaactgattgctgaacttggacgaaaagaaatggaaccga
aatctcatcacacgctcaagattgcccaccagacaatagccaatatgcaggccaggctgaatcagaaaga
ggaggtgctgaagaagtatcaacgcctgctggagaaagctagggaggagcagAgagagattgtgaaaaag
cacgaagaggacctccatatcctccatcatcggttggagcttcaggcagattcctccctgaacaagttta
agcagacagcctgggacgatcagtcccagaaggagtcacagtgcttgaaaagcgaactgcaggcacagaa

FIGURE 11A (cont'd)

```
ggaagccaatagccgagccoctaccacgactatgagaaacttggtggaacggctcaaatcccagctcgcc
ttgaaagagaagcagcagaaagcactgtcccgagcgttgcttgagctgcgagctgagatgacggcagcag
ccgaggagcgcatcatttctgctaccagccaaaaagaggcccatctgaacgttcaacagattgttgaccg
ccacaccagggagctcaagacccaagtagaggaccttaatgagaacctgctgaaattgaaagaggcactt
aagacctccaagaaccgggagaactctctgaccgacaatctgaacgatctgaacaatgagctgcagaaga
aacagaaagcctacaataagatactgcgagaaaaagaagaaatagaccaggagaacgatgagctcaaacg
gcagatcaaaaggctgacaagcggcctgcaaggcaaacctctcaccgacaataagcagtccctgatcgag
gaactgcagcggaaagtgaagaaactcgaaaaccaacttgaagggaaggtggaagaagttgaccttaagc
ccatgaaagagaaaaacgcaaaggaggaactcattagatgggaggagggcaaaaagtggcaggccaaaat
cgaagggataaggaacaaattgaaagagaaggaagggggaagtgtttactctgaccaagcagctcaatact
ctcaaggacttttttgctaaagccgacaaagagaaactgaccctgcagagaaagctgaaaacaacaggca
tgaccgtggaccaggtgttggggattagggccttggagagtgaaaaggagctggaggagctgaaa
```

FIGURE 11B

SEQ ID NO: 6

```
MELEDMEKEL EKEKKVNEQL ALRNEEAENE NSKLRRENKR LKKKNEQLCQ DIIDYQKQID
SQKETLLSRR GEDSDYRSQL SKKNYELIQY LDEIQTLTEA NEKIEVQNQE MRKNLEESVQ
EMEKMTDEYN RMKAIVHQTD NVIDQLKKEN DHYQLQVQEL TDLLKSKNEE DDPIMVAVNA
KVEEWKLILS SKDDEIIEYQ QMLHNLREKL KNAQLDADKS NVMALQQGIQ ERDSQIKMLT
EQVEQYTKEM EKHLKAQVDQ LTGRNEELRQ ELRESRKEAI NYSQQLAKAN LKIDHLEKET
SLLRQSEGSN VVFKGIDLPD GIAPSSASII NSQNEYLIHL LQELENKEKK LKNLEDSLED
YNRKFAVIRH QQSLLYKEYL SEKETWKTES KTIKEEKRKL EDQVQQDAIK VKEYNNLLNA
LQMDSDEMKK ILAENSRKIT VLQVNEKSLI RQYTTLVELE RQLRKENEKQ KNELLSMEAE
VCEKIGCLQR FKEMAIFKIA ALQKVVDNSV SLSELELANK QYNELTAKYR DILQKDNMLV
QRTSNLEHLE CENISLKEQV ESINKELEIT KEKLHTIEQA WEQETKLGNE SSMAKHLRQT
IQSLRRQFSG ALPLAQQEKF SKTMIQLQND KLKIMQEMKN SQQEHRNMEN KTLEMELKLK
GLEELISTLK DTKGAQKVIN WHMKIEELRL QELKLNRELV KDKEEIKYLN NIISEYERTI
SSLEEEIVQQ NKFHEERQMA WDQREVDLER QLDIFDRQQN EILNAAQKFE EATGSIPDPS
LPLPNQLEIA LRKIKENIRI ILETRATCKS LEEKLKEKES ALRLAEQNIL SRDKVINELR
LRLPATAERE KLIAELGRKE MEPKSHHTLK IAHQTIANMQ ARLNQKEEVL KKYQRLLEKA
REEQREIVKK HEEDLHILHH RLELQADSSL NKFKQTAWDD QSQKESQCLK SELQAQKEAN
SRAPTTTMRN LVERLKSQLA LKEKQQKALS RALLELRAEM TAAAEERIIS ATSQKEAHLN
VQQIVDRHTR ELKTQVEDLN ENLLKLKEAL KTSKNRENSL TDNLNDLNNE LQKKQKAYNK
ILREKEEIDQ ENDELKRQIK RLTSGLQGKP LTDNKQSLIE ELQRKVKKLE NQLEGKVEEV
DLKPMKEKNA KEELIRWEEG KKWQAKIEGI RNKLKEKEGE VFTLTKQLNT LKDLFAKADK
EKLTLQRKLK TTGMTVDQVL GIRALESEKE LEELK
```

FIGURES 12A-12C
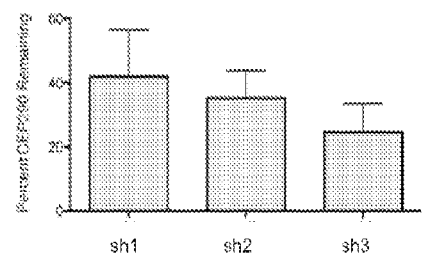
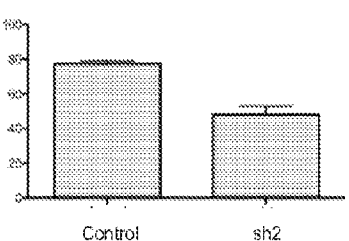
FIGURES 13A-13C
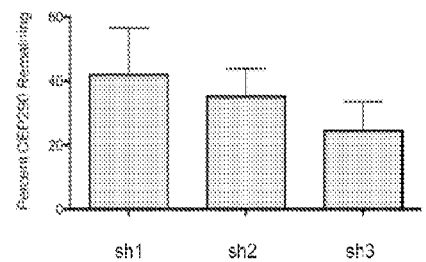
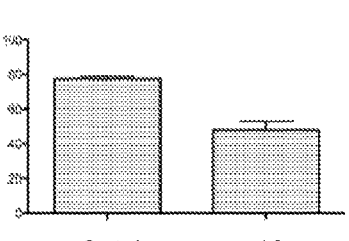

A

B

COMPOSITIONS AND METHODS FOR TREATMENT OF DISORDERS RELATED TO CEP290

CROSS-REFERENCE TO RELATED APPLICATIONS

This application is a national stage of International Patent Application No. PCT/US2014/046408, filed Jul. 11, 2014, which claims the benefit of the priority of U.S. Provisional Patent Application No. 61/847,016, filed Jul. 16, 2013, which applications are incorporated herein by reference.

STATEMENT REGARDING FEDERALLY SPONSORED RESEARCH OR DEVELOPMENT

This invention was made with government support under Grant Nos. R24EY019861 and 8DP1EY023177 awarded by the National Institutes of Health. The government has certain rights in this invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-Y6321PCT ST25.txt".

BACKGROUND OF THE INVENTION

Defects in primary cilium formation and function are responsible for a variety of human diseases and developmental disorders, collectively termed ciliopathies. While the ciliopathies are diverse in both phenotype and etiology, specific genes, including CEP290, have been implicated as having causative roles in multiple cilium-associated disorders. Mutations in the gene CEP290 have been described in up to 20% of cases of the devastating inherited blinding disease Leber congenital amaurosis and in numerous cases of other more debilitating ciliopathies, such as Joubert syndrome, Senior Løken Syndrome, and Meckel-Grüber syndrome. These disorders range in severity from isolated retinal degeneration to renal dysfunction, central nervous system malformations, hepatic development defects, and embryonic lethality.

Attempts to treat genetic defects have been attempted by delivery of normal genes to the cells expressing the defective genes, such as recombinant adeno-associated virus (AAV)-based therapeutics. See, e.g., U.S. Pat. No. 8,147,823. Generally, large gene sequences have been difficult to fit effectively into some of the more useful vector delivery systems. The extension, to CEP290 patients, of recombinant adeno-associated virus (AAV)-based therapeutics, which have proven safe and effective in the treatment of another genetic cause of LCA, has been hindered by CEP290's large size, precluding it from packaging in AAV.

There remains a need in the art for additional therapeutic compositions and methods for treatment of LCA and other ciliopathies.

SUMMARY OF THE INVENTION

In one aspect, a composition comprises a recombinant vector carrying a nucleic acid sequence encoding a fragment of the CEP290 gene lacking all or portions of at least one of its N-terminal and C-terminal inhibitory regions. The CEP290 fragment is under the control of regulatory sequences which express the product of the gene in a selected cell of a mammalian subject, and a pharmaceutically acceptable carrier. Embodiments comprise nucleic acid sequences of CEP290 which include continuous fragments of CEP290 or discontinuous fragments of CEP290 spliced together in the same reading frame. In one embodiment, the nucleic acid sequence comprises a sequence encoding amino acids 1695 to 1966 (SEQ ID NO: 53) of CEP290, i.e., aa1695 to 1966 of SEQ ID NO: 2. In still another embodiment, the vector of the compositions is an adeno-associated vector.

In another aspect, a composition comprises a recombinant adeno-associated vector carrying a nucleic acid sequence encoding a fragment of the CEP290 gene lacking at least one of its N-terminal and C-terminal inhibitory regions, under the control of regulatory sequences which express the product of said gene in a photoreceptor cell of a mammalian subject, and a pharmaceutically acceptable carrier.

In another aspect, a synthetic, or recombinant protein is disclosed that comprises discontinuous CEP290 amino acid fragments spliced together in a single open reading frame. This synthetic protein has biological activity that mimics the biological activity of normal full length CEP290. In certain embodiments, the discontinuous CEP290 amino acid fragments are one or more of aa130 to 380 (SEQ ID NO: 49), aa700 to 1040 (SEQ ID NO: 51) aa1260 to 1605 (SEQ ID NO: 52), aa1695 to 1990 (SEQ ID NO: 54), aa1695 to 1966 (SEQ ID NO: 53) of CEP290, or aa1695 to 1995 (SEQ ID NO: 55) of CEP290 of SEQ ID NO: 2 or 4. In another embodiment, the synthetic or recombinant protein has the sequence of SEQ ID NO: 6.

In another aspect, a synthetic or recombinant nucleic acid sequence is provided that encodes the above-referenced protein comprising discontinuous CEP290 amino acid fragments spliced together in a single open reading frame.

In another aspect, compositions containing the synthetic or recombinant protein or nucleic acid sequences also contain therapeutically acceptable carriers. Such compositions may include the vectors above which carry the nucleic acid sequences, or other components.

In yet another aspect, a method of treating a mammalian subject having a disease associated with a CEP290 mutation or defect in the CEP290 gene, protein or expression levels is provided. The method comprises administering to said subject an effective concentration of any of the compositions as described above and in further detail in the specification. This method can involve administering a composition as described herein to cells of the retina, e.g., photoreceptors, the central nervous system, the brain, kidney, bone or olfactory epithelium.

In still another aspect, a method of preventing, arresting progression of or ameliorating vision loss associated with Lebers Congenital Amaurosis in a subject is provided. The method comprises administering to a mammalian subject in need thereof an effective concentration of any of the compositions described herein. In one embodiment, the composition comprises a recombinant adeno-associated virus (AAV) carrying a nucleic acid sequence encoding a fragment of the CEP290 gene lacking at least one of its N-terminal and C-terminal inhibitory regions, under the control of regulatory sequences which express the product of said gene in a photoreceptor cell of a mammalian subject, and a pharmaceutically acceptable carrier.

Other aspects of the invention and disclosure are described in the following detailed description.

BRIEF DESCRIPTION OF THE FIGURES

FIG. 1A is a scale representation of human CEP290 SEQ ID NO: 2. Known human CEP290 mutations are noted by tick marks. The indicated domains and mutations are adapted from reference 30. FIG. 1B are fluorescence microscopy images showing the localization pattern of GFP fusions of full length (FL) and truncated CEP290 constructs in hTERT-RPE1 cells. Cells were stained for ARL13B and with DAPI. Scale bars are 5 µm. Insets show 3×magnified views of areas (in boxes) of colocalization between CEP290 truncations and ARL13B. FIG. 1C show representative membrane flotation assay performed on hTERT-RPE1 cells overexpressing CEP290 aa 1 to 580 (SEQ ID NO: 47) of SEQ ID NO: 2. Equal amounts of each of five fractions, beginning from the top (1) and ending at the bottom (8) of the sucrose gradient were analyzed. The sucrose percentage and the expected protein composition of each fraction are indicated. Blots were probed for GFP to detect CEP290 aa 1 to 580 and for the indicated controls. Relevant molecular weight markers are shown in kDa. FIG. 1D shows that ARL13B positive vesicles were immunoprecipitated from postnuclear supernatants of hTERT-RPE1 cells expressing the indicated CEP290 truncations or GFP alone. The input, unbound fraction (UB) and immunoprecipitated fraction (IP) were probed with an anti-GFP antibody to detect our truncations. Relevant molecular weight markers are shown in kDa. FIG. 1E show the peripheral membrane (Peri.) and integral membrane protein (Int.) fractions of hTERTRPE1 cells expressing the indicated CEP290 truncations that were isolated and probed for GFP to detect CEP290 truncations and for the indicated controls. Relevant molecular weight markers are shown in kDa.

FIG. 2A are fluorescence microscopy images showing the localization pattern of GFP fusions of full length (FL) and truncated CFP290 constructs in hTERTRPE1 cells stained for LAMP2 and with DAPI. Scale bars are 5 µm. Insets show 3× magnified views of areas (in boxes) illustrating lack of colocalization between CEP290 truncations and LAMP2. FIG. 2B shows the results of subcellular fractionation experiments performed on 293T cells expressing CEP290 constructs, Cells were fractionated into cytoplasmic (C), membrane (M), nuclear (N), and cytoskeletal (S) fractions and analyzed by western blotting. Relevant molecular weight markers are shown in kDa. FIG. 2C shows the percent of each truncation present in the membrane fraction. Data are presented as mean±SD, n=3. Asterisks indicate statistical significance over GFP alone. FIG. 2D show the results of liposome co-flotation assays performed on purified. CEP290 aa 1 to 580. Data is shown for assays performed with CEP290 aa 1 to 580, both with and without liposomes, and with BSA. as a control. Equal amounts of each of five fractions, beginning from the top (1) and ending at the bottom (5) of the sucrose gradient were analyzed. The sucrose percentage and the expected protein composition of each fraction are indicated. Relevant molecular weight markers are shown in kDa. FIG. 2E illustrate helical wheel projection of CEP290 aa 257 to 292 (SEQ ID NO: 50). Darkest circles represent negatively charged amino acids; slightly less dark circles represent positively charged amino acids; the lightest grey circles represent polar, uncharged amino acids, and medium grey circles represent nonpolar amino acids. By aligning CEP290's predicted amphipathic helix from Gallus SEQ ID NO: 35, Meleagris SEQ ID NO: 36, Rattus SEQ ID NO: 37, Mus SEQ ID NO: 38, Pongo SEQ ID NO: 39,Macaca SEQ ID NO: 40, Homo sapiens SEQ ID NO: 41, Felis SEQ ID NO: 42, Ailuropoda SEQ ID NO: 43 and Danio SEQ ID NO: 45, one can see there is usually conservation of polarity and charge between the divergent residues.

FIGS. 3A to 3C show that CEP290 colocalizes with microtubules via region M, and truncation of its N- and C-termini enhances this colocalization. FIG. 3A are fluorescence confocal microscopy images showing the localization pattern of GFP fusions of full length (FL) and truncated CEP290 constructs expressed in hTERT-RPE1 cells or in HEK293T cells. Samples were stained for α-tubulin or acetylated α-tubulin, pericentrin or with DAPI. Scale bars are 10 µm. Insets show 10× magnified views of areas of colocalization (in boxes) between CEP290 truncations and pericentrin. In all cases, truncations partially colocalize with pericentrin. In some cases, truncations colocalize with tubulin. Region M is necessary and sufficient for tubulin colocalization. FIG. 3B are scale representations of the library of CEP290 truncations tested in FIG. 3A. Included is a summary of the extent of colocalization with tubulin, rated on a scale ranging from negative (−) to highly positive. Truncations were also in vitro transcribed and translated and subjected to a microtubule MT sedimentation assay. The recombinantly expressed and purified microtubule binding region of CEP290 was similarly subjected to a MT sedimentation assay. FIG. 3C illustrates that for each truncation, the percent of transfected hTERT-RPE1 cells in which the GFP fused truncation displayed a fibrillar localization pattern was determined. At least 100 transfected cells were counted per experiment. Data are presented as mean±SD, n=3. Quantification of the different localization patterns of each truncation from three independent experiments. Region M of CEP290 is necessary and sufficient for fibrillar localization. The inclusion of the N-and C-termini diminishes the extent to which truncations assume a fibrillar pattern of localization.

FIG. 4A shows representative confocal fluorescence microscopy images of GFP fusions of full length (FL) and truncated CEP290 constructs expressed in hTERT-RPE1 cells stained for acetylated α-tubulin and with DAPI. Scale bars are 10 µm. Truncations containing CEP290 aa1695 to 1966 of SEQ ID NO: 2 perturb the acetylated tubulin staining pattern in hTert-RPI and 293T cells, and deletion of the N- and C-termini enhance the effect. Confocal images of CEP290 truncations overexpressed in hTERT-RPE1 cells stained with an anti-acetylated tubulin antibody. Truncations containing aa1695 to 1966 of SEQ ID NO: 2 increase the intensity of acetylated tubulin staining and result in more bundles of acetylated MTs compared to untransfected cells. FIG. 4B show percent of transfected 293T cells showing an increase in the intensity, and perturbation in pattern, of acetylated α-tubulin staining compared to untransfected cells, following transfection with CEP290 truncations. Deletion of both the N- and C-termini, but not either alone, significantly increases the intensity of acetylated tubulin staining. 100 transfected cells were counted per experiment. Data are presented as mean±SD, n=5. Means with different letters are significantly different. FIG. 4C are Western blots of microtubule (MT) co-sedimentation assays for in vitro transcribed and translated CEP290 truncation mutants. The resulting supernatants (S) and microtubule pellets (P) were probed for the presence of the GFP-fused truncations and are shown for assays performed both with (+MT) and without (−MT) microtubules. Relevant molecular weight markers are shown in kDa. FIG. 4D shows the percent of each truncation co-sedimenting with microtubules. Quantification of the percent of total truncation present in the MT pellet for three independent experiments is shown. Only minimal pelleting is observed in the −MT controls. AA1695 to 1966 of SEQ ID NO: 2 are necessary for significant MT binding, and deletion of both the N- and C-termini, but not of either alone, significantly increases MT binding. Data are presented as mean±SD, n=3. Means with different letters are significantly different. The N- and C-termini cooperatively inhibit MT binding. FIG. 4E are Coomassie-stained gel of microtubule co-sedimentation assays performed with recombinantly expressed and purified CEP290 truncation M subjected to a MT sedimentation assay with increasing concentrations of microtubules (tubulin). Truncation M directly binds MTs with an apparent $K_d$ in the nanomolar range, comparable to other MT binding proteins. The supernatants (S) and microtubule pellets (P) are shown. Relevant molecular weight markers are shown in kDa. CEP290 aa1695 to 1966 of SEQ ID NO: 2 directly bind MTs with a $K_d$ in the nanomolar range. FIG. 4F is a binding curve of microtubule cosedimentation assays as in FIG. 4E. The fraction of truncation M present in the pellet in the absence of microtubules was subtracted from all data points. Data points are presented as means±SD, n=3. A curve was fit to the data points using the non-linear regression functionality of the GraphPad Prism program.

FIGS. 5A to 5G show that the overexpression of either the N-or C-terminal regulatory regions of CEP290 ablates the normal inhibition of CEP290. FIG. 5A shows fluorescence microscopy fields of hTERT-RPE1 cells transduced with lentiviral empty vector (EV), or vectors encoding either the N-(aa 1 to 580) or C-terminus (aa 1966 to 2479) of CEP290 (SEQ ID NO: 59). Cells were stained for acetylated α-tubulin and pericentrin to detect primary cilia and with DAPI. Arrowheads indicate primary cilia. Arrows indicate cells with multiple axonemes originating from the same focus of pericentrin. Scale bars are 10 µm. FIG. 5B show the percent of lentivirus-treated cells forming primary cilia. Data are presented as mean±SD, n=3. 100 cells were counted per experiment. FIG. 5C show fluorescence microscopy images of single hTERT-RPE1 cells transduced with lentiviral vectors as in FIG. 5A. Cells were stained for acetylated α-tubulin to detect primary cilia and with DAPI. Scale bars are 5 µm FIG. 5D shows the average primary cilium length for hTERT-RPE1cells as in FIG. 5C. Data are presented as mean±SD, n=3. A total of at least 150 cilia were measured per condition. FIG. 5E are fluorescence microscopy images of hTERT-RPE1 cells that formed multiple cilia after transduction with lentiviral vector encoding the N-terminus of CEP290. Cells were stained with acetylated αtublin, ARL13B, and with DAPI. Scale bars are 5 µm. FIG. 5F are fluorescence microscopy images of hTERT-RPE1 cells that formed multiple cilia after transduction with lentiviral vector encoding the N-terminus of CEP290. Cells were stained with acetylated α-tubulin, pericentrin and with DAPI. Scale bars are 5 µm. FIG. 5G shows the percent of lentivirus treated hTERT-RPE1 cells forming multiple cilia. At least 100 cells were counted per experiment. Data are presented as mean±SD, n=3.

FIG. 6A is a schematic representation of the microtubule binding region of human CEP290 in relation to the rd16 mouse deletion (17). Truncations of CEP290 representing the part of the microtubule binding region deleted in the rd16 mouse and the part of the microtubule binding region maintained in the rd16 mouse were created as shown. FIG. 6B are confocal fluorescence microscopy images showing the localization pattern of the GFP-tagged "Maintained" and "Deleted" CEP290 truncations. Cells were stained for α-tubulin, pericentrin and with DAPI. Scale bars are 10 µm. FIG. 6C are immunoblots of representative microtubule co-sedimentation assays for in vitro transcribed and translated "Maintained" and "Deleted" CEP290 truncations. The supernatant (S) and microtubule pellet (P) fractions are shown in assays performed both with (+MT) and without (−MT) the addition of microtubules. Relevant molecular weight markers are shown in kDa. FIG. 6D shows the percent of each truncation co-sedimenting with microtubules. Data are presented as mean±SD, n=2. FIG. 6E are representative western blots of microtubule co-sedimentation assays performed with full length WT and rd16 Cep290 from mouse brain homogenate. The supernatant (S) and microtubule pellet (P) fractions are shown in assays performed on samples induced to polymerize microtubules (+MT) and samples treated to prevent microtubule polymerization (−MT). Relevant molecular weight markers are shown in kDa. FIG. 6F shows percent of WT and rd16 CEP290 co-sedimenting with microtubules. Data are presented as mean±SD, n=3. Asterisks indicate statistical significance over −MT samples.

FIG. 7A show fluorescence microscopy fields of WT primary dermal fibroblasts that were stained for acetylated α-tubulin to identify primary cilia, and stained with DAPI. Fibroblasts were grown in media with (Fed) or without (Starved) serum. Arrowheads indicate primary cilia. Scale bars are 10 µm. FIG. 7B show fluorescence microscopy fields of rd16 primary dermal fibroblasts stained for acetylated α-tubulin to identify primary cilia, and stained with DAPI. Fibroblasts were grown in media with (Fed) or without (Starved) serum. Arrowheads indicate primary cilia. Scale bars are 10 µm. FIG. 7C show the percent of WT and rd16 primary dermal fibroblasts that form primary cilia in serum fed and serum starved conditions. Quantification was based on separate experiments on fibroblasts coming from 3 different animals per genotype. At least 100 cells were counted per experiment. Data are presented as mean±SD, n=5. FIG. 7D show high magnification fluorescent microscopy images of representative serum-starved WT and rd16 primary dermal fibroblasts stained for acetylated α-tubulin to identify primary cilia, and stained with DAPI. Scale bars are 5 µm. FIG. 7E are average cilium length of serum starved WT and rd16 primary dermal fibroblasts. Quantification was based on separate experiments on fibroblasts coming from 3 different animals per genotype. At least 50 cilia were measured per experiment, and a total of 400 cilia were measured for both the WT and rd16 fibroblasts. Data are presented as mean±SD, n=5.

FIG. 9A is the nucleic acid sequence encoding full length naturally occurring human CEP290 SEQ ID NO: 1.

FIG. 9B is the amino acid sequence encoding full length naturally occurring human CEP290 SEQ ID NO: 2.

FIG. 10A is a synthetic nucleic acid sequence for codon optimized human CEP290 SEQ ID NO: 3.

FIG. 10B is a synthetic amino acid sequence for codon optimized human CEP290 SEQ ID NO: 4.

FIG. 11A is a synthetic construct which is a minigene for CEP290 SEQ ID NO: 5, which encodes the following CEP290 amino acid fragments, spliced together in a single open reading frame: aa130 to 380, aa700 to 1040, aa1260 to 1605, and aa1695 to 1990.

FIG. 11B is the synthetic amino acid sequence construct SEQ ID NO: 6 encoded by FIG. 11A.

FIGS. 12A to 12C demonstrate the generation and testing of CEP290 shRNA constructs. FIG. 12A shows hTERT-RPE1 cells transiently transfected with three different CEP290 shRNA constructs, which were lysed and analyzed by western blotting for CEP290 levels. Blots were reprobed for GAPDH as a loading control. FIG. 12B shows densitometric quantification of CEP290 protein levels in hTERT-RPE1 cells as in FIG. 12A. CEP290 levels were normalized using GAPDH as a loading control and the percent of CEP290 remaining, compared to untransfected hTERT-RPE1 cells, was determined Immunofluorescence microscopy images of fields of hTERT-RPE1 cells, either untransfected or transfected with CEP290 shRNA construct 2, were stained for acetylated tubulin as a marker of the primary cilium (data not shown). FIG. 12C shows the percent of control and sh2 transfected hTERT-RPE1 cells that formed cilia upon serum starvation.

FIGS. 13A to 13C show the isolation and testing of clonal CEP290 knockdown cell lines. FIG. 13A shows clonal retrovirus-transduced hTERT-RPE1 cell lines expressing CEP290 shRNA 2 that were lysed and analyzed by western blotting for CEP290 levels. Blots were reprobed for GAPDH as a loading control. FIG. 13 B shows densitometric quantification of CEP290 protein levels in these hTERT-RPE1 cells. CEP290 levels were normalized using GAPDH as a loading control and the percent of CEP290 remaining, compared to untransfected hTERT-RPE1 cells, was determined Immunofluorescence microscopy images of fields of control and sh2.8 hTERT-RPE1 cells stained for acetylated tubulin as a marker of the primary cilium were obtained (data not shown). FIG. 13C shows the percent of control and sh2.8 hTERT-RPE1 cells that formed cilia upon serum starvation.

FIG. 14A is a schematic representation of the CEP290 protein with identified functional domains, interacting domains, and protein motifs labeled. Grayed areas represent regions of the protein not included in the miniCEP290 construct. FIG. 14B is a schematic representation of miniCEP290 Immunofluorescence images of hTERT-RPE1 cells transiently transfected with GFP-fused miniCEP290 and stained for acetylated tubulin and pericentrin, and with DAPI were obtained, and showed the localization of miniCEP290 to the ciliary transition zone (data not shown).

DETAILED DESCRIPTION OF THE INVENTION

Figure 1A:
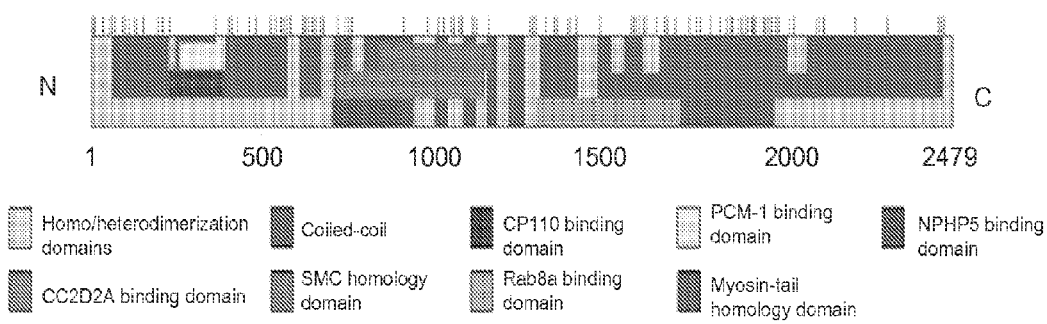
FIGS. 1A to 1E illustrate that CEP290 aa 1 to 380 (SEQ ID NO: 46), i.e., aa 1 to 380 of SEQ ID NO: 2, mediate membrane association.

CEP290 is a vital structural and regulatory element of the ciliary transition zone, elucidation of its molecular functionality at the center of the critically important and disease-relevant pathways of ciliogenesis and IFT. The inventors have identified novel regulatory domains of CEP290 useful in therapeutic interventions for diseases of the cilia caused by mutated CEP290. Truncation mutants or fragments of CEP290 lacking certain of the novel inhibitory domains but maintaining the other functional regions of the protein exhibit normal, or even enhanced, CEP290 function, while at the same time being small enough to fit in certain vectors, such as AAV. The delivery of such a therapeutic to terminally differentiated tissues, such as the retina, to effect permanent activation of CEP290 is useful in the treatment of CEP290-related diseases, such as LCA. The delivery of such a therapeutic is also useful to treat other diseases caused by naturally mutated or non-functional CEP290 in other tissues, such as the brain or kidney or bone.

Four novel functional domains of the CEP290 protein are identified, showing that CEP290 directly binds to the cellular membrane via an N-terminal domain that includes a highly conserved amphipathic helix motif, and directly binds to microtubules through a domain located within its myosin-tail homology domain. Furthermore, CEP290 activity was found to be regulated by two novel autoinhibitory domains within its N- and C-termini, both of which were also found to play critical roles in regulating ciliogenesis. Disruption of the novel microtubule binding domain in the rd16 mouse LCA model was found to be sufficient to induce significant deficits in cilium formation leading to retinal degeneration. Various compositions and treatment methods for CEP290-related diseases utilizing these domains are disclosed.

In one embodiment, a composition comprises a recombinant vector carrying a nucleic acid sequence encoding a fragment of the CEP290 gene lacking at least one of its N-terminal and C-terminal inhibitory regions, under the control of regulatory sequences which express the product of said gene in a selected cell of a mammalian subject, and a pharmaceutically acceptable carrier. In another embodiment, such a composition comprises an effective concentration of a recombinant adeno-associated virus (rAAV) carrying a nucleic acid sequence encoding a CEP290 fragment or truncated gene, as described herein, under the control of regulatory sequences which direct expression of the product of the gene in the subject's ocular cells, formulated with a carrier and additional components suitable for injection. In still another embodiment, the treatment methods are directed to ocular disorders and associated conditions related thereto. Other treatment methods are also disclosed.

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. The definitions used herein are provided for clarity only and are not intended to limit the claimed invention.

As used herein, the term "mammalian subject" or "subject" includes any mammal in need of these methods of treatment or prophylaxis, including particularly humans. Other mammals in need of such treatment or prophylaxis include dogs, cats, or other domesticated animals, horses, livestock, laboratory animals, including non-human primates, etc. The subject may be male or female. In another embodiment, the subject has shown clinical signs of ciliopathy, such as Lebers Congenital Amaurosis. Clinical signs of LCA include, but are not limited to, decreased peripheral vision, decreased central (reading) vision, decreased night vision, loss of color perception, reduction in visual acuity, decreased photoreceptor function, pigmentary changes. In another embodiment, the subject has been diagnosed with LCA. In yet another embodiment, the subject has not yet shown clinical signs of LCA. In still another embodiment, the subject has shown signs or symptoms of another ciliopathy, e.g., disorders of the bone, brain, CNS, kidney, or olefactory epithelia.

As used herein, the term "selected cells" refers to any cell in which a CEP290 mutation causes disease. In one embodiment, the selected cell is an ocular cell, which is any cell associated with the function of, the eye. In one embodiment, the ocular cell is a photoreceptor cells. In another embodiment, the term refers to rod, cone and photosensitive ganglion cells or retinal pigment epithelium (RPE) cells. In another embodiment, the selected cell is a bone cell. In another embodiment, the selected cell is a brain cell or neuron. In another embodiment, the selected cell is a renal or kidney cell. In another embodiment, the selected cell is a mucosal cell, such as an olfactory epithelial cell.

"CEP290 related pathologies" or those caused by a defect or mutation in CEP290 include Leber congenital amaurosis, Joubert syndrome, Senior Løken Syndrome, and Meckel-Grüber syndrome, including isolated retinal degeneration, renal dysfunction, central nervous system malformations, hepatic development defects, and embryonic lethality.

The terms "a" or "an" refers to one or more, for example, "a gene" is understood to represent one or more such genes. As such, the terms "a" (or "an"), "one or more," and "at least one" are used interchangeably herein. As used herein, the term "about" means a variability of 10% from the reference given, unless otherwise specified.

With regard to the following description, it is intended that each of the compositions herein described, is useful, in another embodiment, in the methods of the invention. In addition, it is also intended that each of the compositions herein described as useful in the methods, is, in another embodiment, itself an embodiment of the invention. While various embodiments in the specification are presented using "comprising" language, under other circumstances, a related embodiment is also intended to be interpreted and described using "consisting of" or "consisting essentially of" language.

CEP290 Nucleic Acid and Proteins and Fragments Thereof

"CEP290" is a mammalian gene of about 7.8 kb in size (see NCBI database ref gene 80184 for the full length human gene sequence) which encodes a full length protein of about 2479 amino acids (See e.g., SEQ ID NO: 1 for the human gene sequence). CEP290 participates in the formation of the primary cilium (an organelle found in nearly all cell types) and regulates the trafficking of proteins into and out of the ciliary compartment. Mutations in CEP290 lead to aberrant ciliary trafficking, eventually resulting in pathologies. Mutations in this gene have been associated with a variety of disease functions. It is implicated in LCA, as well as other ciliopathies affecting numerous organ systems, including the retina, CNS, kidney, liver heart and bone.

The nucleic acid sequence encoding a normal CEP290 gene may be derived from any mammal which natively expresses the CEP290 gene, or homolog thereof. In another embodiment, the CEP290 gene sequence is derived from the same mammal that the composition is intended to treat. In another embodiment, the CEP290 is derived from a human. In other embodiments, certain modifications are made to the CEP290 sequence in order to enhance the expression in the target cell. Such modifications include codon optimization. Codon optimization may be performed in a manner such as that described in, e.g., U.S. Pat. Nos. 7,561,972; 7,561,973; and 7,888,112, incorporated herein by reference, and conversion of the sequence surrounding the translational start site to a consensus Kozak sequence. See, Kozak et al, *Nucleic Acids Res.* 15 (20): 8125-8148, incorporated herein by reference.

A full length human nucleic acid sequence for CEP290 is shown as SEQ ID NO. 1 and its full length protein sequence is shown as SEQ ID NO: 2. A full length codon-optimized version of a human nucleic acid sequence is identified herein as SEQ ID NO: 3 with its full length protein sequence identified as SEQ ID NO:4. Throughout this disclosure, numbering of the amino acid fragments of CEP is that of the amino acid sequence of FIG. 10B, SEQ ID NO:2 with the first amino acid of FIG. 10B numbered as 1.

A "CEP290 fragment or truncation" as used herein is defined as a fragment of CEP290 lacking the sequences that inhibit the protein's function. By the term "fragment" or "functional fragment" is meant any fragment that retains the function of the full length CEP290, although not necessarily at the same level of expression or activity. As disclosed herein CEP290 is a microtubule binding protein, with its MT binding activity localized to aa 1695 to 1966 of SEQ ID NO: 2, i.e., the sequence

DQSQKESQCLKSELQAQKEANSRAPTTTMRNLVERLKSQLALKEKQQKA

LSRALLELRAEMTAAAEERIISATSQKEAHLNVQQIVDRHTRELKTQVE

DLNENLLKLKEALKTSKNRENSLTDNLNDLNNELQKKQKAYNKILREKE

EIDQENDELKRQIKRLTSGLQGKPLTDNKQSLIEELQRKKKLENQLEGK

VEEVDLKPMKEKNAKEELIRWEEGKKWQAKIEGIRNKLKEKEGEVFTLT

KQLNTLKDLFAKADKEKLTLQRKLKT.

The inventors identified inhibitory regions at the N and C termini thereof. The inventors have also determined that the N- and C termini of the protein cooperatively inhibit the MT binding activity. As disclosed in detail in the examples below, the inventors determined that the nucleic acid sequence of CEP290 encoding amino acids spanning aa1695 to 1966 were necessary for colocalization with microtubules. While inhibitory functions were found within the N terminal sequences encoding aa 1 to 580, other sequences located at the N-terminus were functional in other ways, e.g., the sequences encoding amino acids 1 to 380 were determined to contain regions necessary for vesicular localization and amino acids 1 to 362 (SEQ ID NO: 45) were determined to contain regions necessary for membrane association Amino acids 257 to 292 were found to be the alpha helix and necessary for reversible interaction. The C-terminal portions of the protein, from about amino acid 2000 to 2479 (SEQ ID NO: 58) or about 1967 to 2479 (SEQ ID NO: 57), were found to cooperatively inhibit microtubule binding with portions of the N-terminal inhibitory sequence within amino acids 1 to 580.

CEP290 nucleic acid fragments or truncated sequences for use in the therapeutic methods described herein can be a single consecutive sequence, such as that encoding CEP290 protein lacking its N terminal membrane binding inhibitory region. In another embodiment, the nucleic acid sequence fragment encodes CEP290 lacking its C terminal membrane binding inhibitory region. In still another useful embodiment, the nucleic acid sequence fragment encodes CEP290 lacking both the N-terminal and C-terminal inhibitory regions. CEP290 fragments consist of a single consecutive CEP290 sequence or spliced together fragments of one or more fragments of CEP290, which together provide the regions necessary for protein function. Such fragments can individually be from about 150 to over 1000 nucleotides in length. The encoded fragments can be from about 50 to over 300 amino acids in length.

Thus in one embodiment a useful CEP209 nucleic acid sequence encodes aa1695 to about 2000 of CEP290 (SEQ ID NO: 56). In one embodiment, the nucleic acid sequence fragment encodes aa 1695 to aa 1990. In another embodiment, the sequence encodes aa 1695 to 1966. Still other nucleic acid sequences encoding continuous or discontinuous amino acids sequences within that range can be included as useful fragments herein. In another embodiment, a useful CEP290 fragment encodes aa100 to 362 (SEQ ID NO: 48). In another embodiment the useful CEP290 fragment encodes amino acids 130 to 380 of CEP290. In another embodiment the useful CEP290 fragment encodes amino acids 130 to 380 of CEP290. In another embodiment the useful CEP290 fragment encodes amino acids 700 to 1040 of CEP290. In another embodiment the useful CEP290 fragment encodes amino acids 1260 to 1605 of CEP290. In still another embodiment, spliced together fragments of one or more of the fragments of CEP290 disclosed herein provide the regions necessary for protein function. In another embodiment, to form a useful CEP290 fragment, the nucleic acid sequences of CEP290are spliced together in the same reading frame. In one embodiment, the CEP290 fragment is useful for delivery to a mammalian cell to replace a mutated version of CEP290 is a nucleic acid minigene encoding CEP fragments spliced together in a single reading frame: aa130 to 380, aa 700 to 1040, aa 1260 to 1605, and aa1695 to 1990. One exemplary CEP290 minigene sequence is shown as SEQ ID NO: 5, with is encoded sequence being SEQ ID NO: 6.

In still another embodiment, the fragment of CEP290 is derived from nucleic acid sequence SEQ ID NO: 1. In another embodiment, the fragment of CEP290 is derived from human codon-optimized nucleic acid sequence SEQ ID NO: 3. In still another embodiment the nucleic acid sequence encoding a fragment of CEP290 is derived from or is the minigene sequence SEQ ID NO: 5. In one embodiment, the CEP290 fragment is useful for delivery to a mammalian cell to replace a mutated version.

It is anticipated that the CEP290 nucleic acid fragments and the CEP290 protein truncates or amino acid fragments identified herein may tolerate certain minor modifications at the nucleic acid level to include, for example, modifications to the nucleotide bases which are silent, e.g., preference codons. In other embodiments, nucleic acid base modifications which change the amino acids, e.g. to improve expression of the resulting peptide/protein are anticipated. Also included as likely modification of fragments are allelic variations, caused by the natural degeneracy of the genetic code. Also included as modification of the CEP290 expressed fragments are analogs, or modified versions, of the CEP290 protein fragments provided herein. Typically, such analogs differ from the specifically identified CEP290 proteins by only one to four codon changes. Examples include CEP290 fragments with conservative amino acid replacements from the CEP290 sequence from which the fragment is derived. Conservative replacements are those that take place within a family of amino acids that are related in their side chains and chemical properties. CEP290 fragments which have at least 80% sequence identity with the above derived fragments from known sequences of CEP290, including the SEQ ID NOs: 1 to 4 herein, are anticipated to be useful in the compositions and methods of this invention.

The Vectors

A variety of known nucleic acid vectors may be used in these methods, e.g., recombinant viruses, such as recombinant adeno-associated virus (AAV), recombinant adenoviruses, recombinant retroviruses, recombinant poxviruses, and other known viruses in the art, as well as plasmids, cosmids and phages, etc. A wealth of publications known to those of skill in the art discusses the use of a variety of such vectors for delivery of genes (see, e.g., Ausubel et al., *Current Protocols in Molecular Biology*, John Wiley & Sons, New York, 1989; Kay, M. A. et al, 2001 *Nat. Medic.*, 7(1):33 to 40; and Walther W. and Stein U., 2000 *Drugs*, 60(2):249 to 71). In one embodiment of this invention the vector is a recombinant AAV carrying a CEP290 fragment cDNA driven by a promoter that expresses the product of the CEP290 nucleic acid sequence in selected cells of the affected subject. Methods for assembly of the recombinant vectors are well-known (see, e.g., International Patent Publication No. WO 00/15822, published Mar. 23, 2000 and other references cited herein). To exemplify the methods and compositions of this invention, the presently preferred vector, a recombinant AAV is described in detail.

In certain embodiments of this invention, the CEP290 nucleic acid sequence, or fragment thereof, is delivered to the selected cells, e.g., photoreceptor cells, in need of treatment by means of a viral vector, of which many are known and available in the art. In certain embodiments, the therapeutic vector is desirably non-toxic, non-immunogenic, easy to produce, and efficient in protecting and delivering DNA into the target cells. In one particular embodiment, the viral vector is an adeno-associated virus vector.

More than 30 naturally occurring serotypes of AAV are available. Many natural variants in the AAV capsid exist, allowing identification and use of an AAV with properties specifically suited for ocular cells. AAV viruses may be engineered by conventional molecular biology techniques, making it possible to optimize these particles for cell specific delivery of RPGR nucleic acid sequences, for minimizing immunogenicity, for tuning stability and particle lifetime, for efficient degradation, for accurate delivery to the nucleus, etc.

The expression of CEP290 functional nucleic acid fragments can be achieved in the selected cells through delivery by recombinantly engineered AAVs or artificial AAV's that contain sequences encoding the desired CEP290 fragment. The use of AAVs is a common mode of exogenous delivery of DNA as it is relatively non-toxic, provides efficient gene transfer, and can be easily optimized for specific purposes. Among the serotypes of AAVs isolated from human or non-human primates (NHP) and well characterized, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include such diseases as cystic fibrosis and hemophilia B. Other AAV serotypes include, but are not limited to, AAV1, AAV3, AAV4, AAV5, AAV6, AAV7, AAV8 and AAV9. See, e.g., WO 2005/033321 for a discussion of various AAV serotypes, which is incorporated herein by reference. Still other modified AAV8 sequences are described in U.S. patent application No. 61/762,775, filed Feb. 8, 2013, incorporated by reference herein. For use in photoreceptor cells, a modified AAV 8_b is a useful vector, among others.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 a useful pseudotyped vector. In another preferred embodiment, the AAV is AAV2/8. See, Mussolino et al, cited above.

In one embodiment, the vectors useful in compositions and methods described herein contain, at a minimum, sequences encoding a selected AAV serotype capsid, e.g., an AAV8 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV8 origin. Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199, which is incorporated by reference herein.

A suitable recombinant adeno-associated virus (AAV) is generated by culturing a host cell which contains a nucleic acid sequence encoding an adeno-associated virus (AAV) serotype capsid protein, or fragment thereof, as defined herein; a functional rep gene; a minigene composed of, at a minimum, AAV inverted terminal repeats (ITRs) and a RPGR nucleic acid sequence; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

Most suitably, such a stable host cell will contain the required component(s) under the control of an inducible promoter. The required component(s) may be under the control of a constitutive promoter. The promoter of the host cell can also be the desired promoter for the vector used in the therapeutic compositions, and may depend upon the selected cell which is ultimately to be treated. Examples of suitable inducible and constitutive or cell/tissue specific promoters are provided herein, in the discussion below of regulatory elements suitable for use with the transgene, i.e., a functional fragment of CEP290. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfers the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, 1993 *J. Virol.*, 70:520 to 532 and U.S. Pat. No. 5,478,745, among others. These publications are incorporated by reference herein.

Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9 or other known and unknown AAV serotypes. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

The desired AAV minigene is composed of, at a minimum, a CEP290 functional fragment nucleic acid sequence (the transgene, e.g., such as the fragment of SEQ ID NO: 5), as described herein, and its regulatory sequences, and 5' and 3' AAV inverted terminal repeats (ITRs). In one embodiment, the ITRs of AAV serotype 2 are used. In another embodiment, the ITRs of AAV serotype 5 or 8 are used. However, ITRs from other suitable serotypes may be selected. It is this minigene which is packaged into a capsid protein and delivered to a selected host cell.

The Regulatory Sequences

The regulatory sequences include conventional control elements which are operably linked to the CEP290 gene fragment or minigene in a manner which permits its transcription, translation and/or expression in a selected cell transfected with the vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters, are known in the art and may be utilized.

The regulatory sequences useful in the constructs of the present invention may also contain an intron, desirably located between the promoter/enhancer sequence and the gene. One desirable intron sequence is derived from SV to 40, and is a 100 bp mini-intron splice donor/splice acceptor referred to as SD-SA. Another suitable sequence includes the woodchuck hepatitis virus post-transcriptional element. (See, e.g., L. Wang and I. Verma, 1999 Proc. Natl. Acad. Sci., USA, 96:3906 to 3910). PolyA signals may be derived from many suitable species, including, without limitation SV-40, human and bovine.

Another regulatory component of the rAAV useful in the method of the invention is an internal ribosome entry site (IRES). An IRES sequence, or other suitable systems, may be used to produce more than one polypeptide from a single gene transcript. An IRES (or other suitable sequence) is used to produce a protein that contains more than one polypeptide chain or to express two different proteins from or within the same cell. An exemplary IRES is the poliovirus internal ribosome entry sequence, which supports transgene expression in photoreceptors, RPE and ganglion cells. Preferably, the IRES is located 3' to the transgene in the rAAV vector.

The selection of the promoter to be employed in the rAAV may be made from among a wide number of constitutive or inducible promoters that can express the CIP290 functional fragment transgene in the selected cell. In another embodiment, the promoter is cell-specific. The term "cell-specific" means that the particular promoter selected for the recombinant vector can direct expression of the selected transgene in a particular cell type.

In an embodiment in which the selected cell is a mammalian photoreceptor, the regulatory sequence comprises a promoter that expresses the product of the CEP290 fragment in mammalian photoreceptors. In one embodiment, the promoter is specific for expression of the transgene in photoreceptor cells. In another embodiment, the promoter is specific for expression in the rods and cones. In another embodiment, the promoter is specific for expression in the rods. In another embodiment, the promoter is specific for expression in the cones. In another embodiment, the promoter is specific for expression of the transgene in RPE cells. In another embodiment, wherein the selected cells is a mammalian cell is a kidney cell, brain cell or olfactory epithelium.

Suitable promoters for expression in photoreceptors may be selected from the rhodopsin promoter, the rhodopsin kinase promoter (51), the RPGTPase regulator (RPGR) promoter, the IRBP promoter, the GRK1 promoter. Alternatively, the promoter may be a constitutive promoter such as a chicken beta actin promoter, a chicken beta actin promoter with a cytomegalovirus enhancer, or modifications thereof, such as modification to shorten the length of the promoter.

In an embodiment in which the selected cell is a mammalian kidney cell, the regulatory sequence comprises a promoter that expresses the product of the CEP290 fragment in mammalian kidney cells. In an embodiment in which the selected cell is a mammalian brain cell or neuron of the CNS, the regulatory sequence comprises a promoter that expresses the product of the CEP290 fragment in mammalian CNS or brain cells. In an embodiment in which the selected cell is a mammalian bone cell, the regulatory sequence comprises a promoter that expresses the product of the CEP290 fragment in mammalian bone cells. In an embodiment in which the selected cell is a mammalian mucosal epithelial cell, such as olfactory epithelial cells, the regulatory sequence comprises a promoter that expresses the product of the CEP290 fragment in mammalian epithelial cells. Still other cellular targets suitable for expression of the CEP290 nucleic acid functional fragments may direct selection of the promoter.

The promoter may be derived from any species. In another embodiment, the promoter is the human G-protein-coupled receptor protein kinase 1 (GRK1) promoter (Genbank Accession number AY327580). In another embodiment, the promoter is a 292 nt fragment (positions 1793 to 2087) of the GRK1 promoter (See also, Beltran et al, Gene Therapy 2010 17:1162-74, which is hereby incorporated by reference herein). In another preferred embodiment, the promoter is the human interphotoreceptor retinoid-binding protein proximal (IRBP) promoter. In one embodiment, the promoter is a 235 nt fragment of the hIRBP promoter. In another embodiment, promoter is the native promoter for the gene to be expressed. In one embodiment, the promoter is the RPGR proximal promoter (Shu et al, IOVS, May 2012, which is incorporated by reference herein). Other promoters useful in the invention include, without limitation, the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, July 2011, 18(7):637 to 45); the alpha-subunit of cone transducin (Morrissey et al, BMC Dev, Biol, January 2011, 11:3); beta phosphodiesterase (PDE) promoter; the retinitis pigmentosa (RP 1) promoter (Nicord et al, J. Gene Med, December 2007, 9(12):1015-23); the NXNL2/NXNL1 promoter (Lambard et al, PLoS One, October 2010, 5(10):e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-39)). Each of these documents is incorporated by reference herein. In one embodiment, the promoter is of a small size, under 1000 bp, due to the size limitations of the AAV vector. In another embodiment, the promoter is under 400 bp.

Examples of constitutive promoters useful in the invention include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the chicken β-actin (CBA) promoter, the phosphoglycerol kinase (PGK) promoter, the EF1promoter (Invitrogen), and the immediate early CMV enhancer coupled with the CBA promoter (Beltran et al, Gene Therapy 2010 cited above).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only.

Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Other types of inducible promoters which may be useful in this context are those which are regulated by a specific physiological state, e.g., temperature, acute phase, a particular differentiation state of the cell, or in replicating cells only. Any type of inducible promoter which is tightly regulated and is specific for the particular target ocular cell type may be used.

Other regulatory sequences useful in the invention include enhancer sequences. Enhancer sequences useful in the invention include the IRBP enhancer (Nicord 2007, cited above), immediate early cytomegalovirus enhancer, one derived from an immunoglobulin gene or SV40 enhancer, the cis-acting element identified in the mouse proximal promoter, etc.

Selection of these and other common vector and regulatory elements are conventional and many such sequences are available. See, e.g., Sambrook et al, and references cited therein at, for example, pages 3.18 to 3.26 and 16.17 to 16.27 and Ausubel et al., Current Protocols in Molecular Biology, John Wiley & Sons, New York, 1989). Of course, not all vectors and expression control sequences will function equally well to express all of the transgenes of this invention. However, one of skill in the art may make a selection among these, and other, expression control sequences without departing from the scope of this invention.

The Pharmaceutical Carrier and Pharmaceutical Compositions

The compositions of the present invention containing the recombinant viral vector, e.g., AAV, containing the desired transgene and cell-specific promoter for use in the selected target cells, e.g., photoreceptor cells for treatment of LCA, as detailed above is preferably assessed for contamination by conventional methods and then formulated into a pharmaceutical composition intended for a suitable route of administration. Still other compositions containing the desired CEP290 fragment, e.g., naked DNA or as protein, may be formulated similarly with a suitable carrier. Such formulation involves the use of a pharmaceutically and/or physiologically acceptable vehicle or carrier, particularly directed for administration to the target cell. In one embodiment, carriers suitable for administration to the photoreceptor cells of the eye include buffered saline, an isotonic sodium chloride solution, or other buffers, e.g., HEPES, to maintain pH at appropriate physiological levels, and, optionally, other medicinal agents, pharmaceutical agents, stabilizing agents, buffers, carriers, adjuvants, diluents, etc.

For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In other embodiments, e.g., compositions containing the CEP290 protein or amino acid, e.g., the single reading frame protein of SEQ ID NO: 6, the pharmaceutical compositions include a surfactant. Useful surfactants, such as Pluronic F68 ((Poloxamer 188), also known as Lutrol® F68) may be included with the vectored CEP290 as they prevent AAV from sticking to inert surfaces and thus ensure delivery of the desired dose.

As an example, one illustrative composition designed for the treatment of LCA comprises a recombinant adeno-associated vector carrying a nucleic acid sequence encoding a fragment of the CEP290 gene lacking at least one of its N-terminal and C-terminal inhibitory regions, under the control of regulatory sequences which express the product of said gene in a photoreceptor cell of a mammalian subject, and a pharmaceutically acceptable carrier. In one embodiment, the AAV is AAV8b. In another embodiment, the AAV is AAV 2/5. In another embodiment, the CEP290 nucleic acid fragment is any of the fragments described above or one or more of the fragments spliced together or otherwise administered together. One such combination is the mini-gene of SEQ ID NO: 5. The carrier is isotonic sodium chloride solution and includes a surfactant Pluronic F68.

In yet another exemplary embodiment, the composition comprises a recombinant AAV2/5 pseudotyped adeno-associated virus carrying a nucleic acid sequence encoding aa 1695 to 1965 of CEP290, the nucleic acid sequence under the control of a rhodopsin kinase promoter which directs expression of the product of said gene in said photoreceptor cells, wherein the composition is formulated with a carrier and additional components suitable for subretinal injection.

In yet another exemplary embodiment, the composition comprises simply unvectored naked minigene CEP290 or other fragments or spliced variant of CEP290 having the functions of natural or wildtype CEP290 formulated with a carrier.

Methods of Treatment/Prophylaxis

The compositions described above are useful in methods of treating a mammalian subject having a disease associated with a CEP290 mutation. These methods comprise administering to a subject in need thereof subject an effective concentration of a composition of any of those described herein.

In one illustrative embodiment, such a method is provided for preventing, arresting progression of or ameliorating vision loss associated with Lebers Congenital Amaurosis in a subject, said method comprising administering to a mammalian subject in need thereof an effective concentration of a composition comprising a recombinant adeno-associated virus (AAV) carrying a nucleic acid sequence encoding a fragment of the CEP290 gene lacking at least one of its N-terminal and C-terminal inhibitory regions, under the control of regulatory sequences which express the product of said gene in a photoreceptor cell of a mammalian subject, and a pharmaceutically acceptable carrier.

By "administering" as used in the methods means delivering the composition to the target selected cell based on the disease caused by CEP290 mutation or defect, and on the selected cell. For example, in one embodiment, the method involves delivering the composition by subretinal injection to the photoreceptor cells or other ocular cells. In another embodiment, intravitreal injection to ocular cells or injection via the palpebral vein to ocular cells may be employed. In another embodiment, the method involves delivering the composition via retrograde urethral injection to the kidney.

In still another embodiment, the method involves delivering the composition by intra-ventricular or intra-cerebral injection to the brain. In yet a further embodiment, the method involves topically delivering the composition to nasal epithelium. Still other methods of administration may be selected by one of skill in the art given this disclosure.

Furthermore, in certain embodiments of the invention it is desirable to perform non-invasive retinal imaging and functional studies to identify areas of retained photoreceptors to be targeted for therapy. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc. In view of the imaging and functional studies, in some embodiments of the invention one or more injections are performed in the same eye in order to target different areas of retained photoreceptors.

For use in these methods, the volume and viral titer of each injection is determined individually, as further described below, and may be the same or different from other injections performed in the same, or contralateral, eye, where the disease is LCA. In another embodiment, a single, larger volume injection is made in order to treat the entire eye. Where the diseases are related to CEP290 expression or defect in another organ, the dosages, administrations and regimens may be determined by the attending physician given the teachings of this specification.

In one embodiment, the volume and concentration of the rAAV composition is selected so that only the certain regions of photoreceptors is impacted. In another embodiment, the volume and/or concentration of the rAAV composition is a greater amount, in order reach larger portions of the eye. Similarly dosages are adjusted for administration to other organs.

An effective concentration of a recombinant adeno-associated virus carrying a nucleic acid sequence encoding the CEP290 nucleic acid functional fragment or minigene under the control of the selected promoter sequence ranges between about $10^8$ and $10^{13}$ vector genomes per milliliter (vg/mL). The rAAV infectious units are measured as described in S. K. McLaughlin et al, 1988 J. Virol., 62:1963. In another embodiment, the concentration ranges between $10^9$ and $10^{13}$ vector genomes per milliliter (vg/mL). In another embodiment, the effective concentration is about $1.5 \times 10^{11}$ vg/mL. In one embodiment, the effective concentration is about $1.5 \times 10^{10}$ vg/mL. In another embodiment, the effective concentration is about $2.8 \times 10^{11}$ vg/mL. In yet another embodiment, the effective concentration is about $1.5 \times 10^{12}$ vg/mL. In another embodiment, the effective concentration is about $1.5 \times 10^{13}$ vg/mL. It is desirable that the lowest effective concentration of virus be utilized in order to reduce the risk of undesirable effects, such as toxicity, and other issues related to administration to the eye, e.g., retinal dysplasia and detachment. Still other dosages in these ranges or in other units may be selected by the attending physician, taking into account the physical state of the subject, preferably human, being treated, including the age of the subject; the composition being administered, e.g., viral vector, AAV, naked DNA or protein-containing; and the particular CEP-290-related disorder, e.g., LCA, Joubert syndrome, Senior Løken Syndrome, or Meckel-Grüber syndrome; the targeted cell or organ type, and the degree to which the disorder, if progressive, has developed.

The composition may be delivered in a volume of from about 50 µL to about 1 mL, including all numbers within the range, depending on the size of the area to be treated, the viral titer used, the route of administration, and the desired effect of the method. In one embodiment, the volume is about 50 µL. In another embodiment, the volume is about 70 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 250 µL. In another embodiment, the volume is about 300 µL. In another embodiment, the volume is about 450 µL. In another embodiment, the volume is about 500 µL. In another embodiment, the volume is about 600 µL. In another embodiment, the volume is about 750 µL. In another embodiment, the volume is about 850 µL. In another embodiment, the volume is about 1000 µL.

The invention provides various methods of preventing, treating, arresting progression of or ameliorating the CEP290-related diseases or disorders, exemplified by LCA, including ocular diseases and retinal changes associated therewith. Such treatment can treat or prevent the advanced of loss of photoreceptor structure or function and blindness associated with LCA caused by a defect in CEP290. The expression of the functional fragment of CEP290 in the targeted cell can result in improvement of the subject's vision or an arrest of vision loss.

In another embodiment, the invention provides a method to prevent, or arrest photoreceptor function loss, or increase photoreceptor function in the subject. Photoreceptor function may be assessed using the functional studies described herein, e.g., ERG or perimetry, which are conventional in the art. As used herein "photoreceptor function loss" means a decrease in photoreceptor function as compared to a normal, non-diseased eye or the same eye at an earlier time point. As used herein, "increase photoreceptor function" means to improve the function of the photoreceptors or increase the number or percentage of functional photoreceptors as compared to a diseased eye (having the same ocular disease), the same eye at an earlier time point, a non-treated portion of the same eye, or the contralateral eye of the same patient.

For each of the described methods, the treatment may be used to prevent the occurrence of further damage or to rescue tissues or organ, e.g., eyes in a subject with LCA, having mild or advanced disease. As used herein, the term "rescue" means to prevent progression of the disease, e.g., to total blindness with LCA, prevent spread of damage to uninjured photoreceptor cells or to improve damage in injured photoreceptor cells.

Thus, in one embodiment, the composition is administered before disease onset. In another embodiment, the composition is administered prior to the initiation of photoreceptor loss. In another embodiment, the composition is administered after initiation of photoreceptor loss. In yet another embodiment, the composition is administered when less than 90% of the photoreceptors are functioning or remaining, as compared to a non-diseased eye.

In another embodiment of the invention, the method includes performing functional and imaging studies to determine the efficacy of the treatment. These studies include ERG and in vivo retinal imaging, as described in U.S. Pat. No. 8,147,823; in co-pending U.S. patent application Nos. 61/670,355 or 61/762,775, incorporated by reference. In addition visual field studies, perimetry and microperimetry, mobility testing, visual acuity, color vision testing may be performed.

In yet another embodiment of the invention, any of the above described methods is performed in combination with another, or secondary, therapy. The therapy may be any now known, or as yet unknown, therapy which helps prevent, arrest or ameliorate CEP290 mutations or defects or any of the effects associated therewith. The secondary therapy can be administered before, concurrent with, or after administration of the rAAV described above.

EXAMPLES

The examples below present evidence that CEP290 directly binds to the ciliary membrane through a highly conserved region in its N-terminus and to microtubules through a domain located near its C terminus CEP290 activity was found to be regulated by autoinhibitory domains located within its N and C-termini, both of which were found to play a critical role in regulating ciliogenesis. Furthermore, the inventors determined that the microtubule-binding domain is completely disrupted in the rd16 mouse LCA model (17), resulting in significant deficits in cilium formation leading to retinal degeneration.

These findings implicate CEP290 both as a key structural component of the ciliary Y-links and as a terminal regulator in the pathway leading to ciliogenesis. This data provides the first evidence of a mechanistic and pathological basis for CEP290-related LCA and related ciliopathies and supports novel therapeutic methods. Restoration of cellular function by the method of this invention can be assessed in an animal model of the appropriate disease caused by CEP290 defect or mutation, such as the restoration of visual function in a subject with a CEP290 defect causing LCA in the rd16 mouse LCA model or canine model of LCA. The use of the exemplary vector can demonstrate that the defect in the mutant dog or other animal model could be corrected by gene delivery. This data allow one of skill in the art to readily anticipate that this method may be similarly used in treatment of XLRP or other types of retinal disease in other subjects, including humans.

Example 1

Materials and Methods

Plasmid Construction

CEP290 truncations were generated by PCR amplification using Gateway® cloning (Invitrogen) compatible primers identified below in Table 1 from a human codon-optimized CEP290 plasmid synthesized by DNA 2.0. Amplified products were directly cloned into pDONR221 (Invitrogen) by Gateway® cloning to generate entry clones. For cell transfection and in vitro transcription and translation assays, entry clones were shuttled into the plasmid pcDNA-DEST53 (Invitrogen) by Gateway® LR clonase reactions to create N-terminally tagged GFP fusions.

TABLE 1 primers used to generate truncation mutants

| Truncation | SEQ ID NO. | Primer | Sequence |
| --- | --- | --- | --- |
| aa 1-2479 | 7 | Forward | GGGGACAAGTTTGTACAAAAAAGCAGGCTTCGAAGGAGATAGAACCATGCCCCCAAACATCAATTGG |
| | 8 | Reverse | GGGGACCACTTTGTACAAGAAAGCTGGGTCCTAATAGATCGGGAAGTTAACAGG |
| aa 580to2479 | 9 | Forward | GGGGACAAGTTTGTACAAAAAAGCAGGCTTCGAAGGAGATAGAACCATGACGGAGAACATAAGCCAAGG |
| | 10 | Reverse | GGGGACCACTTTGTACAAGAAAGCTGGGTCCTAATAGATCGGGAAGTTAACAGG |
| aa1 to580 | 11 | Forward | GGGGACAAGTTTGTACAAAAAAGCAGGCTTCGAAGGAGATAGAACCATGCCCCCAAACATCAATTGG |
| | 12 | Reverse | GGGGACCACTTTGTACAAGAAAGCTGGGTCCTAAAGATTCAGATCCTCGGTAG |
| aa 1-362 | 13 | Forward | GGGGACAAGTTTGTACAAAAAAGCAGGCTTCGAAGGAGATAGAACCATGCCCCCAAACATCAATTGG |
| | 14 | Reverse | GGGGACCACTTTGTACAAGAAAGCTGGGTCCTAATCCCTTTCTTGGATTCCCTGC |
| aa 380-580 | 15 | Forward | GGGGACAAGTTTGTACAAAAAAGCAGGCTTCGAAGGAGATAGAACCATGAAAAACACTTGCATCATTGAGGAC |
| | 16 | Reverse | GGGGACCACTTTGTACAAGAAAGCTGGGTCCTAAAGATTCAGATCCTCGGTAG |
| aa 1-1695 | 17 | Forward | GGGGACAAGTTTGTACAAAAAAGCAGGCTTCGAAGGAGATAGAACCATGCCCCCAAACATCAATTGG |
| | 18 | Reverse | GGGGACCACTTTGTACAAGAAAGCTGGGTCCTAATCCAGCAGATACTTCAAATCC |
| aa 580-1695 | 19 | Forward | GGGGACAAGTTTGTACAAAAAAGCAGGCTTCGAAGGAGATAGAACCATGACGGAGAACATAAGCCAAGG |
| | 20 | Reverse | GGGGACCACTTTGTACAAGAAAGCTGGGTCCTAATCCAGCAGATACTTCAAATCC |

TABLE 1-continued primers used to generate truncation mutants

| Truncation | SEQ ID NO. | Primer | Sequence |
|---|---|---|---|
| aa 1-1966 | 21 | Forward | GGGGACAAGTTTGTACAAAAAAGCAGGCTTCGAAGGAGATAGAACCATGCCCCCAAACATCAATTGG |
|  | 22 | Reverse | GGGGACCACTTTGTACAAGAAAGCTGGGTCCTATGTTTTCAGCTTTCTCTGCAG |
| aa 580-2479 | 23 | Forward | GGGGACAAGTTTGTACAAAAAAGCAGGCTTCGAAGGAGATAGAACCATGACGGAGAACATAAGCCAAGG |
|  | 24 | Reverse | GGGGACCACTTTGTACAAGAAAGCTGGGTCCTAATAGATCGGGAAGTTAACAGG |
| aa 580-1966 | 25 | Forward | GGGGACAAGTTTGTACAAAAAAGCAGGCTTCGAAGGAGATAGAACCATGACGGAGAACATAAGCCAAGG |
|  | 26 | Reverse | GGGGACCACTTTGTACAAGAAAGCTGGGTCCTATGTTTTCAGCTTTCTCTGCAG |
| aa 1695-1966 | 27 | Forward | GGGGACAAGTTTGTACAAAAAAGCAGGCTTCGAAGGAGATAGAACCATGCAGTCCCAGAAGGAGTCAC |
|  | 28 | Reverse | GGGGACCACTTTGTACAAGAAAGCTGGGTCCTATGTTTTCAGCTTTCTCTGCAG |
| aa 1966-2479 | 29 | Forward | GGGGACAAGTTTGTACAAAAAAGCAGGCTTCGAAGGAGATAGAACCATGACAGGCATGACCGTGGAC |
|  | 30 | Reverse | GGGGACCACTTTGTACAAGAAAGCTGGGTCCTAATAGATCGGGAAGTTAACAGG |
| aa 1695-1903 | 31 | Forward | GGGGACAAGTTTGTACAAAAAAGCAGGCTTCGAAGGAGATAGAACCATGCAGTCCCAGAAGGAGTCAC |
|  | 32 | Reverse | GGGGACCACTTTGTACAAGAAAGCTGGGTCCTATTTCTCTTTCATGGGCTTAAGGTC |
| aa 1903-2479 | 33 | Forward | GGGGACAAGTTTGTACAAAAAAGCAGGCTTCGAAGGAGATAGAACCATGACAGGCATGACCGTGGACC |
|  | 34 | Reverse | GGGGACCACTTTGTACAAGAAAGCTGGGTCCTAATAGATCGGGAAGTTAACAGG |

For bacterial expression, entry clones were shuttled into pDest-527 (a gift of Dominic Esposito (Addgene plasmid #11518)) to create N-terminally-tagged 6×His fusions. For lentivirus production, entry clones were shuttled into pLX-nGFP, a modified version of pLX302 (a gift of David Root (Addgene plasmid #25896)), to create N-terminally-tagged GFP fusion lentivirus production plasmids. pLXnGFP was created by the replacement of the gateway cassette of pLX302 with an eGFP cassette containing an EcoR V site just downstream of the eGFP ORF by BsrGI digestion and ligation. The Gateway A cassette was then inserted into the EcoRV site using the Gateway Conversion Kit (Invitrogen). Restriction digest and DNA sequencing were used to confirm the integrity of each expression construct.

shRNA constructs were created as follows. Three regions of the human CEP290 coding sequence without homology to other transcripts were selected as shRNA targets. Oligonucleotides encoding the target sequence in the context of a DNA hairpin were synthesized, annealed, and ligated into the pSIREN-RetroQ retrovirus vector (Clontech). Efficiency of knockdown was assayed. The mammalian expression vector encoding GFP-fused miniCEP290 was created by the amplification of the miniCEP290 gene by PCR using primers compatible with Gateway® cloning (Invitrogen). Amplified products were cloned into pDONR221 (Invitrogen) by Gateway® cloning to generate entry clones and subsequently shuttled into the plasmid pcDNA-DEST53 (Invitrogen) by Gateway® LR clonase reactions to create N-terminally-tagged GFP fusions.

miniCEP290 Synthesis

The miniCEP290 construct was codon optimized, synthesized, and sequenced by DNA2.0.

Cell Culture and Treatments; Lentivirus Production; Retrovirus Production

Wild type and rd16 mouse primary dermal fibroblasts and human 293T cells were grown in DMEM supplemented with 10% FBS. hTERT RPE to 1 cells were grown in DMEM:F12 supplemented with 10% FBS and 0.075% sodium bicarbonate. All cells were grown at 37° C. in a humidified 5% $CO_2$ atmosphere. All transfections were performed with FuGENE 6 reagent (Promega) according to the manufacturer's protocol. Cells were induced to form primary cilia by serum starvation with OptitoMEM I (Invitrogen) for 48 to 72 hours.

Lentiviral vectors were produced by transfection of 80% confluent 293T cells grown in T25 culture flasks with 1 µg of lentivirus construct, 750 ng of PsPAX2 packaging plasmid, and 250 ng of pMD2.G envelope plasmid using FuGENE6. Media was replaced after 24 hours, and lentiviral supernatants were harvested at 48 and 72 hours after transfection, combined, filtered through a 0.45 µm filter, and snap-frozen at to 80° C. For lentivirus transduction, hTERT RPE-1 cells were plated in 6 well plates in media containing 8 µg/mL polybrene. 0.5 mL of filtered media containing the appropriate lentivirus particles was added to each well. 24 hours after transduction cells were switched to media containing 10 µg/mL puromycin and maintained in selective media from that point on. All experiments carried out on lentivirus transduced cells were performed 10 days post transduction.

Retroviral vectors were produced by transfection of 80% confluent 293T cells in 100 mm culture dishes with 10 µg of retrovirus construct and 10 µg of pCL10A1 packaging plasmid. Media was replaced after 24 hours, and retroviral supernatants were harvested at 48 and 72 hours, combined, filtered through a 0.45 µm filter, and snap-frozen at −80° C. For retrovirus transduction, hTERT RPE-1 cells were plated in media containing 8 µg/mL polybrene. Filtered media containing the appropriate retroviral particles was added and 24 hours after transduction cells were switched to selective media containing 10 µg/mL puromycin.

Primary Dermal Fibroblast Isolation

Primary dermal fibroblasts were isolated by washing sections of neonatal mouse skin in 70% ethanol followed by 5 washes in PBS. The skin was minced and applied to the bottom of a culture vessel, covered with DMEM supplemented with 10% FBS, penicillin, and streptomycin, and incubated at 37° C. in a humidified 5% CO2 atmosphere. One week after harvesting the skin was removed and discarded and fibroblasts were passaged into a larger vessel.

Antibodies, Immunofluorescence, and Immunoblotting

Antibodies used in this study were rabbit anti-human CEP290 (Abcam, ab105383), rabbit anti-mouse Cep290 (Abcam, ab128231), mouse anti-α tubulin (Abcam, AB7291), rabbit anti-pericentrin (Abcam, AB4448), mouse anti-GFP (Roche 11 814 460 001), mouse anti-Bovine serum albumin (Thermo, MA5 to 15238), rabbit anti-6×His (Abcam, AB1187), rabbit anti-GAPDH (Sigma, SAB2103104), mouse anti-Na/K ATPase α-1 (Novus, NB300 to 146), mouse anti-Lamin A/C (Sigma, SAB4200236), mouse anti-Acetylated α-tubulin (Sigma, T7451), rabbit anti-LAMP2 (Novus, NBP1 to 71692), rabbit anti-Annexin A2 (Cell Signaling, 8235), rabbit anti-ARL13B (Proteintech, 17711-1-AP), HRP-conjugated goat anti-mouse (GE, NA931V), HRP-conjugated goat anti-rabbit (GE, NA934V), Cy5 conjugated goat anti-rabbit (KPL, 072-02-15-06), and AlexaFluor 594-conjugated goat anti-mouse (Invitrogen, A1100S).

For immunofluorescence, cells were grown in chamber slides and fixed with 3% PFA in PBS for 20 minutes at 37° C. Cells were permeabilized with 1% Triton X-100 in PBS for 5 minutes, and blocked in 2% BSA in PBS for 30 minutes prior to incubation with primary antibody. Secondary antibodies used were donkey anti-mouse or anti-rabbit, conjugated to Cy5 or AlexaFluor 594. Slides were mounted in mounting medium containing DAPI. Confocal imaging was performed with an LSM510 META NLO laser scanning confocal on a Zeiss Axiovert 200M inverted microscope using a Plan-Apo 63×/1.4 oil objective and the LSM510 4.2 software. Laser lines used were 488 nm (for green labeling, from argon laser), 543 nm (for red labeling, HeNe laser), 633 nm (for Cy5 channel, HeNe laser), and 740 nm (for DAPI channel, from a Coherent Chameleon tunable two photon laser). For normal fluorescence microscopy, slides were imaged using an Axio Imager.M2 microscope using an either EC Plan-Neofluar 40×/0.75 M27 or an EC Plan-Neofluar 63×/1.25 Oil M27 objective and captured using an AxioCamMR3 camera and the AxioVs40 software, version 4.8.2.0. Primary cilium length was measured using the same AxioVs40 software.

For immunoblotting, samples were subjected to SDS-PAGE and transferred to nitrocellulose membrane using standard techniques. Membranes were blocked in 5% nonfat milk for 1 hour at room temperature and subsequently incubated in primary antibody overnight at 4° C. Membranes were washed three times with PBST (0.1% TweeN-20 in PBS) and incubated with HRP-conjugated secondary antibody for 1 hour at room temperature. Membranes were washed three times with PBST, developed using ECL2 reagent (Pierce), and scanned on a Typhoon 9400 instrument (GE) Immunoblots were quantified by densitometry using ImageJ 1.44p.

Membrane Flotation, Membrane Protein Fractionation, and Vesicle Immunoprecipitation Cultured cells were washed three times with ice cold PBS. Cells were then resuspended in a 250 mM Sucrose solution containing 4 mM Immidazole and a protease inhibitor cocktail and passaged through a 25G needle 20 times to rupture the plasma membrane. The resulting lysate was centrifuged at 1,000×g for 10 minutes at 4° C. to pellet nuclei and unlysed cells and the resulting post-nuclear supernatant was centrifuged at 100,000×g for 60 minutes at 4° C. to pellet the membrane-enriched fraction. Membrane flotation was performed by resuspending the membrane-enriched fraction in 250 µL of 80% sucrose in PBS. This solution was added to the bottom of a 2 mL centrifuge tube, overlaid with 1.5 mL of 50% sucrose in PBS, and in turn overlaid with 250 µL of 5% sucrose in PBS. Sucrose gradients were centrifuged at 100,000×g for 16 hours at 4° C. to induce the membrane and membrane associated proteins to float to the top of the gradient. Equal fractions were subsequently taken from the top to the bottom of the gradient and analyzed by western blotting as indicated. Peripheral membrane proteins were extracted from membrane preparations by resuspending and incubating the membrane-enriched fraction of cultured cells in a high pH buffer (100 nM Na2CO3, pH 11.3) for 30 minutes at 4° C. The remaining membranes were pelleted at 100,000×g for 60 minutes at 4° C. and the resulting supernatant was saved as the peripheral membrane fraction. Integral membrane proteins were subsequently extracted by resuspending and incubating the resulting membrane pellet in 4% TritoN-X100 in PBS for 30 minutes at 4° C. Both fractions were analyzed by immunoblotting for the CEP290 truncations being tested and for the indicated fractionation controls. Vesicle immunoprecipitation was performed on post-nuclear supernatants of hTERT-RPE1 cells expressing various CEP290 truncations.

A sample of the total post nuclear extract was saved as the input fraction. Protein G Dynabeads (Invitrogen) were washed and incubated with 2 µg of anti-ARL13B antibody for 20 minutes at room temperature, magnetically collected, and washed three times with PBS. 350 µL of post-nuclear supernatant was added to the antibody-dynabead complex and incubated with gentle agitation for 20 minutes at room temperature. The beads and immunoprecipitated complexes were magnetically collected and washed three times with PBS. A sample of the unbound fraction was saved and the immunoprecipitated material was eluted by resuspension in 4×SDS PAGE sample buffer. Samples were analyzed by immunoblotting.

Subcellular Fractionation

Subcellular fractionation was performed using the QProteome Cell Compartment kit (Qiagen) according to the supplied protocol. All fractions were analyzed by immunoblotting for the CEP290 truncations being tested and for the indicated fractionation controls and quantified by densitometric analysis using ImageJ 1.44p.

Recombinant Protein Expression and Purification

6xHis tagged CEP290 truncation M and N were expressed from pDest-527 in *E. coli* BL21(DE3)pLysS (Invitrogen) and purified using the Ni-NTA Fast Start Kit (Qiagen) according to the manufacturer's protocol. Purified protein products were subjected to SDS-PAGE and stained with Coomassie Brilliant Blue to assess purity and determine protein concentration.

Liposome Flotation Assay 100 nm liposomes (total lipid concentration of 5 mg/mL in PBS) with a lipid composition of a 60:40 molar ratio of phosphatidylserine to cholesterol were purchased from Encapsula NanoSciences and used within 2 weeks of their formulation. 20 µL (1.5 µg) of recombinant CEP290 truncation N, or an equivalent amount of BSA, was incubated with 230 µL of liposomes, or an equal volume of PBS alone, at 37° C. for 30 minutes. Each reaction was then mixed 1:1 with a solution of 80% sucrose in PBS and added to the bottom of a 2 mL ultracentrifuge tube. Reactions were overlaid with 1.3 mL of 30% sucrose in PBS, which was in turn overlaid with 200 µL of PBS. Liposomes and liposome associated protein were induced to float to the top of the gradient by centrifugation at 100,000xg for 90 minutes at 30° C. Five 400 µL fractions were taken, starting at the top of sucrose gradient, and equal amounts of each were analyzed by SDS-PAGE and western blotting, probing for either the 6xHis tag or BSA.

In Vitro Transcription and Translation Reactions

Plasmid DNA was transcribed and translated using the TNT T7 reticulocyte lysate system (Promega) according to the manufacturer's protocol.

Microtubule Polymerization

Pure bovine tubulin (Cytoskeleton) was diluted 1:1 in BRB80 buffer (80 mM Pipes, 1 mM $MgCl_2$, 1 mM EGTA, pH 6.8) and cleared of insoluble material by centrifugation at 20,000xg for 10 minutes. The soluble fraction was supplemented with 1 mM GTP and incubated at 37° C. for 15 minutes to polymerize microtubules. The polymerized microtubules were then treated with 10 µM taxol and incubated at room temperature for a further 15 minutes to stabilize the microtubules. Microtubules were then pelleted at 48,000xg for 30 minutes at 30° C. and resuspended in BRB80 supplemented with 1 mM GTP and 10 µM taxol. Microtubules were used within one week of preparation.

Microtubule Binding Assays

Crude TNT T7 reaction products were diluted 1:1 in BRB80 supplemented with 1 mM GTP and 10 µM taxol. The diluted products were then incubated at 30° C. for 30 minutes in either the presence or absence of pure, prepolymerized microtubules. Reactions were then centrifuged through a 40% sucrose cushion at 48,000xg for 30 minutes, the supernatant was collected, and the pellet washed once with warm BRB80 and resuspended in 1xSDS PAGE sample buffer. Both fractions were subjected to SDS-PAGE and transferred to nitrocellulose. The presence of tubulin in the pellets was confirmed by Ponceau staining, and GFP-tagged CEP290 constructs were detected by immunoblotting.

For microtubule binding assays performed on mouse brain homogenate, 0.5 g of mouse brain was mechanically homogenized in 0.5 mL of 1% NP40 in BRB80 buffer containing a protease inhibitor cocktail. The homogenate was cleared of insoluble material by centrifugation at 48,000xg for 30 minutes at 4° C., and the resulting supernatant was either used immediately or snap-frozen at to 80° C. for later use. Homogenates were incubated either at 37° C. for 30 minutes with 1 mM GTP and 10 µM taxol to promote microtubule polymerization, or at 4° C. for 30 minutes to inhibit microtubule polymerization. The resulting reactions were then layered over a 40% sucrose cushion, centrifuged at 48,000xg for 30 minutes to pellet the microtubules and microtubule-associated proteins, and processed as above.

For the direct microtubule binding assay, 1 nM of recombinantly expressed and purified 6xHis tagged CEP290 truncation M was incubated at 30° C. for 30 minutes with increasing amounts of pure, prepolymerized microtubules. Reactions were centrifuged and subjected to SDS-PAGE as above, and tubulin and CEP290 truncation M were detected by Coomassie blue staining.

Bioinformatic Analysis

Figure 2A:
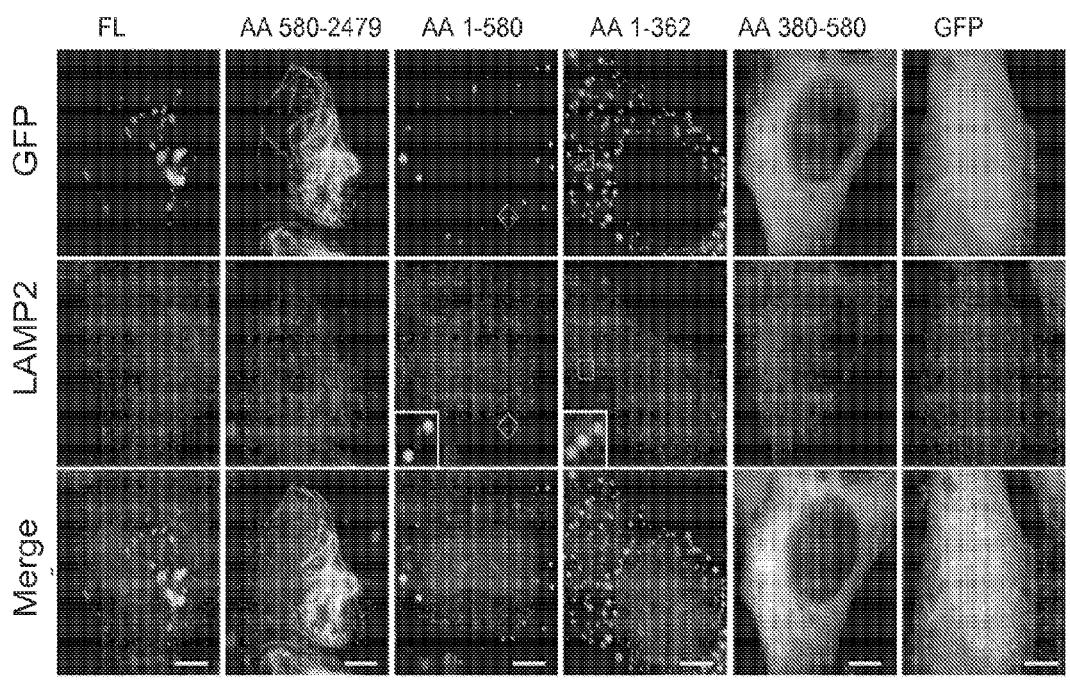
FIGS. 2A to 2E illustrate that CEP290 directly binds membranes in vitro and contains a highly conserved membrane binding amphipathic α-helix.
Figure 2B:
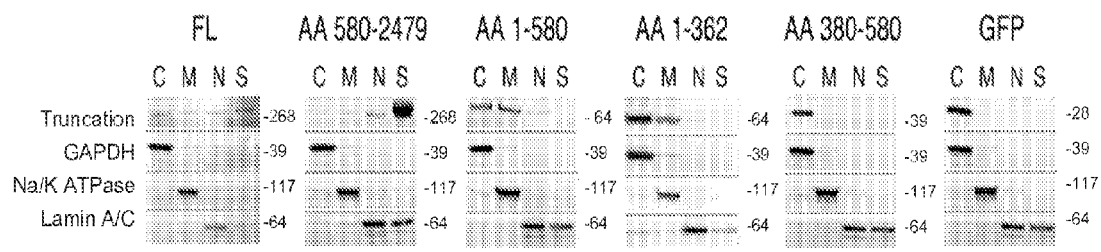
Figure 2C:
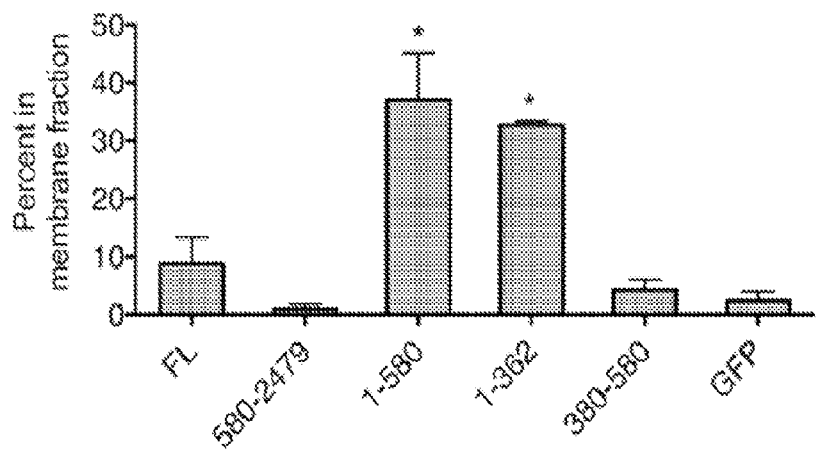
Figure 2D:
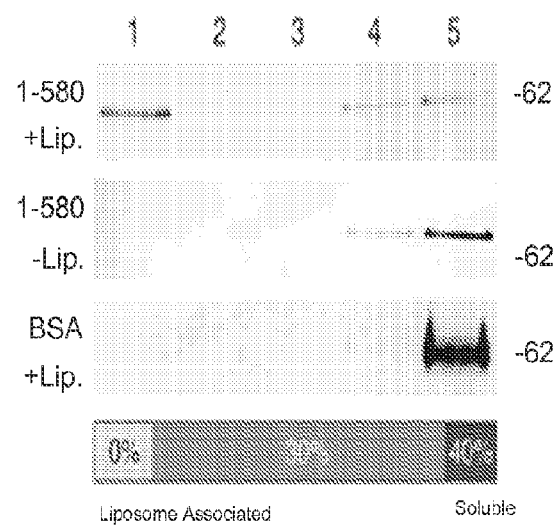
Figure 2E:
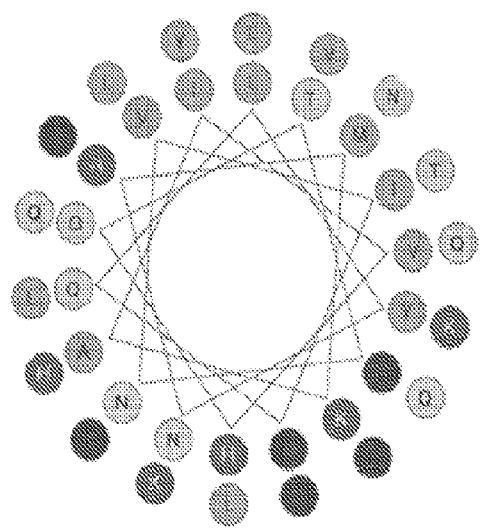

The helical wheel projection in FIG. 2E was adapted from the Helical Wheel Projection applet available at rzlab.ucr.edu. The multiple sequence alignment was adapted from GeneDoc 2.7.000.

Statistical Analysis

The statistical significance of the difference between two means was determined using a two-tailed Student's t-test. The statistical significance of the difference between three or more means was determined using a two-way ANOVA and Tukey's HSD test. Statistical analysis was performed using GraphPad Prism Software 5.0b. p-values <0.05 were considered significant.

Example 2

Cep290 Associates with ARL13B Positive Cellular Vessicles Via its N-Terminus Mutations in the CEP290 gene have been implicated in a variety of human diseases, but their effects on protein function have not yet been characterized. Mutations clustering in particular regions of the gene might be indicative of important functional domains, but no mutational hotspots or functional domains have been identified to date (FIG. 1A). To understand the role CEP290 plays in cilium function, ciliogenesis, and human disease, a structure-function analysis was performed using a panel of truncation constructs spanning the full length of CEP290 in order to identify and define domains of novel functionality.

Figure 1B:
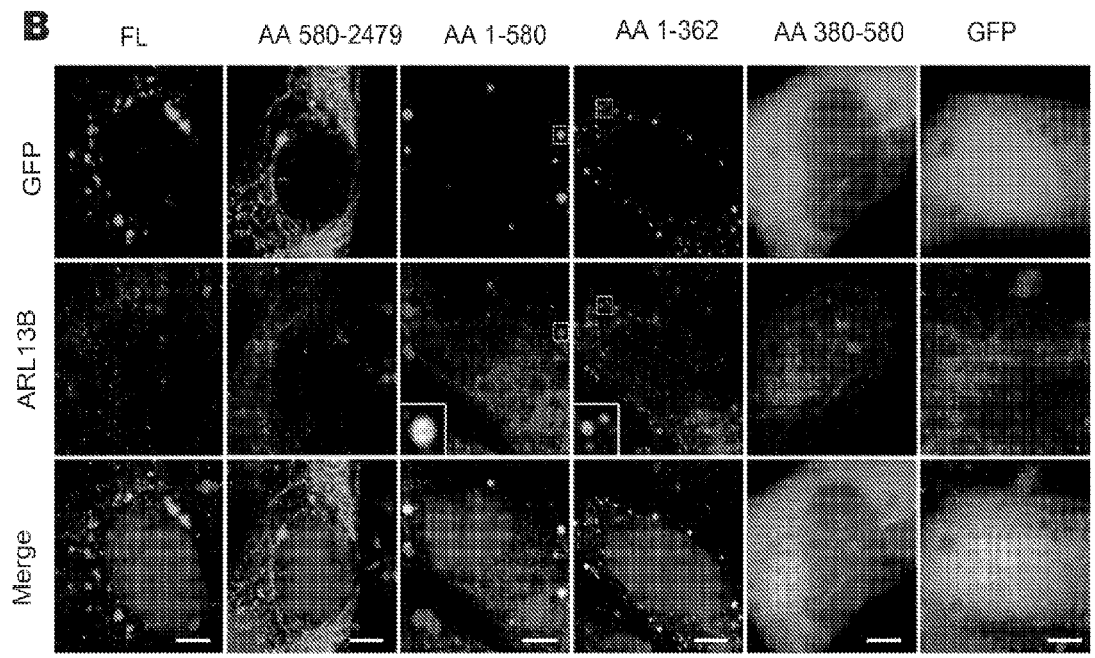

The first two CEP290 truncations displayed distinct localization patterns. When overexpressed as GFP fusion proteins, the N-terminal fragment of CEP290 (spanning aa 1 to 580) showed an exclusively vesicular localization pattern while the C-terminal fragment of CEP290 (from aa 580 to the end of the protein, aa 2479) (SEQ ID NO: 60) showed a striking fibrillar localization pattern (FIG. 1B). Both of these patterns were occasionally observed in cells overexpressing the full length CEP290 construct, but not with the same frequency as in cells expressing the truncations (data not shown).

Two additional truncations of the N-terminal region of the protein were generated to better define the domain responsible for the vesicular localization. The truncation spanning CEP290 aa 1 to 362 showed a vesicular pattern of localization similar to that observed for the complete N-terminal fragment, while the truncation spanning aa 380 to 580 (SEQ ID NO: 61) was present only diffusely throughout the cytoplasm (FIG. 1B). Further truncation of the protein was not effective in resolving its membrane association property beyond aa 1 to 362, implying either that this is the minimum region needed for CEP290 membrane association or that further truncation significantly interferes with protein function.

Figure 1C:
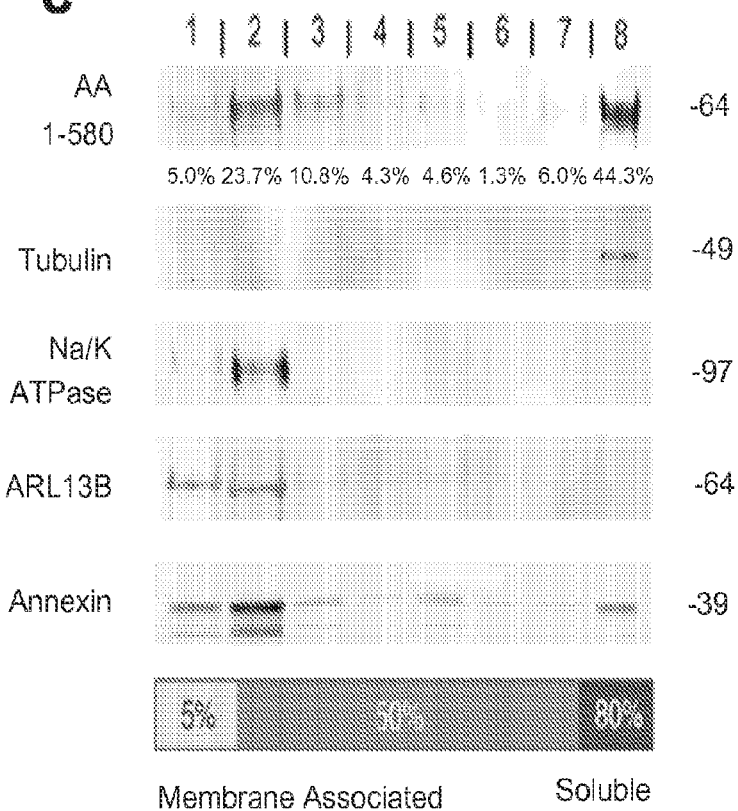
Figure 1D:
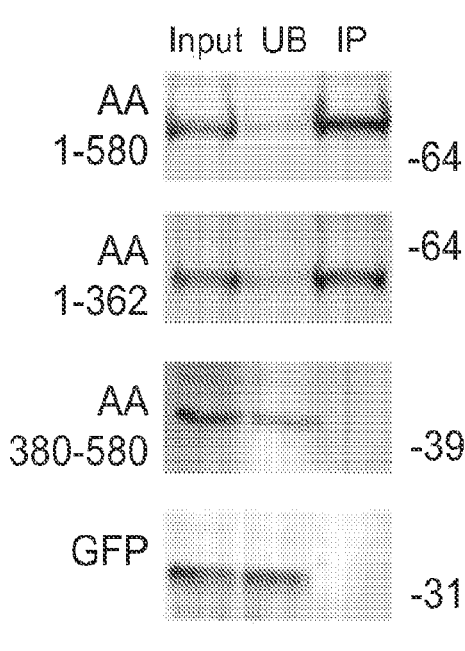

The CEP290-positive vesicles observed by microscopy were found to display robust co-staining with ARL13B (FIG. 1B), a membrane protein important in the trafficking of vesicles to the primary cilium. To biochemically assay this colocalization, detergent free post-nuclear supernatants of cells expressing our CEP290 truncations were prepared and ARL13B positive vesicles were magnetically immunoprecipitated and analyzed by western blotting. Both CEP290 aa 1 to 580 and CEP290 aa 1 to 362 were significantly enriched in the ARL13B immunoprecipitate, while neither CEP290 aa 380 to 580 nor GFP alone were found in significant quantities (FIG. 1D).

Thus, CEP290 aa 1 to 362 were found to be necessary and sufficient to mediate CEP290 localization to ARL13B positive cellular vesicles relevant to primary cilium biology. In only very few cases did the CEP290-positive vesicles exhibit any costaining with LAMP2, a marker of the lysosomal compartment (FIG. 2A), indicating that CEP290 vesicular localization was not an artifact of protein overexpression.

Figure 1E:
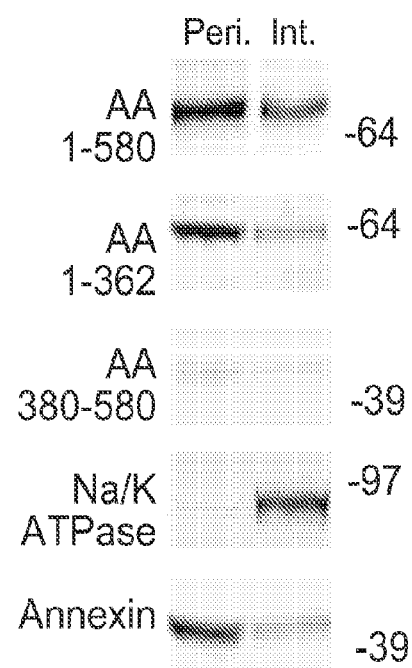

To confirm that the vesicular structures observed by microscopy were truly membranous organelles and not aggregates of overexpressed protein we performed a series of membrane co-flotation assays on cells expressing CEP290 aa 1 to 580. More than ⅓ of total CEP290 aa 1 to 580 was found to co-float in the membrane-associated fractions (FIG. 1C), indicating that a substantial portion of the protein was, in fact, associated with cellular membranes. ARL13B was found to co-float in the same fractions as CEP290 aa 1 to 580, corroborating the colocalization between the two that we had observed by microscopy and co-IP (FIG. 1C). The dual distribution of CEP290 aa 1 to 580 within both the membrane-associated and soluble fractions along with the absence of a signal peptide from CEP290's amino acid sequence was suggestive of peripheral, rather than integral, membrane association. To confirm this, membrane fractions of cells transfected with our CEP290 truncations were prepared and peripheral membrane proteins were eluted from the membrane with a high pH buffer. The remaining integral membrane proteins were subsequently solubilized with detergent. For both CEP290 aa 1 to 580 and aa 1 to 362 the majority of each truncation was found in the peripheral membrane protein fraction (FIG. 1E). This same pattern was observed for the peripheral membrane protein Annexin A2 (36), while the majority of the Na/K ATPase, an integral membrane protein, was found in the integral membrane protein fraction (FIG. 1E). CEP290 aa 380 to 580, on the other hand, was not found in significant amounts in either fraction. Taken together, these data indicate that CEP290 aa 1 to 362 are necessary and sufficient for robust peripheral membrane association.

Example 3

Cep290's Capacity for Membrane Association is Increased by Truncation of its C-Terminus To further investigate CEP290's membrane association, a series of subcellular fractionation experiments on cells expressing each of our CEP290 truncations was performed. The CEP290 truncation spanning aa 580 to 2479 that produced a fibrillar localization pattern by microscopy was found almost exclusively in the cytoskeletal fraction, while truncations lacking this region were completely absent from the cytoskeletal fraction (FIG. 2B). On the other hand, truncations that included CEP290 aa 1 to 362 were again found to be significantly present in the membrane fraction when compared to either GFP alone or our fractionation controls (FIG. 2B). For both CEP290 aa 1 to 580 and aa 1 to 362, roughly 30% of each truncation was found to be associated with cellular membranes (FIG. 2C), demonstrating again that CEP290 aa 1 to 362 are necessary and sufficient for membrane association. Interestingly, a small amount of full length CEP290 was also found in the membrane fraction (FIG. 2B to C). This distribution agrees with what was observed by fluorescence microscopy—specifically, that full length CEP290 occasionally displayed vesicular localization, but to a lesser extent than CEP290 truncations lacking the C-terminus of the protein but containing aa 1 to 362.

Example 4

Cep290 Directly Binds Membranes In Vitro and Contains a Highly Conserved Membrane Binding Amphipathic α-Helix Motif To determine whether CEP290's membrane association was mediated by a direct or indirect membrane interaction a series of liposome co-flotation assays were performed on purified recombinant CEP290 aa 1 to 580. CEP290 aa 1 to 580 associated with liposomes robustly, with a majority of the protein found in the liposome-associated fraction (FIG. 2D). Flotation of the truncation occurred only in the presence of liposomes, and liposome co-flotation was not observed for a control protein, BSA (FIG. 2D). The ability of this region of CEP290 to directly bind liposomes suggests that the observed association between the N-terminus of CEP290 and cellular membranes is mediated by a direct interaction.

Projecting CEP290 aa 1 to 362 onto an α-helical wheel indicated that a segment from aa 257 to 292 was predicted to form a canonical amphipathic α-helix (FIG. 2E). Such helices have been shown to be critical in mediating robust interactions between peripheral membrane proteins and various cellular membranes. Comparing this stretch of the protein across a variety of species, we found the amphipathic helix motif to be very highly conserved. An examination of a sequence alignment of aa257 to 292 from a variety of species shows that where there was divergence in the amino acid sequence from the sources of CEP290 aa 257 to 292 for the following species: *Gallus* SEQ ID NO: 35, *Meleagris*

SEQ ID NO: 36, *Rattus* SEQ ID NO: 37, *Mus* SEQ ID NO: 38, *Pongo* SEQ ID NO: 39, *Macaca* SEQ ID NO: 40, *Homo sapiens* SEQ ID NO: 41, *Felis* SEQ ID NO: 42, *Ailuropoda* SEQ ID NO: 43 and *Danio* SEQ ID NO: 45, there was usually conservation of polarity and charge between the divergent residues. Taken together, these data support that the highly conserved amphipathic helix located within the membrane binding region of CEP290 mediates CEP290's novel membrane binding function.

Example 5

Cep290 AA 1695 to 1966 Mediate Colocalization with Microtubules

CEP290 aa 580 to 2479 appeared both by microscopy and subcellular fractionation to be associated with the cytoskeleton (FIG. 1B, 2A). To further investigate this phenomenon, we constructed a library of additional CEP290 truncations to thoroughly interrogate CEP290's cytoskeletal association (FIG. 3B). Overexpression of these truncations as GFP fusions revealed that those truncations containing CEP290 aa 1695 to 1966, referred to as region M, displayed a fibrillar localization pattern similar to that which was observed for CEP290 aa 580 to 2479 (FIG. 3A, B). The fibrils formed by these CEP290 truncations were noted to co-localize with the microtubule network. Truncations lacking CEP290 region M never display any fibrillar localization (FIG. 3A, B). This along with the fact that CEP290 region M alone showed robust colocalization with the tubulin network implicated CEP290 region M as necessary and sufficient for microtubule co-localization.

Figure 3C:
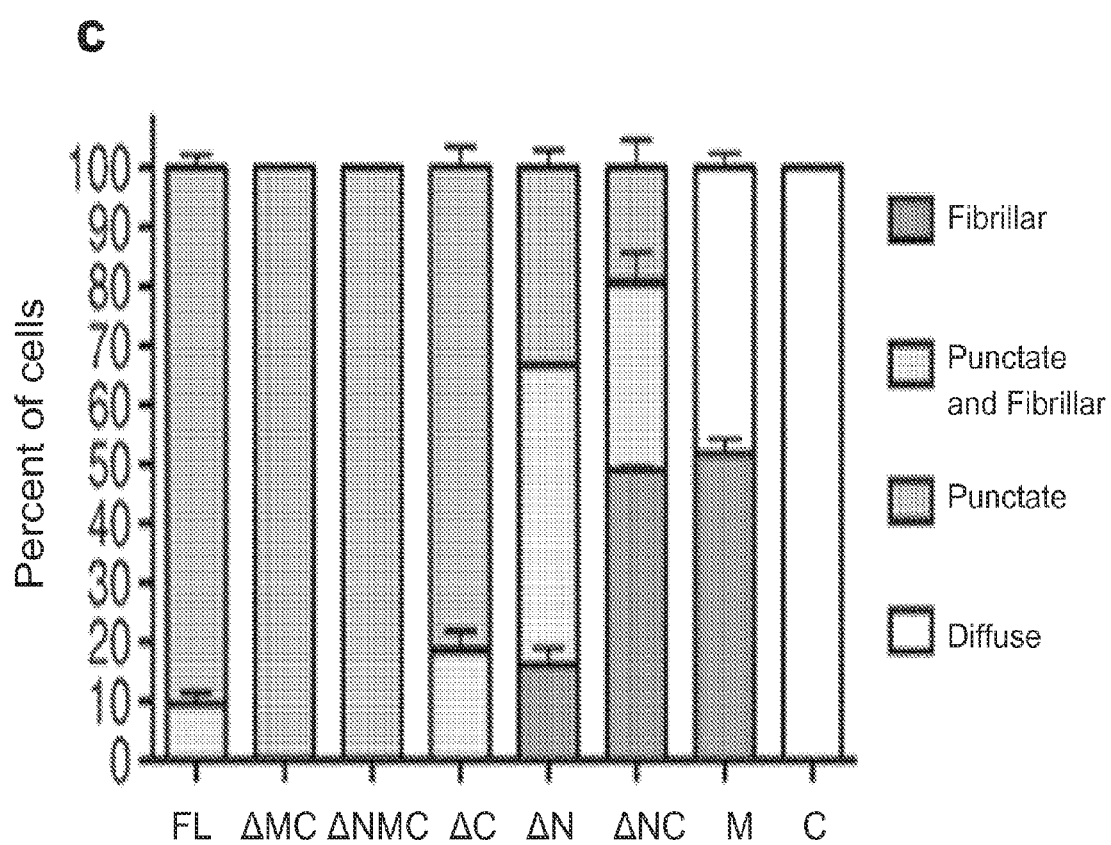

The degree to which different CEP290 truncations displayed a fibrillar localization pattern was found to be dependent upon which regions of the protein were included in the truncation. The full length CEP290 construct was noted to produce a fibrillar localization pattern in only about 10% of transfected cells (FIG. 3C). Truncations lacking either the N- or C-terminus of CEP290, on the other hand, were found to display fibrillar localization in roughly 20% and 60% of transfected cells, respectively. The truncation lacking both termini was found to display a fibrillar localization pattern in nearly 80% of transfected cells. These data indicated that the N- and C-termini of the protein have an inhibitory or regulatory effect on CEP290's microtubule binding ability. All of our truncations displayed co-localization with pericentrin, a marker of the centriole (the normal site of CEP290 localization) (FIG. 3A, insets). Homotypic interactions between endogenous CEP290, present at the centrioles, and our truncations (through CEP290's homo/heterodimerization domains, found within either terminus of the protein (29)) might explain the observed centriolar localization of a number of our truncations. However, those truncations lacking both homo/heterodimerization domains are apparently still capable of localizing to the centriole, implying that multiple regions throughout CEP290 are capable of affecting centriolar localization.

Example 6

Cep290 Microtubule Association Results in Microtubule Acetylation and Bundling

Figure 4A:
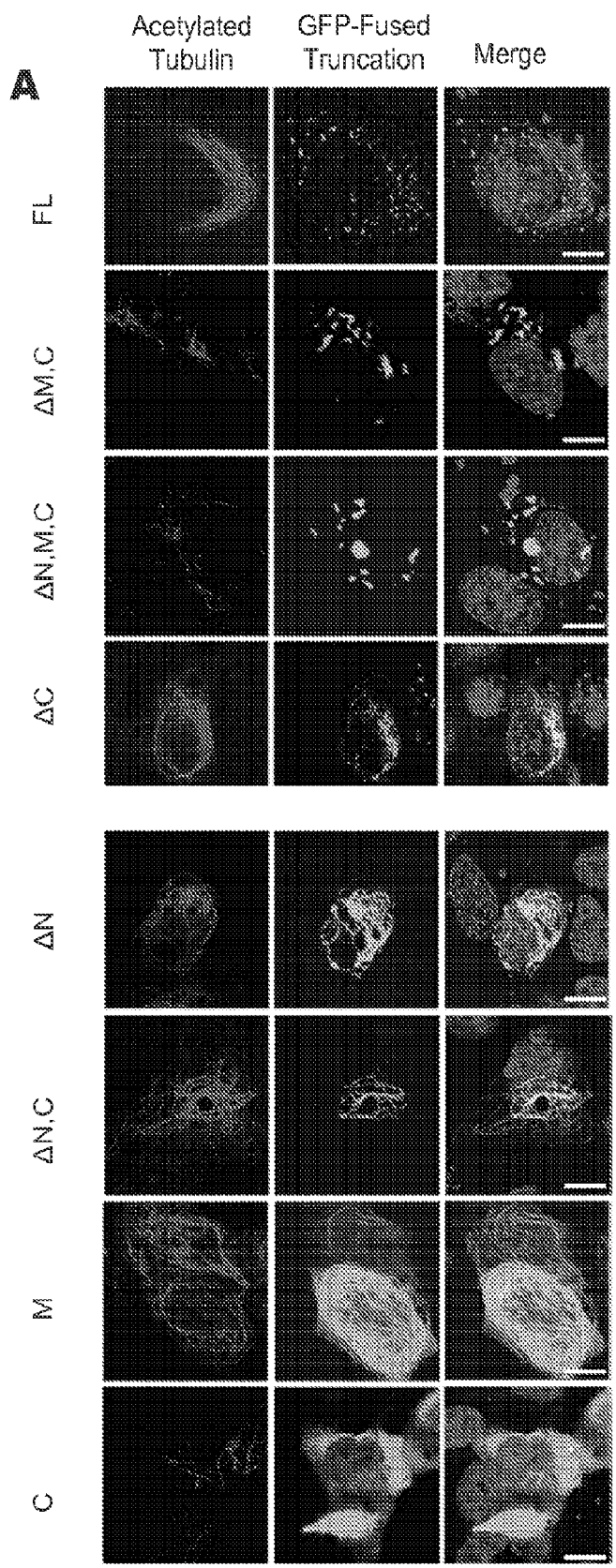
FIGS. 4A to 4F show that CEP290 directly binds to and bundles microtubules via region M, and its N- and C-termini inhibit microtubule binding and bundling.
Figure 4B:
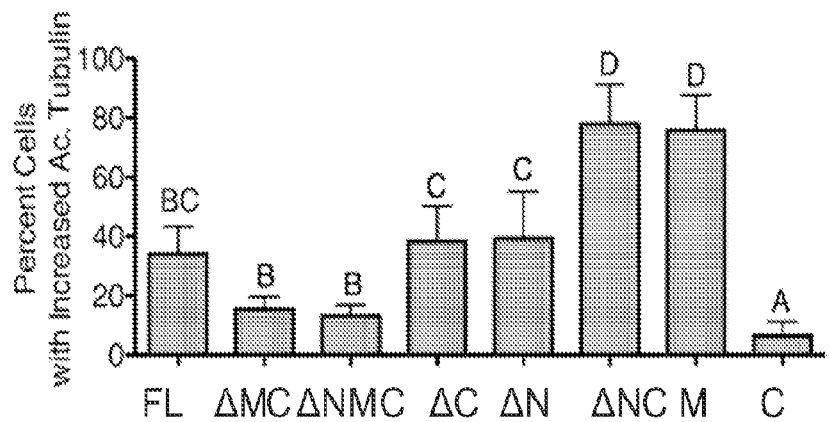

In cells transfected with CEP290 constructs containing region M there was a dramatic increase in the intensity of acetylated α-tubulin staining, with bundles of acetylated microtubules looping throughout the cells (FIG. 4A). These increases were not seen for truncations lacking region M. The degree to which different CEP290 truncations increased the acetylation and bundling of microtubules was dependent upon which regions of the protein were included in the truncation. Full length CEP290 and CEP290 truncations lacking either the N- or C-terminus increased microtubule acetylation and bundling in nearly 40% of transfected cells while CEP290 truncations lacking both the N- and C termini of the protein increased microtubule acetylation and bundling in nearly 75% of cells (FIG. 4B). Less than 15% of cells transfected with truncations lacking region M were noted to have any change in microtubule acetylation or bundling.

Example 7

Cep290 Directly Binds Microtubules In Vitro

Figure 4C:
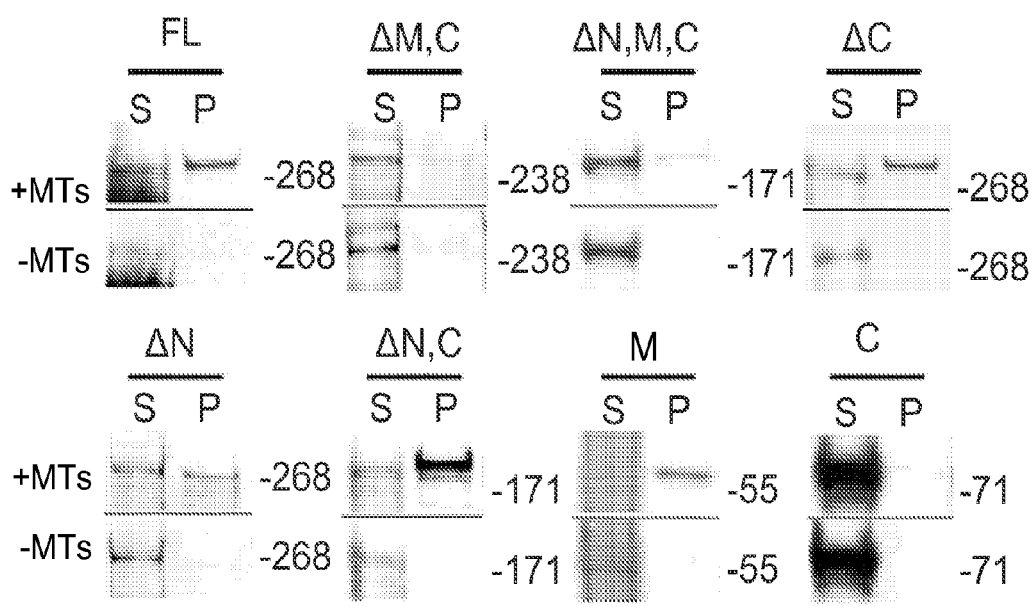
Figure 4D:
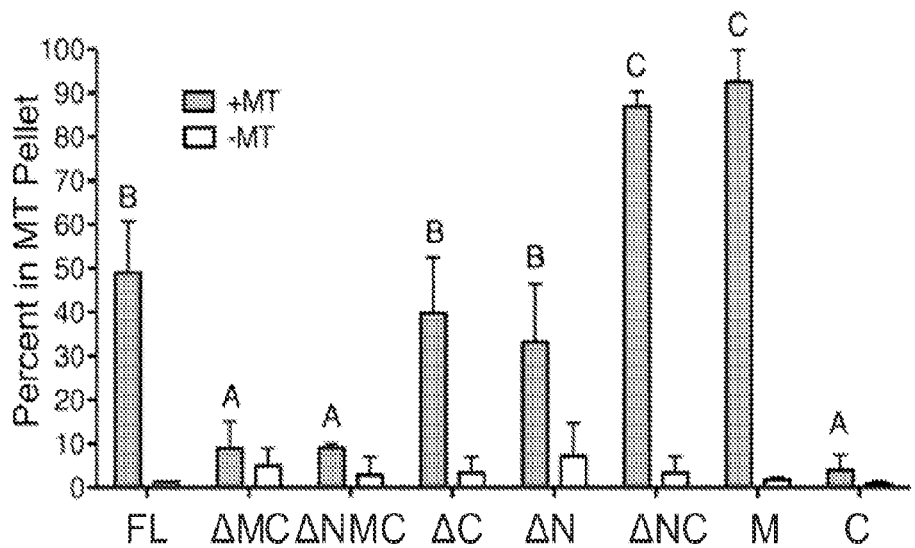
Figure 4E:
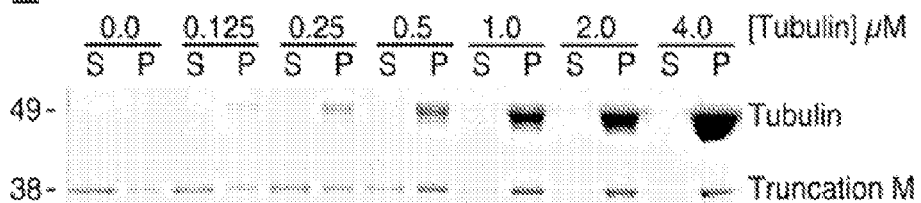
Figure 4F:
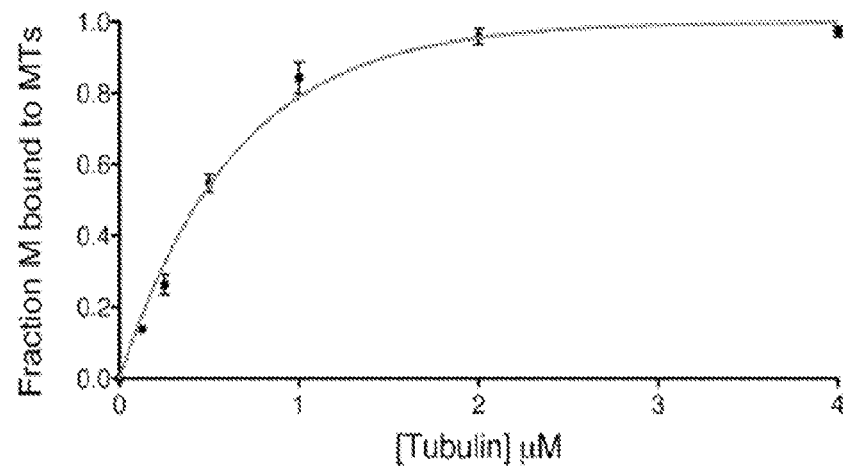

To test whether microtubule co-localization was indicative of an interaction between CEP290 and microtubules, we performed a series of in vitro microtubule co-sedimentation assays using our CEP290 truncation constructs. Truncations containing CEP290 region M were found to significantly associate with microtubules in vitro, while those truncations lacking this region displayed no significant microtubule association (FIG. 4C, D). Thus, region M was found to be necessary and sufficient to mediate robust CEP290 microtubule association. Again, the degree to which different CEP290 truncations associated with microtubules was found to be dependent on the inclusion of the N- and C-termini. Less than 50% of the full length CEP290 constructs and CEP290 constructs lacking either terminus were found to associate with microtubules, while nearly 100% of CEP290 constructs lacking both termini associated with microtubules (FIG. 4D). To test whether CEP290 region M's microtubules association was mediated by direct microtubule binding we recombinantly expressed and purified CEP290 region M and subjected this protein to a series of microtubule co-sedimentation assays using increasing concentrations of microtubules (FIG. 4E, F). Region M was found to directly and robustly bind to microtubules in a concentration dependent manner (FIG. 4F). The calculated KD of this interaction was found to be approximately 100 nM, an affinity comparable to those of other microtubule binding proteins (38, 39).

Example 8

Figure 5C:
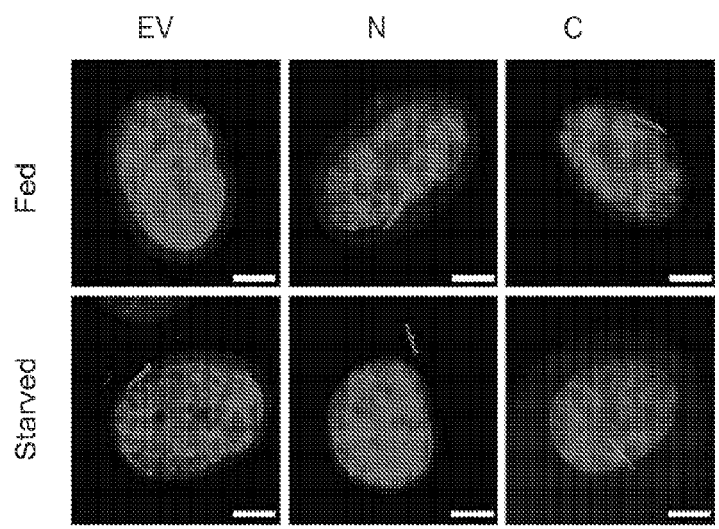
Figure 5D:
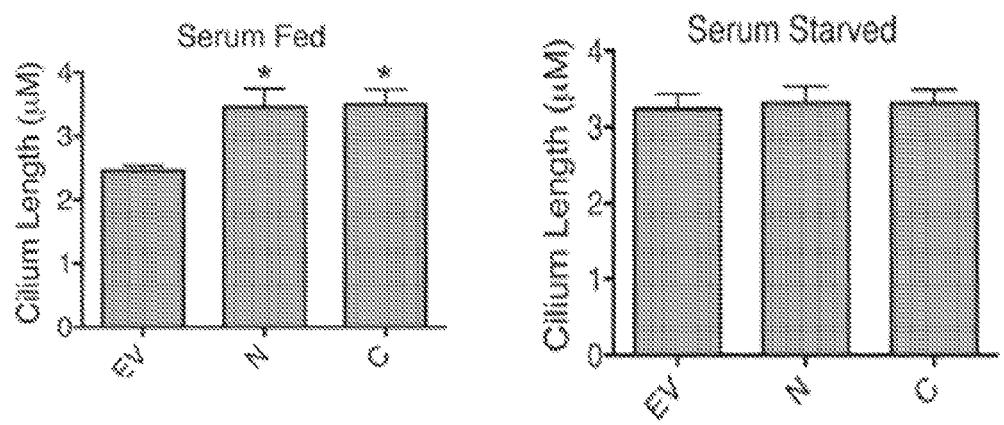

The N- and C-Termini of Cep290 Cooperate to Inhibit Protein Function and Regulate Ciliogenesis The observation that the N- and C-termini of CEP290 appeared to act in inhibiting the membrane and microtubule binding activity of the protein (FIG. 2B, 3C, 4B, 4D) suggested that these regions might be regulatory domains mediating the autoinhibition of the protein. To test this hypothesis, we transduced hTERT-RPE1 cells with lentiviral vectors encoding either the N- or C-terminal regulatory regions of the protein and observed the cells for deficits in primary cilium formation. To our surprise, we found that overexpression of either of these regulatory regions resulted not in deficiencies in primary cilium formation, but instead in significant increases in the percent of cells forming primary cilia, with more than twice as many cells forming primary cilia than those cells treated with a control vector (FIG. 5A, B). The length of cilia formed by cells overexpressing either regulatory region was also significantly increased by more than 25% compared to cells treated with the control vector (FIG. 5C, D). These increases were only observed in cells maintained in media supplemented with serum, a condition in which CEP290 is normally inhibited (24), implying that these regulatory domains act through the same pathway that mediates normal CEP290 inhibition. Dysregulation of CEP290 by overexpression of either regulatory region was sufficient to initiate aberrant primary cilium formation, suggesting that there is no further downstream regulation of ciliogenesis beyond CEP290. Interestingly, in both the serum starved and serum fed state it was noted that occasional cells transduced with the N-terminus of CEP290 appeared to produce multiple ciliary axonemes at the same centrosome (FIG. 5A, 5E to 5G). These axonemes always emanated from a single focus of pericentrin (FIG. 5F) and were often found at 90° to each other. In some, but not all cases, one or more of these axonemes co-stained with ARL13B (FIG. 5E), a protein associated with the ciliary membrane (32), indicating that at least some of these multitoaxoneme structures were fully formed cilia.

Example 9

Figure 6A:
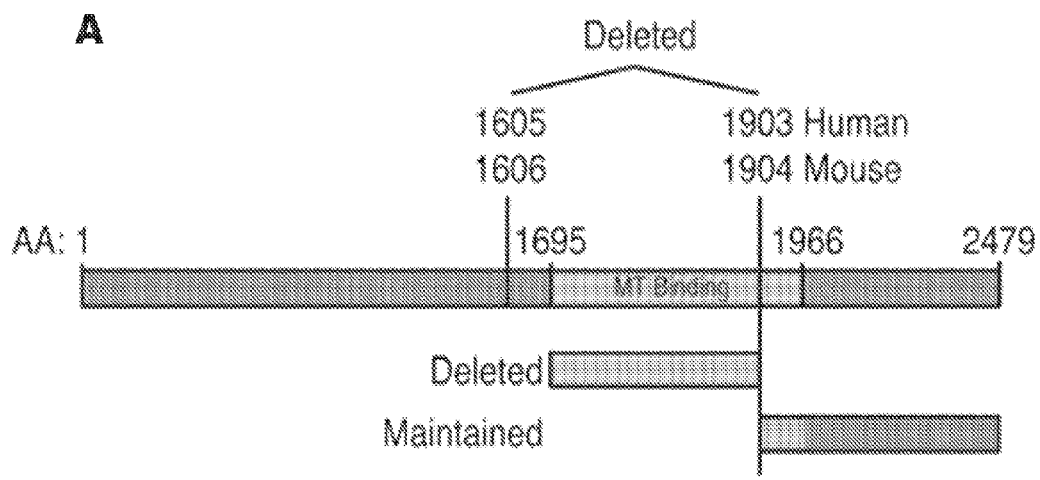
FIGS. 6A to 6F show that an in-frame deletion in Cep290 in the rd16 mouse ablates Cep290's microtubule binding activity.
Figure 6B:
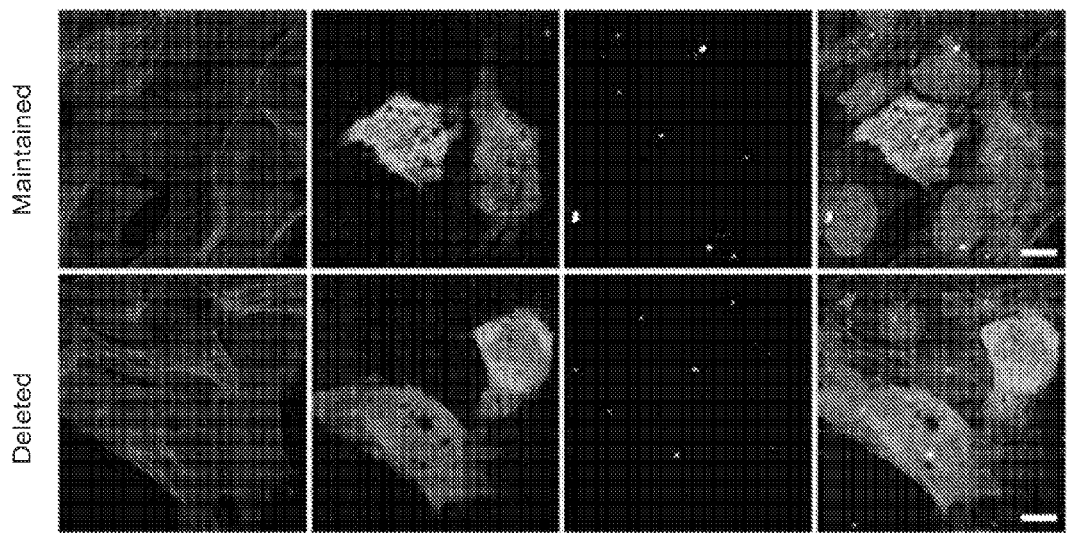

The Rd16 Mouse Cep290 Gene Encodes a Version of the Protein Deficient in Microtubule Binding The rd16 mouse is a retinal disease model of CEP290 deficiency characterized by a rapid and near complete degeneration of photoreceptors. The rd16 mouse Cep290 gene encodes a Cep290 protein containing an in-frame deletion of 298 amino acids (17) that overlaps the region of human CEP290 we identified as being critical for microtubule binding (FIG. 6A). We generated two truncation mutants of human CEP290 containing either the region of the microtubule binding domain deleted in the rd16 mouse, or the region of the microtubule binding domain spared by the mouse deletion (FIG. 6A) to test whether microtubule binding might be impaired by the rd16 deletion. To our surprise, when overexpressed in hTERT-RPE1 cells, both truncations displayed a diffuse localization pattern indicative of a primarily cytosolic localization (FIG. 6B).

Figures 6C, 6D, 6E, 6F:
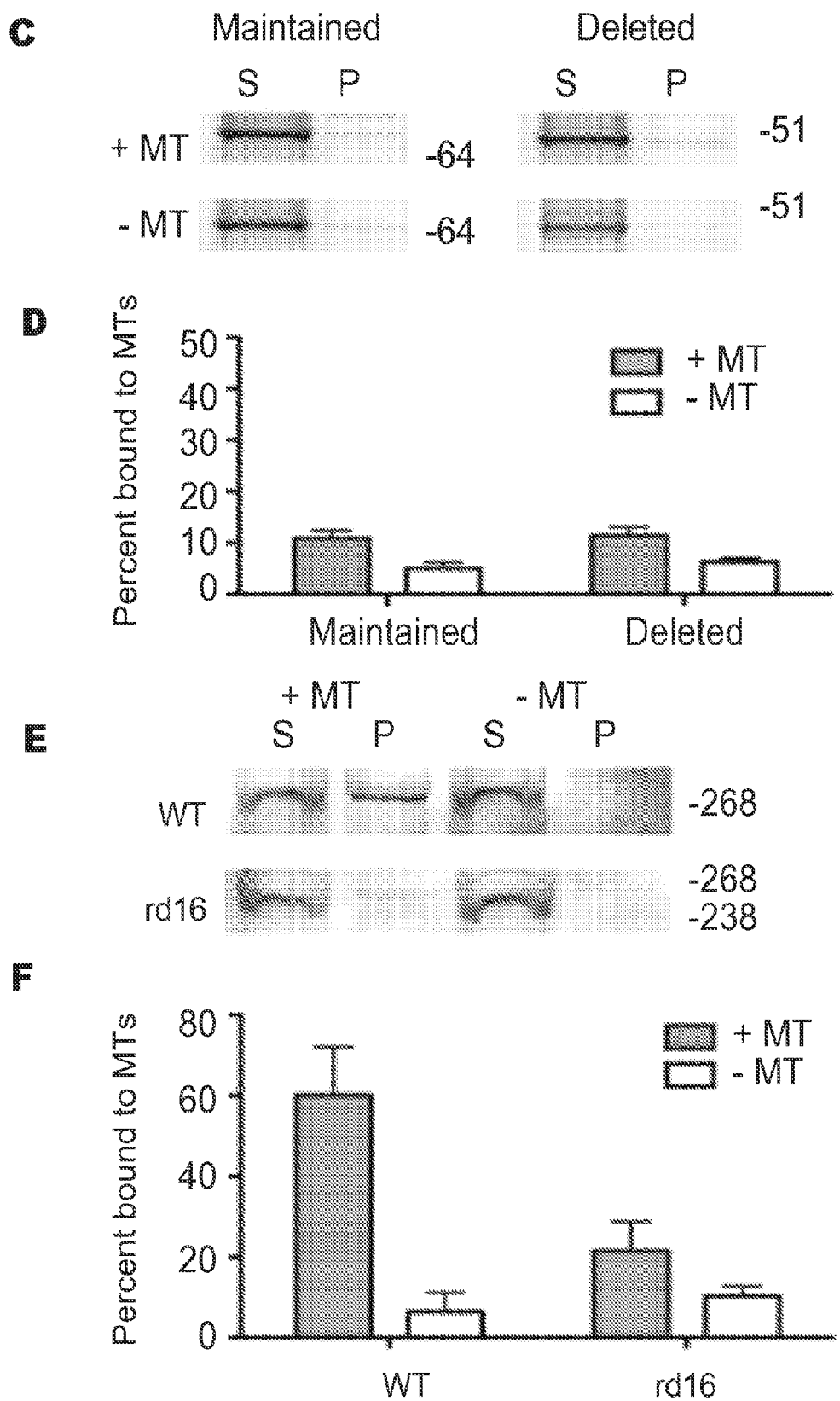

In neither case was any significant co-localization with the microtubule network observed. We confirmed that neither of these constructs was capable of associating with microtubules by subjecting them to microtubule co-sedimentation assays (FIG. 6C). Neither construct was found to significantly co-sediment with microtubules compared to the no-microtubule control (FIG. 6D), indicating both that the rd16 deletion perturbs microtubule binding and that microtubule binding is conferred by a larger portion of the CEP290 gene than was included in either of our truncations.

To confirm that rd16 Cep290 was in fact deficient in microtubule binding we subjected brain lysates from wild type (WT) and rd16 mice to microtubule co-sedimentation assays (FIG. 6E). WT Cep290 showed very significant microtubule association, with roughly 60% of the protein associating with microtubules (comparable to full length human CEP290 (FIG. 4D)), while rd16 Cep290 was found to be completely deficient in microtubule binding (FIG. 6F).

Example 10

The Rd16 Mouse is Deficient in Cilium Formation and Structure

Figures 7A, 7B, 7C, 7D, 7E:
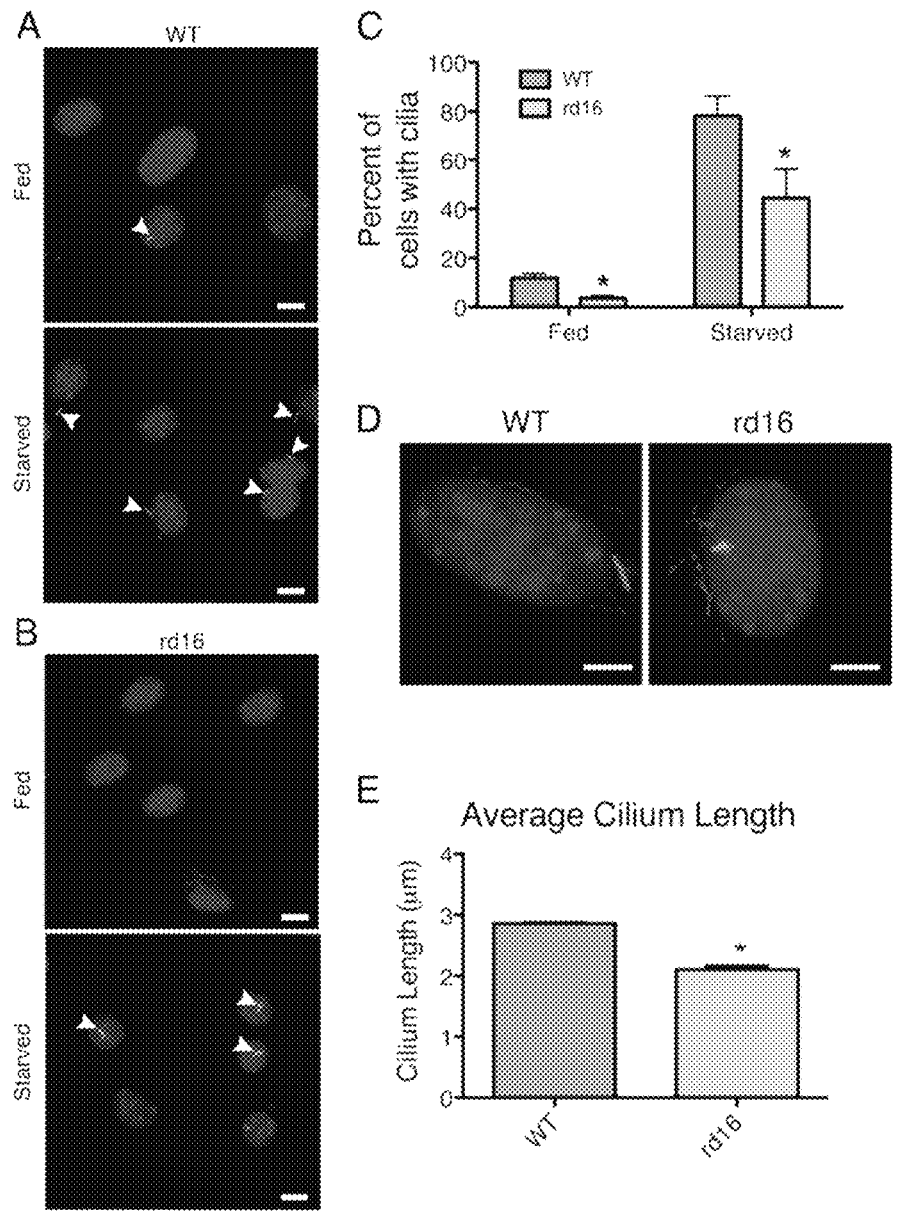
FIG. 7A to 7E show rd16 mouse fibroblasts are deficient in primary cilium formation.

While the retinal phenotype of the rd16 mouse has been well documented (40), no cellular phenotype regarding primary cilium formation or structure has yet been reported. To investigate the effect that ablation of Cep290 microtubule binding might have on primary cilium formation, we assayed primary dermal fibroblasts from rd16 and WT mice for deficiencies in cilium formation and structure. In both serum starved and serum fed conditions, rd16 fibroblasts were found to be significantly deficient in primary cilium formation, with roughly 50% fewer cells forming cilia than WT controls (FIG. 7A to C). The cilia produced by rd16 fibroblasts were also found to be more than 25% shorter than those produced by WT fibroblasts (FIG. 7D, E), further suggesting that the microtubule binding functionality of CEP290 is critically important in the maintenance and formation of the primary cilium and, when disrupted, capable of causing severe retinal disease.

Discussion of Examples 1 to 10

CEP290 acts as a bridge between the ciliary membrane and the microtubule axoneme. To date, how CEP290 functions as a component of the ciliary Y-links has been unclear. The inventors have shown that CEP290 is capable of directly binding to both ciliary membranes and microtubules, anchoring the two to each other and likely playing a key structural role in the maintenance of the cilium. Furthermore, particular domains of CEP290 responsible for mediating these specific functions have been identified. The N-terminus of the protein, containing a highly conserved amphipathic helix, mediates CEP290's membrane binding activity. Multiple experiments determined that a region near the C-terminus of CEP290, encompassing much of the protein's myosin-tail homology domain, was necessary and sufficient to mediate microtubule binding.

The location of these two functional domains at opposite ends of CEP290 immediately supports an important structural role for the protein, anchoring the ciliary membrane to the axoneme at a fixed distance, which is likely critical to the process and regulation of IFT. In addition to binding microtubules, CEP290 is capable of mediating their acetylation and bundling, two hallmarks of the microtubules that make up the ciliary axoneme, suggesting that CEP290 likely plays an important role in the stabilization, bundling, and organization of microtubules during ciliogenesis.

This data and analysis of CEP290's membrane and microtubule binding activities provides evidence that the full length protein exhibited attenuated activity when compared to truncation mutants lacking the N- or C-terminus Confirming a role for these domains in the regulation of the protein's function and ciliogenesis, we found that overexpression of either domain interfered with the normal regulation of CEP290 and was sufficient to initiate aberrant primary cilium formation. This demonstrates that there is no further downstream regulation of ciliogenesis beyond CEP290. Overexpression of the regulatory regions in serum-starved cells, where CEP290 is known to be relieved of inhibition, did not result in any increase in CEP290 activity, implying that these regulatory domains act through the same pathway that mediates normal CEP290 inhibition.

These data support a definition for a mechanism of CEP290 regulation. In one case, both regulatory loci could be acted upon by extraneous inhibitory factors to mediate CEP290 inhibition. In fact, it has been shown that the protein CP110 acts as just such an inhibitory factor, binding to the N-terminus of CEP290 and inhibiting protein activity (18, 19). Accordingly, we found that, in some cells, overexpression of CEP290's N-terminus led to the growth of multiple ciliary axonemes. This is consistent with what would be expected upon competition between endogenous CEP290 and the overexpressed N-terminal fragment for CP110, normally removed from only one end of one centriole to initiate ciliogenesis. Nonspecific depletion of CP110 from both ends of both centrioles by the overexpressed N-terminus could have resulted in the growth of multiple ciliary axonemes in the cells we observed.

If inhibition were solely dependent on the binding of a finite pool of endogenous inhibitory factor, then overexpression of the full length protein should result in competition for the inhibitory factor and only minimal, if any, observed inhibition of the overexpressed protein. Additionally, we would not expect to see inhibition of the full length construct in in vitro assays where inhibitory factors should not be present at meaningful concentrations. In all our experiments assessing protein activity, we found that full length CEP290 was significantly inhibited compared to truncation mutants lacking the novel inhibitory regions, arguing against extraneous factors such as CP110 being solely responsible for CEP290 regulation.

Figure 8:
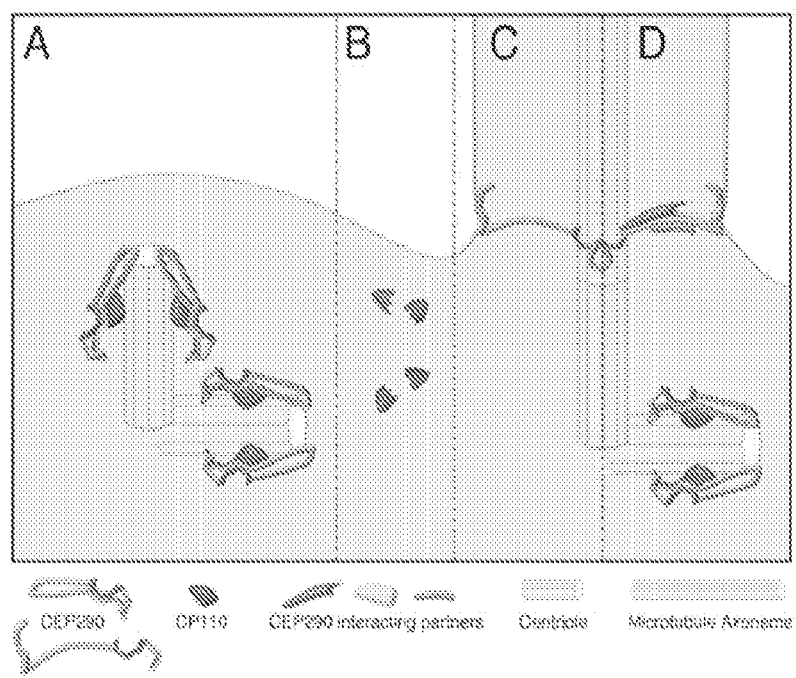
FIG. 8 shows a speculative model for CEP290 activity at the primary cilium in four panels. CEP290 is maintained in a closed, inhibited state by its N- and C-termini and CP110 during the cell cycle; CP110 bound to CEP290 with the N- and C-termini binding each other (panel A). Upon entry into $G_0$ CP110 is degraded at the mother centriole (panel B), destabilizing the closed conformation. This conformational change in the protein frees and activates CEP290's membrane binding and microtubule binding domains (panel C). In its open conformation, active CEP290 is able to recruit additional interacting partners including MTs and to initiate IFT and ciliogenesis (panel D).

Without wishing to be bound by theory, we propose an alternative model for CEP290, i.e., the two novel regulatory regions of the protein cooperate to inhibit CEP290 function, binding to each other and causing a conformational change in the protein, stabilized by the binding of CP110, that obscures important functional domains and decreases protein function (FIG. 8). Thus, the overexpression of either regulatory domain would saturate endogenous CEP290 regulatory domains, preventing the protein from homotypically binding to itself and resulting in a paradoxical increase in protein function. Similarly the full length protein, of its own accord, would be expected to display innate inhibition regardless of the experimental conditions used. These are exactly the results we observed in all of the examples.

CEP290's amphipathic helix falls within the N terminal regulatory region we have identified, positioning it appropriately to play a similar role in the autoinhibition of the protein. Additionally, the microtubule binding region we have identified is immediately adjacent to and potentially a component of the novel C-terminal inhibitory domain. This mechanism of autoinhibition, conserved among membrane-actin cytoskeleton bridging proteins, is likely operative and conserved for membrane to microtubule bridging proteins as well. CEP290 would be the first protein in this class shown to rely upon this mechanism of inhibition.

This model is also supported by observations made in the rd16 mouse, such as the apparent increased affinity of rd16 Cep290, compared to WT, for RPGR. The rd16 deletion of the microtubule binding/regulatory region may thus result in decreased autoinhibition and a higher affinity of Cep290 for its interacting partners, as was observed.

Numerous organ systems are affected by CEP290 deficiencies. The microtubule binding function of CEP290 is clearly of critical importance to the function of the protein on a cellular level and, critical in disease. The rd16 mouse Cep290 gene was found to encode a version of the protein completely deficient in microtubule binding. This mouse model also exhibits significant deficits in primary cilium formation and dramatic and rapid retinal degeneration, implying that deficiencies in microtubule binding can lead to significant pathology. In fact, over 24 unique mutations identified in human CEP290 patients map to the novel microtubule binding domain we report here (FIG. 1). Almost all of these mutations are expected to have truncating effects on the protein, which, as in the rd16 mouse, would result in significant deficiencies in microtubule binding. These truncated effects can explain the mechanism underlying the disease phenotype seen in these individuals.

Example 11

Creation of a Cep290 Knockdown Cell Line

To test the efficacy of our miniCEP290 therapeutic we first set out to create a CEP290-knockdown reporter cell line. Knockdown of CEP290 in cultured cells has been reported to result in dramatic decreases in ciliation upon serum starvation, and rescue of this phenotype serves as a good reporter for miniCEP290 protein function. Three CEP290 shRNA constructs were generated and transfected into hTERT-RPE1 cells to assess their ability to knockdown levels of CEP290 protein. One week post transfection cell lysates were collected and assayed for CEP290 by western blotting. All three constructs were found to affect a greater than 50% reduction in CEP290 protein levels, even in only transient transfection (FIGS. 12A, 12B). To assay the effects of each of these constructs on cell ciliation, retrovirus vectors encoding each construct were generated and used to transduce hTERT-RPE1 cells. Control and transduced cells were stained for acetylated tubulin and observed by fluorescence microscopy for deficits in ciliation. Construct sh2 in particular was found to affect a profound decrease in cell ciliation, with only 50% of cells forming primary cilia, compared to 75% of control cells, upon serum starvation (FIG. 12C, 12D).

We selected CEP290 shRNA construct 2 due to its efficiency in knocking down CEP290 protein levels and ability to affect a significant ciliary phenotype. CEP290 sh2 retrovirus-transduced hERT-RPE1 cells were selected for with puromycin and individual clones were isolated and assayed for CEP290 levels. All of the clones tested were found to exhibit significant knockdown of CEP290 (FIG. 13A), but clones 2.5, 2.7, and 2.8 were each found to affect the greatest knockdown, with less than 30% of endogenous CEP290 remaining (FIG. 13B). To test the ciliary phenotype of such significant knockdown of CEP290 protein, clonal lines 2.5, 2.7, and 2.8 were stained for acetylated tubulin, a marker of the primary cilium, and assayed by fluorescence microscopy for ciliation. Clone 2.8 in particular was characterized by a remarkably severe deficit in ciliation upon serum starvation (FIG. 13C), with only 5% of sh2.8 cells producing primary cilia, compared to greater than 75% of control cells (FIG. 13D). In the serum fed state, sh2.8 cells formed cilia only extremely rarely, making accurate quantification difficult (data not shown). CEP290 shRNA 2.8 cell line was selected as a reporter for miniCEP290 gene rescue.

Example 12

Design of a miniCEP290 Gene

Figure 14A:
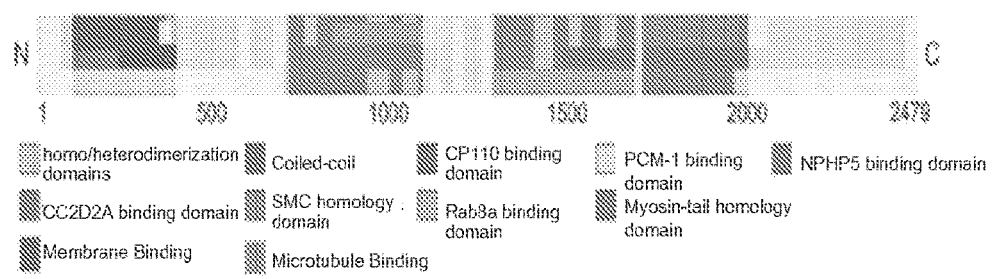
FIGS. 14A and 14B show the construction and testing of a miniCEP290 construct.
Figure 14B:
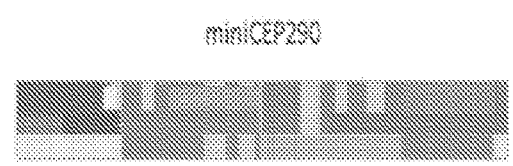

To design a miniCEP290 gene small enough to fit within AAV's limited packaging capacity and to maintain as much of the protein as possible, CEP290 amino acids 130-380, 700-1040, 1260-1605, and 1695-1990 were included, making for a total open reading frame of only 3.7 kb, small enough for AAV packaging (FIG. 14A, 14B). MiniCEP290 was thus strategically designed to include CEP290's membrane and microtubule binding domains and almost all of CEP290's PCM-1, NPHP5, CC2D2A, and Rab8A binding domains, while leaving out as much of CEP290's known autoregulatory domains as possible. The mini gene was codon optimized, both to increase expression levels and to harden the transcript against the effects of the shRNA used to generate the CEP290 knockdown reporter cell line, and synthesized by DNA 2.0.

Example 13

MiniCEP290 Localizes Correctly in hTERT-RPE1 Cells

As a preliminary test of miniCEP290's ability to recapitulate CEP290 functionality, a GFP-fused miniCEP290 expression construct was created. Upon transfection into hTERT-RPE1 cells, miniCEP290 was found to localize to discrete puncta throughout the cytoplasm (FIG. 14C), a pattern similar to that observed for overexpressed full-length CEP290. In cells where primary cilia were present, a punctus of miniCEP290 was always found exactly at the ciliary transition zone, immediately between the ciliary axoneme and centrosome (as indicated by acetylated tubulin and pericentrin staining, respectively; FIG. 14C), indicating that, at least in cells with endogenous CEP290 expression, miniCEP290 was capable of correctly localizing to the same compartment as its full-length counterpart.

MiniCEP290 localizes appropriately in hTERT-RPE1 cells and doesn't seem to interfere with ciliogenesis, an important concern when overexpressing truncation mutants. To determine whether miniCEP290 is also capable of binding to microtubules and cellular membranes, two functions recently discovered to be critical to full-length CEP290's role in cilium formation, a panel of immunoprecipitation experiments is performed to confirm that the minigene is capable of interacting with known CEP290 binding partners, an aspect of CEP290 biology important to the protein's function at the cilium. The miniCEP290 gene is subcloned into a lentiviral vector to assess its ability to rescue the ciliogenesis phenotype of the sh2.8 cell line.

Results in cell culture are validated in animal models to demonstrate therapeutic use. The lentiviral vectors are tested in early postnatal rd16 mice as this leads to transduction of at least some photoreceptor precursor cells. Also, AAV vectors encoding the miniCEP290 gene are generated and subretinally administered to rd16 mice. Since miniCEP290 recapitulates some of full-length CEP290's function, we anticipate at least partial correction of the rd16 retinal degeneration phenotype in the treated eyes.

Example 14

In Vivo Studies in a Cpe290 Mutant Animal

For in vivo studies, virus is delivered subretinally or intravitreally under direct surgical visualization using methods described previously (Bennett, J., et al. 1999 *Proc. Natl. Acad. Sci. USA* 96, 9920-9925 and Bennett, J. et al, 2000 *Meth. Enzymol.* 316, 777 to 789). Eyes from three animals, e.g., mice or dogs, are injected either subretinally or intravitreally with an AAV8bCEP290 vector or AAV2/5 CEP290 vector, each containing the minigene CEP290 of SEQ ID NO: 5 under control of the rhodopsin kinase promoter. Control eyes are untreated. Other animals are kept as untreated controls.

The compositions containing the AAV vectors in isotonic sodium chloride solution are administered by subretinal injection at suitable concentrations—for larger animals about $1.5 \times 10^{11}$ vg/ml in volumes of 150 to 400 µl and in smaller concentrations or volumes for mice. Any detachments are anticipated to resolve spontaneously within 24 hours Animals are evaluated post-operatively for evidence of ocular or systemic toxicity, virus exposure to extraocular tissue, virus shedding, unfavorable immune response or other untoward effects. None is expected to be found.

Eyes are evaluated clinically at regular intervals following the surgery to identify inflammation. Humoral and intraocular antibodies specific to AAV capsid proteins are evaluated as described in Bennett, J., et al. 1999 *Proc. Natl. Acad. Sci. USA* 96, 9920 to 9925, incorporated herein by reference. Hematology and blood chemistries are expected to reveal no evidence of systemic toxicity.

To correlate transgene expression with changed visual function, one subretinally injected eye is surgically enucleated 99 days post injection. The eyecup is divided into temporal-superior, temporal-inferior, nasal-superior, and nasal-inferior quadrants. From each quadrant, the retina, and photoreceptor cells are separately harvested and dissected under RNase free conditions and rapidly frozen. Total RNA is prepared from these cells using the TRIzol Reagent kit (Life Technologies, Gaithersburg, Md.). DNA is extracted from the same tissues according to the vendor's protocol. cDNA is amplified from total RNA using RNA PCR kit (Perkin Elmer, Foster City, Calif.) and the conditions listed above.

Genomic PCR demonstrates persistence of transferred viral DNA photoreceptor cells. From noninfected cells of the affected animal, only mutant product amplifies, but several days posttransfection in vitro the CEP290 minigene should yield the overwhelming product.

RT-PCR (figures not shown) demonstrates expression of CEP290 minigene message in photoreceptor cells. PCR analyses of serum and tear fluid show no sign of virus shedding after injection. Reverse transcriptase (RT)-PCR on sera, conjunctiva, eyelids, the gland of the third eyelid, and the optic nerve from the enucleated eye of BR29 are anticipated to be negative for the transgene many days post injection, indicating that virus escape to extraocular tissues is below detectable levels.

Retinal and visual function testing is then conducted using electroretinograms (ERGS). The physiological consequences of the treatments are assessed by electroretinography (ERG) (Banin, E., et al. 1999 *Neuron* 23, 549 to 57). Animals are dark-adapted (overnight), premedicated with acepromazine (0.55 mg/kg, IM) and atropine (0.03 mg/kg, IM) and anesthetized by intermittent ketamine (15 mg/kg, IV, repeated every 15 minutes). Pulse rate, oxygen saturation and temperature are monitored throughout. The cornea is anesthetized with topical proparacaine HCl (1%) and pupils dilated with cyclopenylate (1%) and phenylephrine (2.5%).

Full field ERGs are recorded using a computer-based system (EPIC-XL, LKC Technologies, Inc., Gaithersburg, Md.) and Burian-Allen contact lens electrodes (Hansen Ophthalmics, Iowa City, Iowa) (Banin, E., et al. 1999 *Neuron* 23, 549-57). Dark-adapted luminance-response functions are obtained with blue (Wratten 47A) flash stimuli spanning ~6 log units (−2.9 to +2.8 log scottocd.s.m$^{-2}$).

ERG b-wave amplitudes are measured conventionally from baseline or a-wave trough to positive peak; a-wave amplitude is measured from baseline to negative peak at the maximal stimulus. For isolating cone pathway function, animals are light-adapted and 29 Hz flicker ERGs evoked with white flash stimuli (0.4 log cd.s.m$^{-2}$) on a background (0.8 log cd.m$^{-2}$); amplitudes are measured between successive negative and positive peaks and timing from stimulus to the next positive peak. Ocular axial length and pupil diameter are measured for each experiment to permit calculation of retinal illuminance.

The restoration of retinal/visual function in the experimental model by subretinal AAV to RPE65 is demonstrated by the results of the above-described ERGs. A comparison of dark-adapted ERGs evoked by increasing intensities of blue light stimuli in a control animal with ERGs to the same stimuli in the disease model animal shows the affected animal has elevated thresholds, reduced amplitudes and waveform shape changes (i.e., b-waves but no detectable a-waves). Over a 5 log unit range of increasing stimulus intensity, the ERG of normal animals are anticipated to respond with increasing amplitude of bipolar cell (b-wave) and photoreceptor (a-wave) components. At all intensities these signals are dominated by rod photoreceptor retinal pathways. Compared to normal animals, the threshold stimulus required to elicit an ERG response from model animals is elevated.

Retinal function is improved in eyes treated with subretinal AAV to CEP290, compared to pretreatment recordings. After subretinal AAV to RPE65 therapy, the mutant animal is anticipated to show an improved b-wave threshold, a large increase of a- and b-wave amplitudes (although not to normal levels) and an ERG waveform shape that is similar to controls.

The details of photoreceptor function are analyzed by the amplitude and timing of the ERG photoresponses evoked by 2.8 log scottocd.s.m$^{-2}$ flashes. All eyes with subretinal AAV-CEP290 fragment treatment recover cone flicker responses. Cone flicker ERGs are readily recordable post-treatment).

Transmission of retinal activity to higher visual pathways is demonstrated by pupillometry. Animals are dark-adapted for more than 3 hours and pupil responses are obtained sequentially from each eye using full-field green stimuli (−3.2 to +3.0 log scot-cd.m$^{-2}$) of ~2 second duration. Pupils are imaged with a video camera under infrared illumination and continuously recorded on a VCR. Dynamic changes in pupil diameters are measured from single frames displayed on the video monitor in relation to the timing of each stimulus. Pupil responses are calculated by subtracting the smallest pupil diameter achieved within 2 seconds after the stimulus onset from the diameter measured in the dark.

All tested pupils are expected to constrict in response to high intensity stimuli. The threshold intensity to reach a criterion pupillary response is anticipated to be improved in subretinally-treated eyes compared with untreated eyes.

Qualitative visual assessment of treated animals is performed at post injection using an obstacle course and observers masked to the experimental design. Visual behavior is also documented by video recording. Results of behavioral testing are anticipated to be consistent with the electrophysiological results.

Without further description, it is believed that one of ordinary skill in the art can, using the preceding description and illustrative examples, make and utilize the compositions of the present invention and practice the claimed methods. While the invention has been described and illustrated herein by references to various specific materials, procedures and examples, it is understood that the invention is not restricted to the particular combinations of material and procedures selected for that purpose. The disclosures of T. G. Drivas et al, *J Clin Invest.* 2013; 123(10):4525-4539 and U.S. provisional patent application No. 61/847,016, as well as all patents, patent applications and other references, including the Sequence Listing cited in this specification are hereby incorporated by reference in their entirety.

TABLE 2

(Sequence Listing Free Text)
The following information is provided for sequences containing free text under numeric identifier <223>.

| SEQ ID NO: (containing free text) | Free text under <223> |
|---|---|
| 3 | Synthetic construct having codon optimization of human nucleic acid sequence for CEP290 |
| 4 | Synthetic construct having codon optimization of human protein sequence for CEP290 |
| 5 | Synthetic Construct; nucleic acid sequence containing codon optimized human CEP290 fragments spliced together in a single open reading frame; the nucleic acid sequences encoding fragments aa130 to 380, aa700 to 1040; aa1260 to 1605 and aa1695 to 1990. |
| 6 | Synthetic Construct; amino acid sequence containing codon optimized human CEP290 fragments spliced together in a single open reading frame: aa130 to 380, aa700 to 1040; aa1260 to 1605 and aa1695 to 1990. |

REFERENCES

1. Kobayashi T, Dynlacht B D. Regulating the transition from centriole to basal body. *J Cell Biol.* 2011; 193(3): 435-444.
2. Davenport J R et al. Disruption of intraflagellar transport in adult mice leads to obesity and slow onset cystic kidney disease. *Curr Biol.* 2007; 17(18):1586-1594.
3. Han Y-G et al. Dual and opposing roles of primary cilia in medulloblastoma development. *Nat Med.* 2009; 15(9): 1062-1065.
4. Wong S Y et al. Primary cilia can both mediate and suppress Hedgehog pathway-dependent tumorigenesis. *Nat Med.* 2009; 15(9):1055-1061.
5. Berbari N F, et al., Bardet-Biedl syndrome proteins are required for the localization of G protein-coupled receptors to primary cilia. *Proc Natl Acad Sci USA.* 2008; 105(11): 4242-4246.
6. Lancaster M A et al. Defective Wnt-dependent cerebellar midline fusion in a mouse model of Joubert syndrome. *Nat Med.* 2011; 17(6):726-731.
7. Waters A M, Beales P L. Ciliopathies: an expanding disease spectrum. *Pediatr Nephrol.* 2011; 26(7):1039-1056.
8. D'Angelo A, Franco B. The dynamic cilium in human diseases. *Pathogenetics.* 2009; 2(1):3.
9. Perrault I et al. Spectrum of NPHP6/CEP290 mutations in Leber congenital amaurosis and delineation of the associated phenotype. *Hum Mutat.* 2007; 28(4):416.
10. Den Hollander A I, et al. Leber congenital amaurosis: genes, proteins and disease mechanisms. *Prog Retin Eye Res.* 2008; 27(4):391-419.
11. Sayer J A et al. The centrosomal protein nephrocystin-6 is mutated in Joubert syndrome and activates transcription factor ATF4. *Nat Genet.* 2006; 38(6):674-681.
12. Valente E M et al. Mutations in CEP290, which encodes a centrosomal protein, cause pleiotropic forms of Joubert syndrome. *Nat Genet.* 2006; 38(6):623-625.
13. Brancati F et al. CEP290 mutations are frequently identified in the oculo-renal form of Joubert syndrome-related disorders. *Am J Hum Genet.* 2007; 81(1):104-113.
14. Helou J et al. Mutation analysis of NPHP6/CEP290 in patients with Joubert syndrome and Senior-Løken syndrome. *J Med Genet.* 2007; 44(10):657-663.

15. Baala L et al. Pleiotropic effects of CEP290 (NPHP6) mutations extend to Meckel syndrome. *Am J Hum Genet.* 2007; 81(1):170-179.
16. Moradi P, et al. Focus on molecules: centrosomal protein 290 (CEP290). *Exp Eye Res.* 2011; 92(5):316-317.
17. Chang B et al. In-frame deletion in a novel centrosomal/ciliary protein CEP290/NPHP6 perturbs its interaction with RPGR and results in early-onset retinal degeneration in the rd16 mouse. *Hum Mol Genet.* 2006; 15(11):1847-1857.
18. Tsang W Y et al. CP110 suppresses primary cilia formation through its interaction with CEP290, a protein deficient in human ciliary disease. *Dev Cell.* 2008; 15(2):187-197.
19. Spektor A, et al. Cep97 and CP110 suppress a cilia assembly program. *Cell.* 2007; 130(4):678-690.
20. Goetz S C, et al. The spinocerebellar ataxia-associated gene Tau tubulin kinase 2 controls the initiation of ciliogenesis. *Cell.* 2012; 151(4):847-858.
21. Pedersen L B, Rosenbaum J L. Intraflagellar transport (IFT) role in ciliary assembly, resorption and signalling. *Curr Top Dev Biol.* 2008; 85:23-61.
22. Craige B et al. CEP290 tethers flagellar transition zone microtubules to the membrane and regulates flagellar protein content. *J Cell Biol.* 2010; 190(5):927-940.
23. Kim J, et al. CEP290 interacts with the centriolar satellite component PCM-1 and is required for Rabb localization to the primary cilium. *Hum Mol Genet.* 2008; 17(23):3796-3805.
24. Stowe T R, et al. The centriolar satellite proteins Cep72 and Cep290 interact and are required for recruitment of BBS proteins to the cilium. *Mol Biol Cell.* 2012; 23(17):3322-3335.
25. Williams C L et al. MKS and NPHP modules cooperate to establish basal body/transition zone membrane associations and ciliary gate function during ciliogenesis. *J Cell Biol.* 2011; 192(6):1023-1041.
26. Hu Q, Nelson W J. Ciliary diffusion barrier: the gatekeeper for the primary cilium compartment. *Cytoskeleton (Hoboken).* 2011; 68(6):313-324.
27. Kee H L et al. A size-exclusion permeability barrier and nucleoporins characterize a ciliary pore complex that regulates transport into cilia. *Nat Cell Biol.* 2012; 14(4):431-437.
28. Gorden N T et al. CC2D2A is mutated in Joubert syndrome and interacts with the ciliopathy associated basal body protein CEP290. *Am J Hum Genet.* 2008; 83(5):559-571.
29. Schäfer T et al. Genetic and physical interaction between the NPHP5 and NPHP6 gene products. *Hum Mol Genet.* 2008; 17(23):3655-3662.
30. Coppieters F, et al. CEP290, a gene with many faces: mutation overview and presentation of CEP290base. *Hum Mutat.* 2010; 31(10):1097-1108.
31. Barral D C et al. Arl13b regulates endocytic recycling traffic. *Proc Natl Acad Sci USA.* 2012; 109(52):21354-21359.
32. Cevik S et al. Joubert syndrome Arl13b functions at ciliary membranes and stabilizes protein transport in Caenorhabditis elegans. *J Cell Biol.* 2010; 188(6):953-969.
33. Li Y, et al. The small GTPases ARL to 13 and ARL to 3 coordinate intraflagellar transport and ciliogenesis. *J Cell Biol.* 2010; 189(6):1039-1051.
34. Mu F T et al. EEA1, an early endosome-associated protein. EEA1 is a conserved alpha-helical peripheral membrane protein flanked by cysteine "fingers" and contains a calmodulin-binding IQ motif. *J Biol Chem.* 1995; 270(22):13503-13511.
35. Seaman M N, et al. Cytosolic and membrane-associated proteins involved in the recruitment of AP-1 adaptors onto the trans-Golgi network. *J Biol Chem.* 1996; 271(41):25446-25451.
36. Klee C B. Ca2+-dependent phospholipid- (and membrane-) binding proteins. *Biochemistry.* 1988; 27(18):6645-6653.
37. Cornell R B, Taneva S G. Amphipathic helices as mediators of the membrane interaction of amphitropic proteins, and as modulators of bilayer physical properties. *Curr Protein Pept Sci.* 2006; 7(6):539-552.
38. Gustke N, et al. Domains of tau protein and interactions with microtubules. *Biochemistry.* 1994; 33(32):9511-9522.
39. Kikkawa M, et al. 15 A resolution model of the monomeric kinesin motor, KIF1A. *Cell.* 2000; 100(2):241-252.
40. Cideciyan A V et al. Cone photoreceptors are the main targets for gene therapy of NPHP5 (IQCB1) or NPHP6 (CEP290) blindness: generation of an all-cone Nphp6 hypomorph mouse that mimics the human retinal ciliopathy. *Hum Mol Genet.* 2011; 20(7):1411-1423.
41. Weber K L, et al. A microtubule-binding myosin required for nuclear anchoring and spindle assembly. *Nature.* 2004; 431(7006): 325-329.
42. Moen R J, et al. Characterization of a myosin VII MyTH/FERM domain. *J Mol Biol.* 2011; 413(1):17-23.
43. Gilula N B, Satir P. The ciliary necklace. A ciliary membrane specialization. *J Cell Biol.* 1972; 53(2):494-509.
44. Alieva I B, et al. Experimental model for studying the primary cilia in tissue culture cells. *Membr Cell Biol.* 1999; 12(6):895-905.
45. D'Angiolella V et al. SCF(Cyclin F) controls centrosome homeostasis and mitotic fidelity through CP110 degradation. *Nature.* 2010; 466(7302):138-142.
46. Smith W J, et al. Structure of the active N-terminal domain of Ezrin. Conformational and mobility changes identify keystone interactions. *J Biol Chem.* 2003; 278 (7):4949-4956.
47. Song X et al. A novel membrane-dependent on/off switch mechanism of talin FERM domain at sites of cell adhesion. *Cell Res.* 2012; 22(11):1533-1545
48. International Patent Application Publication WO 2009/121536 A1.
49. Baye, L M et al, 2011; Hum Mol Genet, 20(8):1467-77
50. Boye et al, 2012 Human Gene Ther., 23(10):1101-15

The invention claimed is:

1. A synthetic or recombinant nucleic acid sequence encoding a truncated CEP290 protein comprising discontinuous CEP290 amino acid fragments spliced together in a single open reading frame, said truncated CEP290 protein having biological activity that mimics the biological activity of normal full-length CEP290, wherein the truncated CEP290 protein comprises the amino acid sequence of SEQ ID NO: 6.

2. A synthetic or recombinant nucleic acid sequence encoding a truncated CEP290 protein comprising discontinuous CEP290 fragments spliced together in a single open reading frame, said truncated CEP290 protein having biological activity that mimics the biological activity of normal full-length CEP290, wherein the nucleic acid sequence comprises the nucleic acid sequence of SEQ ID NO: 5.

3. A synthetic or recombinant nucleic acid sequence encoding a truncated CEP290 protein comprising discontinuous CEP290 fragments spliced together in a single open reading frame, said truncated CEP290 protein having biological activity that mimics the biological activity of normal full-length CEP290, wherein the discontinuous CEP290 fragments comprise the amino acid sequence of SEQ ID NO: 49 and the amino acid sequence of SEQ ID NO: 53.

4. The synthetic or recombinant nucleic acid sequence of claim 3, wherein the discontinuous CEP290 fragments further comprise the amino acid sequence of SEQ ID NO: 51.

5. The synthetic or recombinant nucleic acid sequence of claim 3, wherein the discontinuous CEP290 fragments further comprise the amino acid sequence of SEQ ID NO: 52.

6. The synthetic or recombinant nucleic acid sequence of claim 3, wherein the discontinuous CEP290 fragments further comprise the amino acid sequence of SEQ ID NO: 51 and the amino acid sequence of SEQ ID NO: 52.

* * * * *

SEQUENCE LISTING

<160> NUMBER OF SEQ ID NOS: 61

<210> SEQ ID NO 1
<211> LENGTH: 7437
<212> TYPE: DNA

<213> ORGANISM: Homo sapiens

<400> SEQUENCE: 1

| | | | | | |
|---|---|---|---|---|---|
| atgccaccta | atataaactg | gaaagaaata | atgaaagttg | acccagatga | cctgccccgt | 60 |
| caagaagaac | tggcagataa | tttattgatt | tccttatcca | aggtggaagt | aaatgagcta | 120 |
| aaaagtgaaa | agcaagaaaa | tgtgatacac | cttttcagaa | ttactcagtc | actaatgaag | 180 |
| atgaaagctc | aagaagtgga | gctggctttg | gaagaagtag | aaaaagctgg | agaagaacaa | 240 |
| gcaaaatttg | aaaatcaatt | aaaaactaaa | gtaatgaaac | tggaaaatga | actggagatg | 300 |
| gctcagcagt | ctgcaggtgg | acgagatact | cggttttttac | gtaatgaaat | ttgccaactt | 360 |
| gaaaaacaat | tagaacaaaa | agatagagaa | ttggaggaca | tggaaaagga | gttggagaaa | 420 |
| gagaagaaag | ttaatgagca | attggctctt | cgaaatgagg | aggcagaaaa | tgaaaacagc | 480 |
| aaattaagaa | gagagaacaa | acgtctaaag | aaaaagaatg | aacaactttg | tcaggatatt | 540 |
| attgactacc | agaaacaaat | agattcacag | aaagaaacac | ttttatcaag | aagaggggaa | 600 |
| gacagtgact | accgatcaca | gttgtctaaa | aaaaactatg | agcttatcca | atatcttgat | 660 |
| gaaattcaga | ctttaacaga | agctaatgag | aaaattgaag | ttcagaatca | agaaatgaga | 720 |
| aaaaatttag | aagagtctgt | acaggaaatg | gagaagatga | ctgatgaata | aatagaatg | 780 |
| aaagctattg | tgcatcagac | agataatgta | atagatcagt | taaaaaaaga | aaacgatcat | 840 |
| tatcaacttc | aagtgcagga | gcttacagat | cttctgaaat | caaaaaatga | agaagatgat | 900 |
| ccaattatgg | tagctgtcaa | tgcaaaagta | gaagaatgga | agctaatttt | gtcttctaaa | 960 |
| gatgatgaaa | ttattgagta | tcagcaaatg | ttacataacc | taagggagaa | acttaagaat | 1020 |
| gctcagcttg | atgctgataa | aagtaatgtt | atggctctac | agcagggtat | acaggaacga | 1080 |
| gacagtcaaa | ttaagatgct | caccgaacaa | gtagaacaat | atacaaaaga | aatgaaaag | 1140 |
| aatacttgta | ttattgaaga | tttgaaaaat | gagctccaaa | gaaacaaagg | tgcttcaacc | 1200 |
| ctttctcaac | agactcatat | gaaaattcag | tcaacgttag | acattttaaa | agagaaaact | 1260 |
| aaagaggctg | agagaacagc | tgaactggct | gaggctgatg | ctagggaaaa | ggataaagaa | 1320 |
| ttagttgagg | ctctgaagag | gttaaaagat | tatgaatcgg | gagtatatgg | tttagaagat | 1380 |
| gctgtcgttg | aaataaagaa | ttgtaaaaac | caaattaaaa | taagagatcg | agagattgaa | 1440 |
| atattaacaa | aggaaatcaa | taaacttgaa | ttgaagatca | gtgatttcct | tgatgaaaat | 1500 |
| gaggcactta | gagagcgtgt | gggccttgaa | ccaaagacaa | tgattgattt | aactgaattt | 1560 |
| agaaatagca | acacttaaa | acagcagcag | tacagagctg | aaaaccagat | tcttttgaaa | 1620 |
| gagattgaaa | gtctagagga | agaacgactt | gatctgaaaa | aaaaaattcg | tcaaatggct | 1680 |
| caagaaagag | gaaaagaag | tgcaacttca | ggattaacca | ctgaggacct | gaacctaact | 1740 |
| gaaaacattt | ctcaaggaga | tagaataagt | gaaagaaaat | tggatttatt | gagcctcaaa | 1800 |
| aatatgagtg | aagcacaatc | aaagaatgaa | tttctttcaa | gagaactaat | tgaaaaagaa | 1860 |
| agagatttag | aaaggagtag | gacagtgata | gccaaatttc | agaataaatt | aaaagaatta | 1920 |
| gttgaagaaa | ataagcaact | tgaagaaggt | atgaaagaaa | tattgcaagc | aattaaggaa | 1980 |
| atgcagaaag | atcctgatgt | taaaggagga | gaaacatctc | taattatccc | tagccttgaa | 2040 |
| agactagtta | atgctataga | atcaaagaat | gcagaaggaa | tctttgatgc | gagtctgcat | 2100 |
| ttgaaagccc | aagttgatca | gcttaccgga | agaaatgaag | aattaagaca | ggagctcagg | 2160 |
| gaatctcgga | agaggctat | aaattattca | cagcagttgg | caaaagctaa | tttaaagata | 2220 |
| gaccatcttg | aaaaagaaac | tagtcttttta | cgacaatcag | aaggatcgaa | tgttgttttt | 2280 |

```
aaaggaattg acttacctga tgggatagca ccatctagtg ccagtatcat taattctcag    2340
aatgaatatt taatacattt gttacaggaa ctagaaaata aagaaaaaaa gttaaagaat    2400
ttagaagatt ctcttgaaga ttacaacaga aaatttgctg taattcgtca tcaacaaagt    2460
ttgttgtata aagaatacct aagtgaaaag gagacctgga aaacagaatc taaaacaata    2520
aaagaggaaa agagaaaact tgaggatcaa gtccaacaag atgctataaa agtaaaagaa    2580
tataataatt tgctcaatgc tcttcagatg gattcggatg aaatgaaaaa aatacttgca    2640
gaaaatagta ggaaaattac tgttttgcaa gtgaatgaaa aatcacttat aaggcaatat    2700
acaaccttag tagaattgga gcgacaactt agaaaagaaa atgagaagca aaagaatgaa    2760
ttgttgtcaa tggaggctga agtttgtgaa aaaattgggt gtttgcaaag atttaaggaa    2820
atggccattt tcaagattgc agctctccaa aaagttgtag ataatagtgt ttctttgtct    2880
gaactagaac tggctaataa acagtacaat gaactgactg ctaagtacag ggacatcttg    2940 caaaagata atatgcttgt tcaaagaaca agtaacttgg aacacctgga gtgtgaaaac     3000
atctccttaa aagaacaagt ggagtctata aataaagaac tggagattac caaggaaaaa    3060
cttcacacta ttgaacaagc ctgggaacag gaaactaaat taggtaatga atctagcatg    3120
gataaggcaa agaaatcaat aaccaacagt gacattgttt ccatttcaaa aaaataact    3180 atgctggaaa tgaaggaatt aaatgaaagg cagcgggctg aacattgtca aaaaatgtat    3240
gaacacttac ggacttcgtt aaagcaaatg gaggaacgta attttgaatt ggaaaccaaa    3300
tttgctgagc ttaccaaaat caatttggat gcacagaagg tggaacagat gttaagagat    3360
gaattagctg atagtgtgag caaggcagta agtgatgctg ataggcaacg gattctagaa    3420
ttagagaaga atgaaatgga actaaaagtt gaagtgtcaa aactgagaga gatttctgat    3480
attgccagaa gacaagttga aattttgaat gcacaacaac aatctaggga caaggaagta    3540
gagtccctca gaatgcaact gctagactat caggcacagt ctgatgaaaa gtcgctcatt    3600
gccaagttgc accaacataa tgtctctctt caactgagtg aggctactgc tcttggtaag    3660
ttggagtcaa ttcatctaa actgcagaag atggaggcct acaacttgcg cttagagcag    3720
aaacttgatg aaaaagaaca ggctctctat tatgctcgtt tggagggaag aaacagagca    3780
aaacatctgc gccaaacaat tcagtctcta cgacgacagt ttagtggagc tttacccttg    3840
gcacaacagg aaaagttctc caaaacaatg attcaactac aaaatgacaa acttaagata    3900
atgcaagaaa tgaaaaattc tcaacaagaa catagaaata tggagaacaa aacattggag    3960
atggaattaa aattaaaggg cctggaagag ttaataagca cttttaaagga taccaaagga    4020 gcccaaaagg taatcaactg gcatatgaaa atagaagaac ttcgtcttca agaacttaaa    4080
ctaaatcggg aattagtcaa ggataaagaa gaaataaaat atttgaataa cataatttct    4140
gaatatgaac gtacaatcag cagtcttgaa gaagaaattg tgcaacagaa caagtttcat    4200
gaagaaagac aaatggcctg ggatcaaaga gaagttgacc tggaacgcca actagacatt    4260
tttgaccgtc agcaaaatga atactaaat gcggcacaaa agtttgaaga agctacagga    4320
tcaatccctg accctagttt gccccttcca aatcaacttg agatcgctct aaggaaaatt    4380
aaggagaaca ttcgaataat tctagaaaca cgggcaactt gcaaatcact agaagagaaa    4440
ctaaaagaga aagaatctgc tttaaggtta gcagaacaaa atatactgtc aagagacaaa    4500
gtaatcaatg aactgaggct tcgattgcct gccactgcag aaagagaaaa gctcatagct    4560
gagctaggca gaaagagat ggaaccaaaa tctcaccaca cattgaaaat tgctcatcaa    4620
```

```
accattgcaa acatgcaagc aaggttaaat caaaaagaag aagtattaaa gaagtatcaa    4680
cgtcttctag aaaaagccag agaggagcaa agagaaattg tgaagaaaca tgaggaagac    4740
cttcatattc ttcatcacag attagaacta caggctgata gttcactaaa taaattcaaa    4800
caaacggctt gggatttaat gaaacagtct cccactccag ttcctaccaa caagcatttt    4860
attcgtctgg ctgagatgga acagacagta gcagaacaag atgactctct ttcctcactc    4920
ttggtcaaac taaagaaagt atcacaagat ttggagagac aaagagaaat cactgaatta    4980
aaagtaaaag aatttgaaaa tatcaaatta cagcttcaag aaaaccatga agatgaagtg    5040
aaaaaagtaa agcggaagt agaggattta aagtatcttc tggaccagtc acaaaaggag    5100
tcacagtgtt taaaatctga acttcaggct caaaagaag caaattcaag agctccaaca    5160
actacaatga gaaatctagt agaacggcta agagccaat tagccttgaa ggagaaacaa    5220
cagaaagcac ttagtcgggc acttttagaa ctccgggcag aaatgacagc agctgctgaa    5280
gaacgtatta tttctgcaac ttctcaaaaa gaggcccatc tcaatgttca acaaatcgtt    5340
gatcgacata ctagagagct aaagacacaa gttgaagatt taaatgaaaa tcttttaaaa    5400
ttgaaagaag cacttaaaac aagtaaaaac agagaaaact cactaactga taatttgaat    5460
gacttaaata atgaactgca aaagaaacaa aaagcctata ataaaatact tagagagaaa    5520
gaggaaattg atcaagagaa tgatgaactg aaaaggcaaa ttaaaagact aaccagtgga    5580
ttacagggca aaccctgac agtaataaaa caaagtctaa ttgaagaact ccaaaggaaa    5640
gttaaaaaac tagagaacca attagaggga aaggtggagg aagtagacct aaaacctatg    5700
aaagaaaaga atgctaaaga agaattaatt aggtgggaag aaggtaaaaa gtggcaagcc    5760
aaaatagaag gaattcgaaa caagttaaaa gagaagagg gggaagtctt tactttaaca    5820
aagcagttga atactttgaa ggatcttttt gccaaagccg ataaagagaa acttactttg    5880
cagaggaaac taaaaacaac tggcatgact gttgatcagg ttttgggaat acgagctttg    5940
gagtcagaaa agaattgga agaattaaaa agagaaatc ttgacttaga aaatgatata    6000
ttgtatatga gggcccacca agctcttcct cgagattctg ttgtagaaga tttacattta    6060
caaaatagat acctccaaga aaacttcat gctttagaaa acagtttttc aaaggataca    6120
tattctaagc cttcaatttc aggaatagag tcagatgatc attgtcagag agaacaggag    6180
cttcagaagg aaaacttgaa gttgtcatct gaaatattg aactgaaatt tcagcttgaa    6240
caagcaaata aagatttgcc aagattaaag aatcaagtca gagatttgaa ggaaatgtgt    6300
gaatttctta agaaagaaaa agcagaagtt cagcggaaac ttggccatgt tagagggtct    6360
ggtagaagtg gaaagacaat cccagaactg gaaaaaacca ttggtttaat gaaaaaagta    6420
gttgaaaaag tccagagaga aaatgaacag ttgaaaaaag catcaggaat attgactagt    6480
gaaaaaatgg ctaatattga gcaggaaaat gaaaaattga aggctgaatt agaaaaactt    6540
aaagctcatc ttgggcatca gttgagcatg cactatgaat ccaagaccaa aggcacagaa    6600
aaaattattg ctgaaaatga aaggcttcgt aaagaactta aaaagaaac tgatgctgca    6660 gagaaattac ggatagcaaa gaataattta gagatattaa atgagaagat gacagttcaa    6720
ctagaagaga ctggtaagag attgcagttt gcagaaagca gaggtccaca gcttgaaggt    6780
gctgacagta agagctggaa atccattgtg gttacaagaa tgtatgaaac caagttaaaa    6840
gaattggaaa ctgatattgc caaaaaaaat caaagcatta ctgaccttaa acagcttgta    6900
aaagaagcaa cagagagaga acaaaaagtt aacaaataca atgaagacct tgaacaacag    6960
attaagattc ttaaacatgt tcctgaaggt gctgagacag agcaaggcct taaacgggag    7020
```

-continued

```
cttcaagttc ttagattagc taatcatcag ctggataaag agaaagcaga attaatccat    7080
cagatagaag ctaacaagga ccaaagtgga gctgaaagca ccatacctga tgctgatcaa    7140
ctaaaggaaa aaataaaaga tctagagaca cagctcaaaa tgtcagatct agaaaagcag    7200
catttgaagg aggaaataaa gaagctgaaa aagaactgg aaaattttga tccttcattt    7260
tttgaagaaa ttgaagatct taagtataat tacaaggaag aagtgaagaa gaatattctc    7320
ttagaagaga aggtaaaaaa actttcagaa caattgggag ttgaattaac tagccctgtt    7380
gctgcttctg aagagtttga agatgaagaa gaaagtcctg ttaatttccc catttac      7437
```

<210> SEQ ID NO 2
<211> LENGTH: 2479
<212> TYPE: PRT
<213> ORGANISM: Homo sapiens

<400> SEQUENCE: 2

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

```
Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
            325                 330                 335

Lys Leu Lys Asn Ala Gln Leu Asp Ala Asp Lys Ser Asn Val Met Ala
        340                 345                 350

Leu Gln Gln Gly Ile Gln Glu Arg Asp Ser Gln Ile Lys Met Leu Thr
    355                 360                 365

Glu Gln Val Glu Gln Tyr Thr Lys Glu Met Glu Lys Asn Thr Cys Ile
370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
            405                 410                 415

Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
            485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
    530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
    595                 600                 605

Asn Glu Phe Leu Ser Arg Glu Leu Ile Glu Lys Glu Arg Asp Leu Glu
610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
            645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
        675                 680                 685

Lys Asn Ala Glu Gly Ile Phe Asp Ala Ser Leu His Leu Lys Ala Gln
    690                 695                 700

Val Asp Gln Leu Thr Gly Arg Asn Glu Glu Leu Arg Gln Glu Leu Arg
705                 710                 715                 720
```

-continued

```
Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
        755                 760                 765

Ile Ala Pro Ser Ser Ala Ser Ile Ile Asn Ser Gln Asn Glu Tyr Leu
    770                 775                 780

Ile His Leu Leu Gln Glu Leu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
        835                 840                 845

Asp Gln Val Gln Gln Asp Ala Ile Lys Val Lys Glu Tyr Asn Asn Leu
    850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
        915                 920                 925

Cys Glu Lys Ile Gly Cys Leu Gln Arg Phe Lys Glu Met Ala Ile Phe
    930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
            980                 985                 990

Leu Glu His Leu Glu Cys Glu Asn Ile Ser Leu Lys Glu Gln Val Glu
        995                 1000                1005

Ser Ile Asn Lys Glu Leu Glu Ile Thr Lys Glu Lys Leu His Thr
    1010                1015                1020

Ile Glu Gln Ala Trp Glu Gln Glu Thr Lys Leu Gly Asn Glu Ser
    1025                1030                1035

Ser Met Asp Lys Ala Lys Lys Ser Ile Thr Asn Ser Asp Ile Val
    1040                1045                1050

Ser Ile Ser Lys Lys Ile Thr Met Leu Glu Met Lys Glu Leu Asn
    1055                1060                1065

Glu Arg Gln Arg Ala Glu His Cys Gln Lys Met Tyr Glu His Leu
    1070                1075                1080

Arg Thr Ser Leu Lys Gln Met Glu Glu Arg Asn Phe Glu Leu Glu
    1085                1090                1095

Thr Lys Phe Ala Glu Leu Thr Lys Ile Asn Leu Asp Ala Gln Lys
    1100                1105                1110

Val Glu Gln Met Leu Arg Asp Glu Leu Ala Asp Ser Val Ser Lys
    1115                1120                1125

Ala Val Ser Asp Ala Asp Arg Gln Arg Ile Leu Glu Leu Glu Lys
```

|      |      |      |      |      | 1130 |      |      |      | 1135 |      |      |      | 1140 |      |

Asn Glu Met Glu Leu Lys Val Glu Val Ser Lys Leu Arg Glu Ile
1145                1150                1155

Ser Asp Ile Ala Arg Arg Gln Val Glu Ile Leu Asn Ala Gln Gln
1160                1165                1170

Gln Ser Arg Asp Lys Glu Val Glu Ser Leu Arg Met Gln Leu Leu
1175                1180                1185

Asp Tyr Gln Ala Gln Ser Asp Glu Lys Ser Leu Ile Ala Lys Leu
1190                1195                1200

His Gln His Asn Val Ser Leu Gln Leu Ser Glu Ala Thr Ala Leu
1205                1210                1215

Gly Lys Leu Glu Ser Ile Thr Ser Lys Leu Gln Lys Met Glu Ala
1220                1225                1230

Tyr Asn Leu Arg Leu Glu Gln Lys Leu Asp Glu Lys Glu Gln Ala
1235                1240                1245

Leu Tyr Tyr Ala Arg Leu Glu Gly Arg Asn Arg Ala Lys His Leu
1250                1255                1260

Arg Gln Thr Ile Gln Ser Leu Arg Arg Gln Phe Ser Gly Ala Leu
1265                1270                1275

Pro Leu Ala Gln Gln Glu Lys Phe Ser Lys Thr Met Ile Gln Leu
1280                1285                1290

Gln Asn Asp Lys Leu Lys Ile Met Gln Glu Met Lys Asn Ser Gln
1295                1300                1305

Gln Glu His Arg Asn Met Glu Asn Lys Thr Leu Glu Met Glu Leu
1310                1315                1320

Lys Leu Lys Gly Leu Glu Glu Leu Ile Ser Thr Leu Lys Asp Thr
1325                1330                1335

Lys Gly Ala Gln Lys Val Ile Asn Trp His Met Lys Ile Glu Glu
1340                1345                1350

Leu Arg Leu Gln Glu Leu Lys Leu Asn Arg Glu Leu Val Lys Asp
1355                1360                1365

Lys Glu Glu Ile Lys Tyr Leu Asn Asn Ile Ile Ser Glu Tyr Glu
1370                1375                1380

Arg Thr Ile Ser Ser Leu Glu Glu Ile Val Gln Gln Asn Lys
1385                1390                1395

Phe His Glu Glu Arg Gln Met Ala Trp Asp Gln Arg Glu Val Asp
1400                1405                1410

Leu Glu Arg Gln Leu Asp Ile Phe Asp Arg Gln Gln Asn Glu Ile
1415                1420                1425

Leu Asn Ala Ala Gln Lys Phe Glu Glu Ala Thr Gly Ser Ile Pro
1430                1435                1440

Asp Pro Ser Leu Pro Leu Pro Asn Gln Leu Glu Ile Ala Leu Arg
1445                1450                1455

Lys Ile Lys Glu Asn Ile Arg Ile Ile Leu Glu Thr Arg Ala Thr
1460                1465                1470

Cys Lys Ser Leu Glu Glu Lys Leu Lys Glu Lys Glu Ser Ala Leu
1475                1480                1485

Arg Leu Ala Glu Gln Asn Ile Leu Ser Arg Asp Lys Val Ile Asn
1490                1495                1500

Glu Leu Arg Leu Arg Leu Pro Ala Thr Ala Glu Arg Glu Lys Leu
1505                1510                1515

Ile Ala Glu Leu Gly Arg Lys Glu Met Glu Pro Lys Ser His His
1520                1525                1530

```
Thr Leu Lys Ile Ala His Gln Thr Ile Ala Asn Met Gln Ala Arg
1535                1540                1545

Leu Asn Gln Lys Glu Glu Val Leu Lys Lys Tyr Gln Arg Leu Leu
1550                1555                1560

Glu Lys Ala Arg Glu Glu Gln Arg Glu Ile Val Lys Lys His Glu
1565                1570                1575

Glu Asp Leu His Ile Leu His His Arg Leu Glu Leu Gln Ala Asp
1580                1585                1590

Ser Ser Leu Asn Lys Phe Lys Gln Thr Ala Trp Asp Leu Met Lys
1595                1600                1605

Gln Ser Pro Thr Pro Val Pro Thr Asn Lys His Phe Ile Arg Leu
1610                1615                1620

Ala Glu Met Glu Gln Thr Val Ala Glu Gln Asp Asp Ser Leu Ser
1625                1630                1635

Ser Leu Leu Val Lys Leu Lys Lys Val Ser Gln Asp Leu Glu Arg
1640                1645                1650

Gln Arg Glu Ile Thr Glu Leu Lys Val Lys Glu Phe Glu Asn Ile
1655                1660                1665

Lys Leu Gln Leu Gln Glu Asn His Glu Asp Glu Val Lys Lys Val
1670                1675                1680

Lys Ala Glu Val Glu Asp Leu Lys Tyr Leu Leu Asp Gln Ser Gln
1685                1690                1695

Lys Glu Ser Gln Cys Leu Lys Ser Glu Leu Gln Ala Gln Lys Glu
1700                1705                1710

Ala Asn Ser Arg Ala Pro Thr Thr Thr Met Arg Asn Leu Val Glu
1715                1720                1725

Arg Leu Lys Ser Gln Leu Ala Leu Lys Glu Lys Gln Gln Lys Ala
1730                1735                1740

Leu Ser Arg Ala Leu Leu Glu Leu Arg Ala Glu Met Thr Ala Ala
1745                1750                1755

Ala Glu Glu Arg Ile Ile Ser Ala Thr Ser Gln Lys Glu Ala His
1760                1765                1770

Leu Asn Val Gln Gln Ile Val Asp Arg His Thr Arg Glu Leu Lys
1775                1780                1785

Thr Gln Val Glu Asp Leu Asn Glu Asn Leu Leu Lys Leu Lys Glu
1790                1795                1800

Ala Leu Lys Thr Ser Lys Asn Arg Glu Asn Ser Leu Thr Asp Asn
1805                1810                1815

Leu Asn Asp Leu Asn Asn Glu Leu Gln Lys Lys Gln Lys Ala Tyr
1820                1825                1830

Asn Lys Ile Leu Arg Glu Lys Glu Glu Ile Asp Gln Glu Asn Asp
1835                1840                1845

Glu Leu Lys Arg Gln Ile Lys Arg Leu Thr Ser Gly Leu Gln Gly
1850                1855                1860

Lys Pro Leu Thr Asp Asn Lys Gln Ser Leu Ile Glu Glu Leu Gln
1865                1870                1875

Arg Lys Val Lys Lys Leu Glu Asn Gln Leu Glu Gly Lys Val Glu
1880                1885                1890

Glu Val Asp Leu Lys Pro Met Lys Glu Lys Asn Ala Lys Glu Glu
1895                1900                1905

Leu Ile Arg Trp Glu Glu Gly Lys Lys Trp Gln Ala Lys Ile Glu
1910                1915                1920
```

```
Gly Ile Arg Asn Lys Leu Lys Glu Lys Glu Gly Glu Val Phe Thr
1925                1930                1935

Leu Thr Lys Gln Leu Asn Thr Leu Lys Asp Leu Phe Ala Lys Ala
1940                1945                1950

Asp Lys Glu Lys Leu Thr Leu Gln Arg Lys Leu Lys Thr Thr Gly
1955                1960                1965

Met Thr Val Asp Gln Val Leu Gly Ile Arg Ala Leu Glu Ser Glu
1970                1975                1980

Lys Glu Leu Glu Glu Leu Lys Lys Arg Asn Leu Asp Leu Glu Asn
1985                1990                1995

Asp Ile Leu Tyr Met Arg Ala His Gln Ala Leu Pro Arg Asp Ser
2000                2005                2010

Val Val Glu Asp Leu His Leu Gln Asn Arg Tyr Leu Gln Glu Lys
2015                2020                2025

Leu His Ala Leu Glu Lys Gln Phe Ser Lys Asp Thr Tyr Ser Lys
2030                2035                2040

Pro Ser Ile Ser Gly Ile Glu Ser Asp Asp His Cys Gln Arg Glu
2045                2050                2055

Gln Glu Leu Gln Lys Glu Asn Leu Lys Leu Ser Ser Glu Asn Ile
2060                2065                2070

Glu Leu Lys Phe Gln Leu Glu Gln Ala Asn Lys Asp Leu Pro Arg
2075                2080                2085

Leu Lys Asn Gln Val Arg Asp Leu Lys Glu Met Cys Glu Phe Leu
2090                2095                2100

Lys Lys Glu Lys Ala Glu Val Gln Arg Lys Leu Gly His Val Arg
2105                2110                2115

Gly Ser Gly Arg Ser Gly Lys Thr Ile Pro Glu Leu Glu Lys Thr
2120                2125                2130

Ile Gly Leu Met Lys Lys Val Val Glu Lys Val Gln Arg Glu Asn
2135                2140                2145

Glu Gln Leu Lys Lys Ala Ser Gly Ile Leu Thr Ser Glu Lys Met
2150                2155                2160

Ala Asn Ile Glu Gln Glu Asn Glu Lys Leu Lys Ala Glu Leu Glu
2165                2170                2175

Lys Leu Lys Ala His Leu Gly His Gln Leu Ser Met His Tyr Glu
2180                2185                2190

Ser Lys Thr Lys Gly Thr Glu Lys Ile Ile Ala Glu Asn Glu Arg
2195                2200                2205

Leu Arg Lys Glu Leu Lys Lys Glu Thr Asp Ala Ala Glu Lys Leu
2210                2215                2220

Arg Ile Ala Lys Asn Asn Leu Glu Ile Leu Asn Glu Lys Met Thr
2225                2230                2235

Val Gln Leu Glu Glu Thr Gly Lys Arg Leu Gln Phe Ala Glu Ser
2240                2245                2250

Arg Gly Pro Gln Leu Glu Gly Ala Asp Ser Lys Ser Trp Lys Ser
2255                2260                2265

Ile Val Val Thr Arg Met Tyr Glu Thr Lys Leu Lys Glu Leu Glu
2270                2275                2280

Thr Asp Ile Ala Lys Lys Asn Gln Ser Ile Thr Asp Leu Lys Gln
2285                2290                2295

Leu Val Lys Glu Ala Thr Glu Arg Glu Gln Lys Val Asn Lys Tyr
2300                2305                2310

Asn Glu Asp Leu Glu Gln Gln Ile Lys Ile Leu Lys His Val Pro
```

-continued

```
           2315                2320                2325

Glu Gly  Ala Glu Thr Glu Gln  Gly Leu Lys Arg Glu  Leu Gln Val
         2330                2335                2340

Leu Arg  Leu Ala Asn His Gln  Leu Asp Lys Glu Lys  Ala Glu Leu
         2345                2350                2355

Ile His  Gln Ile Glu Ala Asn  Lys Asp Gln Ser Gly  Ala Glu Ser
         2360                2365                2370

Thr Ile  Pro Asp Ala Asp Gln  Leu Lys Glu Lys Ile  Lys Asp Leu
         2375                2380                2385

Glu Thr  Gln Leu Lys Met Ser  Asp Leu Glu Lys Gln  His Leu Lys
         2390                2395                2400

Glu Glu  Ile Lys Lys Leu Lys  Lys Glu Leu Glu Asn  Phe Asp Pro
         2405                2410                2415

Ser Phe  Phe Glu Glu Ile Glu  Asp Leu Lys Tyr Asn  Tyr Lys Glu
         2420                2425                2430

Glu Val  Lys Lys Asn Ile Leu  Leu Glu Glu Lys Val  Lys Lys Leu
         2435                2440                2445

Ser Glu  Gln Leu Gly Val Glu  Leu Thr Ser Pro Val  Ala Ala Ser
         2450                2455                2460

Glu Glu  Phe Glu Asp Glu Glu  Glu Ser Pro Val Asn  Phe Pro Ile
         2465                2470                2475

Tyr
```

<210> SEQ ID NO 3
<211> LENGTH: 7437
<212> TYPE: DNA
<213> ORGANISM: Artificial Sequence
<220> FEATURE:
<223> OTHER INFORMATION: Synthetic construct having codon optimization
      of human nucleic acid sequence for CEP290

<400> SEQUENCE: 3

```
atgccccaa  acatcaattg  gaaagagatt  atgaaggtag  accccgatga  tcttcctaga     60
caggaagagc  ttgctgataa  tcttttgatc  tccctcagta  aggtggaggt  gaacgagctg   120
aaatcagaaa  agcaggagaa  tgttatacat  cttttcgca  tcacccagtc  tctcatgaag    180
atgaaagcac  aagaagtgga  actcgcattg  gaagaggttg  agaaagcggg  cgaggagcag   240
gctaagtttg  aaaccagct  gaaaacgaag  gttatgaagc  tggagaacga  gctcgagatg    300
gcgcagcagt  cagccggagg  tagggataca  aggttttga  gaaatgagat  atgtcagttg    360
gagaaacagc  ttgagcagaa  agatcgggag  ttggaggaca  tggaaaagga  gctcgaaaaa   420 gaaagaaag  tgaatgagca  gctcgccctg  cggaacgaag  aagccgaaaa  cgaaaacagt    480
aagctgagaa  gggaaaacaa  acggctgaaa  agaagaacg  agcagctctg  tcaggatatc     540
atagattacc  agaaacagat  cgattcacaa  aaagaaactt  tgctctcacg  aaggggagaa   600
gatagcgact  atagatcaca  gctcagtaag  aagaactacg  agctgattca  gtacttggat   660
gaaattcaga  ccctgacaga  agccaatgag  aaaatcgaag  tacagaacca  gaaatgcgg    720 aaaaaccctcg  aggagagcgt  gcaagagatg  gagaagatga  ccgacgaata  caaccggatg  780
aaagctattg  tacatcagac  tgacaacgtc  atcgatcaat  tgaagaaaga  aaacgaccac  840
taccaattgc  aagttcaaga  gctgaccgat  ctcctcaaat  ccaaaaacga  ggaggacgac  900
cccataatgg  tggccgtgaa  cgctaaagtc  gaagagtgga  aactgatcct  ctcctccaag  960
gatgacgaga  ttatcgaata  tcagcagatg  ctgcacaatc  tgcgcgagaa  gttgaagaat  1020
```

```
gcacagctcg acgccgacaa atctaatgta atggccctgc agcagggaat ccaagaaagg    1080
gatagtcaaa tcaaaatgct tactgagcaa gtcgaacagt acaccaaaga gatggagaaa    1140
aacacttgca tcattgagga cctcaagaac gaattgcagc gaaacaaggg ggcttctaca    1200
ctcagtcagc aaaactcatat gaaaatccag agcactctgg acatcctcaa ggagaaaaca    1260
aaggaagccg agcgcacagc cgaactggca gaagccgatg cacgcgagaa ggacaaagag    1320
cttgtggagg ctcttaagcg gctcaaggac tacgaatccg gggtttacgg actcgaggac    1380
gccgtcgtgg aaatcaagaa ctgcaagaac cagattaaga ttcgggacag agagatcgaa    1440
atcctgacca aggaaatcaa taagctggaa ctcaagatta gtgatttcct cgatgagaac    1500
gaagccctgc gggaacgcgt aggactggaa cccaaaacaa tgatcgatct gaccgaattc    1560
cgcaattcta agcaccttaa acagcagcag taccgagcgg agaaccagat tctgctgaaa    1620
gaaattgagt cacttgagga ggagagactt gatcttaaga agaagattag gcaaatggct    1680
caagaacggg aaaacggtc cgcaacgagt ggcctgacta ccgaggatct gaatcttacg    1740
gagaacataa gccaaggcga caggatttca gaacggaaat tggatttgct tagcctcaag    1800
aatatgagtg aagcccagag caagaatgag tttctgtcca gggaactgat tgaaaaagag    1860
cgggaccttg aacggagcag aacagtcatc gccaagttcc agaacaaact gaaagagctg    1920
gtggaggaaa acaagcagct ggaggaaggc atgaaggaaa ttctccaggc aatcaaggag    1980
atgcaaaagg acccagatgt caaaggcgga gaaacgtccc tgattatccc ctcactcgag    2040
cggctggtga atgccattga atctaagaac gcagagggta tctttgacgc ttcactgcac    2100
cttaaggccc aagtcgatca gctgacaggc agaaatgagg agcttcgcca ggaactccgc    2160
gagtcccgca agaagcaat caactatagt cagcagctgg caaaagctaa cctcaaaatc    2220
gaccatctcg aaaaagaaac gtccctgctc agacagtccg agggcagcaa tgttgtgttc    2280
aagggcatag atctcccgga cggcattgcc cccagtagtg cttccatcat aaactcccaa    2340
aacgaatact tgatccatct gctgcaagag cttgagaaca aggagaagaa acttaagaat    2400
ttggaggaca gcctcgagga ctacaatagg aagttcgctg tcatccggca ccagcagagc    2460
ttgttgtata aggaatatct tagtgagaag gagacttgga aaacagagag taaaacgata    2520
aaggaagaga agcgcaaact ggaggaccag gttcagcagg atgccattaa ggtgaaagag    2580
tacaataacc ttctgaatgc gttgcagatg gacagcgacg agatgaagaa atcttggct    2640 gagaattccc ggaaaatcac cgtgctccaa gtcaatgaga agtccctcat aagacagtac    2700
accacactcg tcgaactgga aagacagctg aggaaggaga cgaaaaaaca gaaaaacgag    2760
ctgcttagca tggaggccga agtatgcgag aagataggat gtctgcaaag gttcaaagag    2820
atggccatat tcaagatcgc ggcactccag aaagtggtcg ataactctgt gtctctcagc    2880
gagttggaac tggccaataa gcagtacaat gagctgacag ccaagtatag agatattctc    2940
caaaaggaca atatgttggt ccagaggact tcaaatcttg agcacttgga gtgtgagaac    3000
atttcactta aagaacaagt agagtccatc aataaggagc tggaaatcac aaaagaaaaa    3060
ctgcacacaa tagaacaagc atgggaacag gaaactaaac tgggcaacga aagcagcatg    3120
gacaaggcca gaaatcaat cactaacagc gacattgtga gtatttctaa gaagatcact    3180
atgctggaga tgaaagagtt gaacgagagg cagagagccg agcactgtca gaagatgtat    3240
gaacacctta gaacatccct caaacagatg aggaaagaa acttcgagct ggaaaccaag    3300
tttgctgagc tgaccaagat taaccttgac gcccagaagg tggagcagat gctgcgcgat    3360
gaactggccg acagtgtaag caaggcggtc agcgacgcag accgccagcg gattttggag    3420
```

```
ctggaaaaga acgaaatgga gctcaaagtc gaggtcagta agcttcgcga aatcagcgat    3480
atcgctaggc ggcaggtgga gattcttaat gcccagcaac agtcccgaga taaagaggtt    3540
gagtcactcc ggatgcaact cctcgattac caggcccaga gcgacgaaaa gtcactcatc    3600
gcaaagttgc accagcacaa cgtttccctt cagctgtccg aagccacagc cttggggaaa    3660
ttggaatcca ttaccagcaa gctgcagaaa atggaggcgt acaatctgcg cctcgagcag    3720
aagctggacg agaaggagca ggccctgtat tacgctcgcc tggaaggacg gaaccgagct    3780
aagcatctgc ggcagactat tcagagcctg cggaggcaat tcagcggagc cctgcctctc    3840
gctcagcaag agaagttttc taaaacaatg atacagctgc aaaatgataa actcaaaatc    3900
atgcaagaga tgaagaactc tcagcaggag cacagaaaca tggagaacaa gacactggag    3960
atggaactca agttgaaagg gctggaggag ttgatttcta cccttaagga tacaaaaggg    4020
gcacaaaagg tcattaactg gcatatgaag atagaggaac tgagactgca agaactcaaa    4080
ctgaatagag agttggtgaa ggacaaagaa gagatcaagt accttaacaa tatcatctca    4140
gaatacgagc ggactatcag ttcactggag gaggagattg ttcagcagaa caaattccat    4200
gaggaaaggc agatggcttg ggatcagaga gaagtggatt tggagaggca gctggacatc    4260
tttgatagac aacagaatga gatcctcaac gcggcacaga aattcgaaga agcgacaggt    4320
tcaatcccg atccatctct tccactccca aatcagcttg agattgctct gagaaagatc    4380
aaggaaaaca tacggattat ccttgagact agagctactt gcaagagcct cgaagaaaaa    4440
ctgaaggaga aggagtctgc actgcggctt gcagagcaga atatcctgtc tcgggataag    4500
gttatcaacg aactgcgcct gaggcttcct gctaccgccg agagagagaa actgattgct    4560
gaacttggac gaaagaaat ggaaccgaaa tctcatcaca cgctcaagat tgcccaccag    4620
acaatagcca atatgcaggc caggctgaat cagaaagagg ggtgctgaa gaagtatcaa    4680
cgcctgctgg agaaagctag ggaggagcag agagagattg tgaaaagca cgaagaggac    4740
ctccatatcc tccatcatcg gttggagctt caggcagatt cctccctgaa caagtttaag    4800
cagacagcct gggaccttat gaaacagtct ccaacacccg tgccgactaa caagcatttc    4860
atccgcttgg cggagatgga acagaccgtg gccgagcagg acgactcact gtcctcccct    4920
ctggtaaagc tgaagaaagt aagccaggac cttgagcgac agagggagat taccgagctg    4980
aaggtcaagg aattcgagaa catcaagctg caactccaag agaaccacga agatgaggtc    5040
aagaaggtga aggcagaagt tgaggatttg aagtatctgc tggatcagtc ccagaaggag    5100
tcacagtgct tgaaaagcga actgcaggca cagaaggaag ccaatagccg agcccctacc    5160
acgactatga gaaacttggt ggaacggctc aaatcccagc tcgccttgaa agagaagcag    5220
cagaaagcac tgtcccgagc gttgcttgag ctgcgagctg agatgacggc agcagccgag    5280
gagcgcatca tttctgctac cagccaaaaa gaggcccatc tgaacgttca acagattgtt    5340
gaccgccaca ccagggagct caagacccaa gtagaggacc ttaatgagaa cctgctgaaa    5400
ttgaaagagg cacttaagac ctccaagaac cgggagaact ctctgaccga caatctgaac    5460
gatctgaaca atgagctgca gaagaaacag aaagcctaca ataagatact gcgagaaaaa    5520
gaagaaatag accaggagaa cgatgagctc aaacggcaga tcaaaggct gacaagcggc    5580
ctgcaaggca aacctctcac cgacaataag cagtccctga tcgaggaact gcagcggaaa    5640
gtgaagaaac tcgaaaacca acttgaaggg aaggtgaag aagttgacct taagcccatg    5700
aaagagaaaa acgcaaagga ggaactcatt agatgggagg agggcaaaaa gtggcaggcc    5760
```

| aaaatcgaag ggataaggaa caaattgaaa gagaaggaag gggaagtgtt tactctgacc | 5820 |
| aagcagctca atactctcaa ggaccttttt gctaaagccg acaaagagaa actgaccctg | 5880 |
| cagagaaagc tgaaaacaac aggcatgacc gtggaccagg tgttggggat tagggccttg | 5940 |
| gagagtgaaa aggagctgga ggagctgaaa aagcgcaatc tggacttgga gaatgatatc | 6000 |
| ttgtatatgc gcgctcacca ggctctgccg agggacagcg tggtggagga cctccatttg | 6060 |
| caaaatcgat atctccaaga gaagctccat gcgctggaaa aacagttctc taaagatacc | 6120 |
| tattccaaac cttctattag cggcattgaa tcagacgatc attgccaaag ggagcaggaa | 6180 |
| ctgcagaagg aaaacttgaa gctgagctct gagaacattg agctgaagtt ccagctggag | 6240 |
| caagccaata aggatctccc tcggctgaag aaccaggttc gggacttgaa ggagatgtgc | 6300 |
| gagtttctca aaaggaaaa ggcagaggtt cagcgcaagc tcgggcacgt gagaggctct | 6360 |
| gggaggagtg gaaaaaccat accagagctt gagaaaacta tcggtttgat gaaaaaggtc | 6420 |
| gtggagaaag tccagagaga aaatgagcag ctgaaaaagg ccagtggcat tctgacctca | 6480 |
| gagaagatgg caaacatcga acaagagaac gagaagctca aggctgaact ggaaaagctt | 6540 |
| aaggctcatc tggggcacca gctgtctatg cactatgaaa gcaagacaaa aggcaccgag | 6600 |
| aagataatcg ccgagaatga gcgcctgaga aaagaactga gaaggagac tgatgccgct | 6660 |
| gaaaagctga aatcgcaaa gaataacctt gaaatactga atgagaagat gaccgtgcag | 6720 |
| ctcgaggaaa ccggaaagcg actgcagttc gctgaatctc gagggccaca actcgaggga | 6780 |
| gcggactcta aaagctggaa gagtatagtc gtcactagga tgtatgaaac caagctgaag | 6840 |
| gaactggaaa cggacattgc taagaaaaac cagtccatca cagatctgaa acagttggta | 6900 |
| aaagaggcta ctgaaaggga gcagaaagtc aataagtata cgaggaccct cgaacagcag | 6960 |
| atcaagatac tgaaacacgt gccagaaggg gcggaaacgg agcaaggcct gaaacgagaa | 7020 |
| ctgcaagtgc tgcgactggc taatcaccag ctggataagg agaaagcaga gctgatccat | 7080 |
| cagatagaag cgaataagga tcaatctggt gcggaatcta ccatacccga cgccgatcag | 7140 |
| cttaaggaga agattaagga tctcgaaact cagttgaaga tgagcgactt ggaaaaacag | 7200 |
| cacttgaagg aagagattaa gaaactcaag aaggaactcg agaacttcga ccctagtttc | 7260 |
| tttgaggaaa tcgaggatct gaaatacaac tataaggagg aagtgaagaa gaatatcttg | 7320 |
| ctggaagaaa aggtgaaaaa gctttcagag caactcggcg tggagctgac ctctcccgta | 7380 |
| gccgcaagtg aggagtttga ggatgaagaa gaaagccctg ttaacttccc gatctat | 7437 |

<210> SEQ ID NO 4
<211> LENGTH: 2479
<212> TYPE: PRT
<213> ORGANISM: Artificial Sequence
<220> FEATURE:
<223> OTHER INFORMATION: Synthetic construct having codon optimization
      of human protein sequence for CEP290

<400> SEQUENCE: 4

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

```
Glu Val Glu Leu Ala Leu Glu Glu Val Glu Lys Ala Gly Glu Glu Gln
 65                  70                  75                  80

Ala Lys Phe Glu Asn Gln Leu Lys Thr Lys Val Met Lys Leu Glu Asn
                 85                  90                  95

Glu Leu Glu Met Ala Gln Gln Ser Ala Gly Gly Arg Asp Thr Arg Phe
             100                 105                 110

Leu Arg Asn Glu Ile Cys Gln Leu Glu Lys Gln Leu Glu Gln Lys Asp
         115                 120                 125

Arg Glu Leu Glu Asp Met Glu Lys Glu Leu Glu Glu Lys Lys Val
     130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Asn Glu Gln Leu
                 165                 170                 175

Cys Gln Asp Ile Ile Asp Tyr Gln Lys Gln Ile Asp Ser Gln Lys Glu
             180                 185                 190

Thr Leu Leu Ser Arg Arg Gly Glu Asp Ser Asp Tyr Arg Ser Gln Leu
         195                 200                 205

Ser Lys Lys Asn Tyr Glu Leu Ile Gln Tyr Leu Asp Glu Ile Gln Thr
     210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                 245                 250                 255

Tyr Asn Arg Met Lys Ala Ile Val His Gln Thr Asp Asn Val Ile Asp
             260                 265                 270

Gln Leu Lys Lys Glu Asn Asp His Tyr Gln Leu Gln Val Gln Glu Leu
         275                 280                 285

Thr Asp Leu Leu Lys Ser Lys Asn Glu Glu Asp Asp Pro Ile Met Val
     290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                 325                 330                 335

Lys Leu Lys Asn Ala Gln Leu Asp Ala Asp Lys Ser Asn Val Met Ala
             340                 345                 350

Leu Gln Gln Gly Ile Gln Glu Arg Asp Ser Gln Ile Lys Met Leu Thr
         355                 360                 365

Glu Gln Val Glu Gln Tyr Thr Lys Glu Met Glu Lys Asn Thr Cys Ile
     370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                 405                 410                 415

Lys Glu Lys Thr Lys Glu Ala Glu Arg Thr Ala Glu Leu Ala Glu Ala
             420                 425                 430

Asp Ala Arg Glu Lys Asp Lys Glu Leu Val Glu Ala Leu Lys Arg Leu
         435                 440                 445

Lys Asp Tyr Glu Ser Gly Val Tyr Gly Leu Glu Asp Ala Val Val Glu
     450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
```

```
                485                 490                 495
Leu Asp Glu Asn Glu Ala Leu Arg Glu Arg Val Gly Leu Glu Pro Lys
                500                 505                 510

Thr Met Ile Asp Leu Thr Glu Phe Arg Asn Ser Lys His Leu Lys Gln
                515                 520                 525

Gln Gln Tyr Arg Ala Glu Asn Gln Ile Leu Leu Lys Glu Ile Glu Ser
                530                 535                 540

Leu Glu Glu Arg Leu Asp Leu Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
                580                 585                 590

Lys Leu Asp Leu Leu Ser Leu Lys Asn Met Ser Glu Ala Gln Ser Lys
                595                 600                 605

Asn Glu Phe Leu Ser Arg Glu Leu Ile Glu Lys Glu Arg Asp Leu Glu
                610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
                660                 665                 670

Ser Leu Ile Ile Pro Ser Leu Glu Arg Leu Val Asn Ala Ile Glu Ser
                675                 680                 685

Lys Asn Ala Glu Gly Ile Phe Asp Ala Ser Leu His Leu Lys Ala Gln
                690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
                740                 745                 750

Ser Glu Gly Ser Asn Val Val Phe Lys Gly Ile Asp Leu Pro Asp Gly
                755                 760                 765

Ile Ala Pro Ser Ser Ala Ser Ile Ile Asn Ser Gln Asn Glu Tyr Leu
                770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
                820                 825                 830

Trp Lys Thr Glu Ser Lys Thr Ile Lys Glu Glu Lys Arg Lys Leu Glu
                835                 840                 845

Asp Gln Val Gln Gln Asp Ala Ile Lys Val Lys Glu Tyr Asn Asn Leu
                850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
                900                 905                 910
```

-continued

```
Glu Asn Glu Lys Gln Lys Asn Glu Leu Leu Ser Met Glu Ala Glu Val
        915                 920                 925

Cys Glu Lys Ile Gly Cys Leu Gln Arg Phe Lys Glu Met Ala Ile Phe
    930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
        980                 985                 990

Leu Glu His Leu Glu Cys Glu Asn Ile Ser Leu Lys Glu Gln Val Glu
            995                 1000                1005

Ser Ile Asn Lys Glu Leu Glu Ile Thr Lys Glu Lys Leu His Thr
    1010                1015                1020

Ile Glu Gln Ala Trp Glu Gln Glu Thr Lys Leu Gly Asn Glu Ser
    1025                1030                1035

Ser Met Asp Lys Ala Lys Lys Ser Ile Thr Asn Ser Asp Ile Val
    1040                1045                1050

Ser Ile Ser Lys Lys Ile Thr Met Leu Glu Met Lys Glu Leu Asn
    1055                1060                1065

Glu Arg Gln Arg Ala Glu His Cys Gln Lys Met Tyr Glu His Leu
    1070                1075                1080

Arg Thr Ser Leu Lys Gln Met Glu Glu Arg Asn Phe Glu Leu Glu
    1085                1090                1095

Thr Lys Phe Ala Glu Leu Thr Lys Ile Asn Leu Asp Ala Gln Lys
    1100                1105                1110

Val Glu Gln Met Leu Arg Asp Glu Leu Ala Asp Ser Val Ser Lys
    1115                1120                1125

Ala Val Ser Asp Ala Asp Arg Gln Arg Ile Leu Glu Leu Glu Lys
    1130                1135                1140

Asn Glu Met Glu Leu Lys Val Glu Val Ser Lys Leu Arg Glu Ile
    1145                1150                1155

Ser Asp Ile Ala Arg Arg Gln Val Glu Ile Leu Asn Ala Gln Gln
    1160                1165                1170

Gln Ser Arg Asp Lys Glu Val Glu Ser Leu Arg Met Gln Leu Leu
    1175                1180                1185

Asp Tyr Gln Ala Gln Ser Asp Glu Lys Ser Leu Ile Ala Lys Leu
    1190                1195                1200

His Gln His Asn Val Ser Leu Gln Leu Ser Glu Ala Thr Ala Leu
    1205                1210                1215

Gly Lys Leu Glu Ser Ile Thr Ser Lys Leu Gln Lys Met Glu Ala
    1220                1225                1230

Tyr Asn Leu Arg Leu Glu Gln Lys Leu Asp Glu Lys Glu Gln Ala
    1235                1240                1245

Leu Tyr Tyr Ala Arg Leu Glu Gly Arg Asn Arg Ala Lys His Leu
    1250                1255                1260

Arg Gln Thr Ile Gln Ser Leu Arg Arg Gln Phe Ser Gly Ala Leu
    1265                1270                1275

Pro Leu Ala Gln Gln Glu Lys Phe Ser Lys Thr Met Ile Gln Leu
    1280                1285                1290

Gln Asn Asp Lys Leu Lys Ile Met Gln Glu Met Lys Asn Ser Gln
    1295                1300                1305
```

-continued

Gln Glu His Arg Asn Met Glu Asn Lys Thr Leu Glu Met Glu Leu
1310             1315                 1320

Lys Leu Lys Gly Leu Glu Glu Leu Ile Ser Thr Leu Lys Asp Thr
1325             1330                 1335

Lys Gly Ala Gln Lys Val Ile Asn Trp His Met Lys Ile Glu Glu
1340             1345                 1350

Leu Arg Leu Gln Glu Leu Lys Leu Asn Arg Glu Leu Val Lys Asp
1355             1360                 1365

Lys Glu Glu Ile Lys Tyr Leu Asn Asn Ile Ile Ser Glu Tyr Glu
1370             1375                 1380

Arg Thr Ile Ser Ser Leu Glu Glu Ile Val Gln Gln Asn Lys
1385             1390                 1395

Phe His Glu Glu Arg Gln Met Ala Trp Asp Gln Arg Glu Val Asp
1400             1405                 1410

Leu Glu Arg Gln Leu Asp Ile Phe Asp Arg Gln Gln Asn Glu Ile
1415             1420                 1425

Leu Asn Ala Ala Gln Lys Phe Glu Glu Ala Thr Gly Ser Ile Pro
1430             1435                 1440

Asp Pro Ser Leu Pro Leu Pro Asn Gln Leu Glu Ile Ala Leu Arg
1445             1450                 1455

Lys Ile Lys Glu Asn Ile Arg Ile Ile Leu Glu Thr Arg Ala Thr
1460             1465                 1470

Cys Lys Ser Leu Glu Glu Lys Leu Lys Glu Lys Glu Ser Ala Leu
1475             1480                 1485

Arg Leu Ala Glu Gln Asn Ile Leu Ser Arg Asp Lys Val Ile Asn
1490             1495                 1500

Glu Leu Arg Leu Arg Leu Pro Ala Thr Ala Glu Arg Glu Lys Leu
1505             1510                 1515

Ile Ala Glu Leu Gly Arg Lys Glu Met Glu Pro Lys Ser His His
1520             1525                 1530

Thr Leu Lys Ile Ala His Gln Thr Ile Ala Asn Met Gln Ala Arg
1535             1540                 1545

Leu Asn Gln Lys Glu Glu Val Leu Lys Lys Tyr Gln Arg Leu Leu
1550             1555                 1560

Glu Lys Ala Arg Glu Glu Gln Arg Glu Ile Val Lys Lys His Glu
1565             1570                 1575

Glu Asp Leu His Ile Leu His His Arg Leu Glu Leu Gln Ala Asp
1580             1585                 1590

Ser Ser Leu Asn Lys Phe Lys Gln Thr Ala Trp Asp Leu Met Lys
1595             1600                 1605

Gln Ser Pro Thr Pro Val Pro Thr Asn Lys His Phe Ile Arg Leu
1610             1615                 1620

Ala Glu Met Glu Gln Thr Val Ala Glu Gln Asp Asp Ser Leu Ser
1625             1630                 1635

Ser Leu Leu Val Lys Leu Lys Lys Val Ser Gln Asp Leu Glu Arg
1640             1645                 1650

Gln Arg Glu Ile Thr Glu Leu Lys Val Lys Glu Phe Glu Asn Ile
1655             1660                 1665

Lys Leu Gln Leu Gln Glu Asn His Glu Asp Glu Val Lys Lys Val
1670             1675                 1680

Lys Ala Glu Val Glu Asp Leu Lys Tyr Leu Leu Asp Gln Ser Gln
1685             1690                 1695

Lys Glu Ser Gln Cys Leu Lys Ser Glu Leu Gln Ala Gln Lys Glu

```
                    1700                  1705                  1710
Ala  Asn  Ser  Arg  Ala  Pro  Thr  Thr  Thr  Met  Arg  Asn  Leu  Val  Glu
     1715                  1720                  1725

Arg  Leu  Lys  Ser  Gln  Leu  Ala  Leu  Lys  Glu  Lys  Gln  Gln  Lys  Ala
     1730                  1735                  1740

Leu  Ser  Arg  Ala  Leu  Leu  Glu  Leu  Arg  Ala  Glu  Met  Thr  Ala  Ala
     1745                  1750                  1755

Ala  Glu  Glu  Arg  Ile  Ile  Ser  Ala  Thr  Ser  Gln  Lys  Glu  Ala  His
     1760                  1765                  1770

Leu  Asn  Val  Gln  Gln  Ile  Val  Asp  Arg  His  Thr  Arg  Glu  Leu  Lys
     1775                  1780                  1785

Thr  Gln  Val  Glu  Asp  Leu  Asn  Glu  Asn  Leu  Leu  Lys  Leu  Lys  Glu
     1790                  1795                  1800

Ala  Leu  Lys  Thr  Ser  Lys  Asn  Arg  Glu  Asn  Ser  Leu  Thr  Asp  Asn
     1805                  1810                  1815

Leu  Asn  Asp  Leu  Asn  Asn  Glu  Leu  Gln  Lys  Lys  Gln  Lys  Ala  Tyr
     1820                  1825                  1830

Asn  Lys  Ile  Leu  Arg  Glu  Lys  Glu  Glu  Ile  Asp  Gln  Glu  Asn  Asp
     1835                  1840                  1845

Glu  Leu  Lys  Arg  Gln  Ile  Lys  Arg  Leu  Thr  Ser  Gly  Leu  Gln  Gly
     1850                  1855                  1860

Lys  Pro  Leu  Thr  Asp  Asn  Lys  Gln  Ser  Leu  Ile  Glu  Glu  Leu  Gln
     1865                  1870                  1875

Arg  Lys  Val  Lys  Lys  Leu  Glu  Asn  Gln  Leu  Glu  Gly  Lys  Val  Glu
     1880                  1885                  1890

Glu  Val  Asp  Leu  Lys  Pro  Met  Lys  Glu  Lys  Asn  Ala  Lys  Glu  Glu
     1895                  1900                  1905

Leu  Ile  Arg  Trp  Glu  Glu  Gly  Lys  Lys  Trp  Gln  Ala  Lys  Ile  Glu
     1910                  1915                  1920

Gly  Ile  Arg  Asn  Lys  Leu  Lys  Glu  Lys  Glu  Gly  Glu  Val  Phe  Thr
     1925                  1930                  1935

Leu  Thr  Lys  Gln  Leu  Asn  Thr  Leu  Lys  Asp  Leu  Phe  Ala  Lys  Ala
     1940                  1945                  1950

Asp  Lys  Glu  Lys  Leu  Thr  Leu  Gln  Arg  Lys  Leu  Lys  Thr  Thr  Gly
     1955                  1960                  1965

Met  Thr  Val  Asp  Gln  Val  Leu  Gly  Ile  Arg  Ala  Leu  Glu  Ser  Glu
     1970                  1975                  1980

Lys  Glu  Leu  Glu  Glu  Leu  Lys  Lys  Arg  Asn  Leu  Asp  Leu  Glu  Asn
     1985                  1990                  1995

Asp  Ile  Leu  Tyr  Met  Arg  Ala  His  Gln  Ala  Leu  Pro  Arg  Asp  Ser
     2000                  2005                  2010

Val  Val  Glu  Asp  Leu  His  Leu  Gln  Asn  Arg  Tyr  Leu  Gln  Glu  Lys
     2015                  2020                  2025

Leu  His  Ala  Leu  Glu  Lys  Gln  Phe  Ser  Lys  Asp  Thr  Tyr  Ser  Lys
     2030                  2035                  2040

Pro  Ser  Ile  Ser  Gly  Ile  Glu  Ser  Asp  Asp  His  Cys  Gln  Arg  Glu
     2045                  2050                  2055

Gln  Glu  Leu  Gln  Lys  Glu  Asn  Leu  Lys  Leu  Ser  Ser  Glu  Asn  Ile
     2060                  2065                  2070

Glu  Leu  Lys  Phe  Gln  Leu  Glu  Gln  Ala  Asn  Lys  Asp  Leu  Pro  Arg
     2075                  2080                  2085

Leu  Lys  Asn  Gln  Val  Arg  Asp  Leu  Lys  Glu  Met  Cys  Glu  Phe  Leu
     2090                  2095                  2100
```

-continued

```
Lys Lys Glu Lys Ala Glu Val Gln Arg Lys Leu Gly His Val Arg
2105                2110                2115
Gly Ser Gly Arg Ser Gly Lys Thr Ile Pro Glu Leu Glu Lys Thr
2120                2125                2130
Ile Gly Leu Met Lys Lys Val Val Glu Lys Val Gln Arg Glu Asn
2135                2140                2145
Glu Gln Leu Lys Lys Ala Ser Gly Ile Leu Thr Ser Glu Lys Met
2150                2155                2160
Ala Asn Ile Glu Gln Glu Asn Glu Lys Leu Lys Ala Glu Leu Glu
2165                2170                2175
Lys Leu Lys Ala His Leu Gly His Gln Leu Ser Met His Tyr Glu
2180                2185                2190
Ser Lys Thr Lys Gly Thr Glu Lys Ile Ile Ala Glu Asn Glu Arg
2195                2200                2205
Leu Arg Lys Glu Leu Lys Lys Glu Thr Asp Ala Ala Glu Lys Leu
2210                2215                2220
Arg Ile Ala Lys Asn Asn Leu Glu Ile Leu Asn Glu Lys Met Thr
2225                2230                2235
Val Gln Leu Glu Glu Thr Gly Lys Arg Leu Gln Phe Ala Glu Ser
2240                2245                2250
Arg Gly Pro Gln Leu Glu Gly Ala Asp Ser Lys Ser Trp Lys Ser
2255                2260                2265
Ile Val Val Thr Arg Met Tyr Glu Thr Lys Leu Lys Glu Leu Glu
2270                2275                2280
Thr Asp Ile Ala Lys Lys Asn Gln Ser Ile Thr Asp Leu Lys Gln
2285                2290                2295
Leu Val Lys Glu Ala Thr Glu Arg Glu Gln Lys Val Asn Lys Tyr
2300                2305                2310
Asn Glu Asp Leu Glu Gln Gln Ile Lys Ile Leu Lys His Val Pro
2315                2320                2325
Glu Gly Ala Glu Thr Glu Gln Gly Leu Lys Arg Glu Leu Gln Val
2330                2335                2340
Leu Arg Leu Ala Asn His Gln Leu Asp Lys Glu Lys Ala Glu Leu
2345                2350                2355
Ile His Gln Ile Glu Ala Asn Lys Asp Gln Ser Gly Ala Glu Ser
2360                2365                2370
Thr Ile Pro Asp Ala Asp Gln Leu Lys Glu Lys Ile Lys Asp Leu
2375                2380                2385
Glu Thr Gln Leu Lys Met Ser Asp Leu Glu Lys Gln His Leu Lys
2390                2395                2400
Glu Glu Ile Lys Lys Leu Lys Lys Glu Leu Glu Asn Phe Asp Pro
2405                2410                2415
Ser Phe Phe Glu Glu Ile Glu Asp Leu Lys Tyr Asn Tyr Lys Glu
2420                2425                2430
Glu Val Lys Lys Asn Ile Leu Leu Glu Glu Lys Val Lys Lys Leu
2435                2440                2445
Ser Glu Gln Leu Gly Val Glu Leu Thr Ser Pro Val Ala Ala Ser
2450                2455                2460
Glu Glu Phe Glu Asp Glu Glu Glu Ser Pro Val Asn Phe Pro Ile
2465                2470                2475
Tyr
```

-continued

<210> SEQ ID NO 5
<211> LENGTH: 3705
<212> TYPE: DNA
<213> ORGANISM: Artificial Sequence
<220> FEATURE:
<223> OTHER INFORMATION: Synthetic Construct; nucleic acid sequence
      containing codon optimized human CEP290 fragments spliced together
      in a single open reading frame; the nucleic acid sequences
      encoding fragments aa130-380, aa700-1040; aa1260-1605 and
      aa1695-1990.

<400> SEQUENCE: 5

```
atggagttgg aggacatgga aaaggagctc gaaaagaaa agaaagtgaa tgagcagctc      60
gccctgcgga acgaagaagc cgaaaacgaa aacagtaagc tgagaaggga aaacaaacgg    120
ctgaaaaaga gaacgagca gctctgtcag gatatcatag attaccagaa acagatcgat     180
tcacaaaaag aaactttgct ctcacgaagg ggagaagata gcgactatag atcacagctc    240
agtaagaaga actacgagct gattcagtac ttggatgaaa ttcagaccct gacagaagcc    300
aatgagaaaa tcgaagtaca gaaccaagaa atgcggaaaa acctcgagga gagcgtgcaa    360
gagatggaga agatgaccga cgaatacaac cggatgaaag ctattgtaca tcagactgac    420
aacgtcatcg atcaattgaa gaagaaaaac gaccactacc aattgcaagt tcaagagctg    480
accgatctcc tcaaatccaa aaacgaggag gacgaccccca taatggtggc cgtgaacgct    540
aaagtcgaag agtggaaact gatcctctcc tccaaggatg acgagattat cgaatatcag    600
cagatgctgc acaatctgcg cgagaagttg aagaatgcac agctcgacgc cgacaaatct    660
aatgtaatgg ccctgcagca gggaatccaa gaaagggata gtcaaatcaa aatgcttact    720
gagcaagtcg aacagtacac caaagagatg gagaaacacc ttaaggccca agtcgatcag    780
ctgacaggca gaaatgagga gcttcgccag gaactccgcg agtcccgcaa agaagcaatc    840
aactatagtc agcagctggc aaaagctaac ctcaaaatcg accatctcga aaaagaaacg    900
tccctgctca gacagtccga gggcagcaat gttgtgttca agggcataga tctcccggac    960
ggcattgccc ccagtagtgc ttccatcata aactcccaaa acgaatactt gatccatctg   1020
ctgcaagagc ttgagaacaa ggagaagaaa cttaagaatt tggaggacag cctcgaggac   1080
tacaatagga agttcgctgt catccggcac cagcagagct gttgtataa ggaatatctt   1140 agtgagaagg agacttggaa aacagagagt aaaacgataa aggaagagaa gcgcaaactg   1200
gaggaccagg ttcagcagga tgccattaag gtgaaagagt acaataacct tctgaatgcg   1260
ttgcagatgg acagcgacga gatgaagaaa atcttggctg agaattcccg gaaaatcacc   1320
gtgctccaag tcaatgagaa gtcccctcata agacagtaca ccacactcgt cgaactggaa   1380
agacagctga ggaaggagaa cgaaaaacag aaaaacgagc tgcttagcat ggaggccgaa   1440
gtatgcgaga gataggatg tctgcaaagg ttcaaagaga tggccatatt caagatcgcg   1500
gcactccaga aagtggtcga taactctgtg tctctcagcg agttggaact ggccaataag   1560
cagtacaatg agctgacagc caagtataga gatattctcc aaaaggacaa tatgttggtc   1620
cagaggactt caaatcttga gcacttggag tgtgagaaca tttcacttaa agaacaagta   1680
gagtccatca ataaggagct ggaaatcaca aagaaaaaac tgcacacaat agaacaagca   1740
tgggaacagg aaactaaact gggcaacgaa agcagcatgg ctaagcatct gcggcagact   1800
attcagagcc tgcggaggca attcagcgga gccctgcctc tcgctcagca agagaagttt   1860
tctaaaacaa tgatacagct gcaaaatgat aaactcaaaa tcatgcaaga gatgaagaac   1920
tctcagcagg agcacagaaa catggagaac aagacactgg agatgaact caagttgaaa   1980
```

|  |  |  |
|---|---|---|
| gggctggagg agttgatttc tacccttaag gatacaaaag gggcacaaaa ggtcattaac | 2040 |
| tggcatatga agatagagga actgagactg caagaactca aactgaatag agagttggtg | 2100 |
| aaggacaaag aagagatcaa gtaccttaac aatatcatct cagaatacga gcggactatc | 2160 |
| agttcactgg aggaggagat tgttcagcag aacaaattcc atgaggaaag gcagatggct | 2220 |
| tgggatcaga gagaagtgga tttggagagg cagctggaca tctttgatag acaacagaat | 2280 |
| gagatcctca acgcggcaca gaaattcgaa gaagcgacag gttcaatccc cgatccatct | 2340 |
| cttccactcc caaatcagct tgagattgct ctgagaaaga tcaaggaaaa catacggatt | 2400 |
| atccttgaga ctagagctac ttgcaagagc ctcgaagaaa aactgaagga aaggagtct | 2460 |
| gcactgcggc ttgcagagca gaatatcctg tctcgggata aggttatcaa cgaactgcgc | 2520 |
| ctgaggcttc ctgctaccgc cgagagagag aaactgattg ctgaacttgg acgaaaagaa | 2580 |
| atggaaccga atctcatca cacgctcaag attgcccacc agacaatagc caatatgcag | 2640 |
| gccaggctga atcagaaaga ggaggtgctg aagaagtatc aacgcctgct ggagaaagct | 2700 |
| agggaggagc agagagagat tgtgaaaaag cacgaagagg acctccatat cctccatcat | 2760 |
| cggttggagc ttcaggcaga ttcctccctg aacaagttta gcagacagc ctgggacgat | 2820 |
| cagtcccaga aggagtcaca gtgcttgaaa gcgaactgc aggcacagaa ggaagccaat | 2880 |
| agccgagccc ctaccacgac tatgagaaac ttggtggaac ggctcaaatc ccagctcgcc | 2940 |
| ttgaaagaga agcagcagaa agcactgtcc cgagcgttgc ttgagctgcg agctgagatg | 3000 |
| acggcagcag ccgaggagcg catcatttct gctaccagcc aaaaagaggc ccatctgaac | 3060 |
| gttcaacaga ttgttgaccg ccacaccagg gagctcaaga cccaagtaga ggaccttaat | 3120 |
| gagaacctgc tgaaattgaa agaggcactt aagacctcca gaaccgggga gaactctctg | 3180 |
| accgacaatc tgaacgatct gaacaatgag ctgcagaaga aacagaaagc ctacaataag | 3240 |
| atactgcgag aaaaagaaga aatagaccag gagaacgatg agctcaaacg gcagatcaaa | 3300 |
| aggctgacaa gcggcctgca aggcaaacct ctcaccgaca taagcagtc cctgatcgag | 3360 |
| gaactgcagc ggaaagtgaa gaaactcgaa aaccaacttg aagggaaggt ggaagaagtt | 3420 |
| gaccttaagc ccatgaaaga gaaaaacgca aggaggaac tcattagatg ggaggagggc | 3480 |
| aaaaagtggc aggccaaaat cgaagggata aggaacaaat tgaaagagaa ggaagggaa | 3540 |
| gtgtttactc tgaccaagca gctcaatact ctcaaggacc ttttttgctaa agccgacaaa | 3600 |
| gagaaactga ccctgcagag aaagctgaaa acaacaggca tgaccgtgga ccaggtgttg | 3660 |
| gggattaggg ccttggagag tgaaaaggag ctggaggagc tgaaa | 3705 |

<210> SEQ ID NO 6
<211> LENGTH: 1235
<212> TYPE: PRT
<213> ORGANISM: Artificial Sequence
<220> FEATURE:
<223> OTHER INFORMATION: Synthetic Construct; amino acid sequence
    containing codon optimized human CEP290 fragments spliced together
    in a single open reading frame: aa130-380, aa700-1040; aa1260-1605
    and aa1695-1990.

<400> SEQUENCE: 6

Met Glu Leu Glu Asp Met Glu Lys Glu Leu Glu Lys Glu Lys Lys Val
1               5                   10                  15

Asn Glu Gln Leu Ala Leu Arg Asn Glu Glu Ala Glu Asn Glu Asn Ser
            20                  25                  30

Lys Leu Arg Arg Glu Asn Lys Arg Leu Lys Lys Lys Asn Glu Gln Leu
        35                  40                  45

```
Cys Gln Asp Ile Ile Asp Tyr Gln Lys Gln Ile Asp Ser Gln Lys Glu
 50                  55                  60

Thr Leu Leu Ser Arg Arg Gly Glu Asp Ser Asp Tyr Arg Ser Gln Leu
 65                  70                  75                  80

Ser Lys Lys Asn Tyr Glu Leu Ile Gln Tyr Leu Asp Glu Ile Gln Thr
                 85                  90                  95

Leu Thr Glu Ala Asn Glu Lys Ile Glu Val Gln Asn Gln Glu Met Arg
            100                 105                 110

Lys Asn Leu Glu Glu Ser Val Gln Glu Met Glu Lys Met Thr Asp Glu
        115                 120                 125

Tyr Asn Arg Met Lys Ala Ile Val His Gln Thr Asp Asn Val Ile Asp
    130                 135                 140

Gln Leu Lys Lys Glu Asn Asp His Tyr Gln Leu Gln Val Gln Glu Leu
145                 150                 155                 160

Thr Asp Leu Leu Lys Ser Lys Asn Glu Glu Asp Asp Pro Ile Met Val
                165                 170                 175

Ala Val Asn Ala Lys Val Glu Glu Trp Lys Leu Ile Leu Ser Ser Lys
            180                 185                 190

Asp Asp Glu Ile Ile Glu Tyr Gln Gln Met Leu His Asn Leu Arg Glu
        195                 200                 205

Lys Leu Lys Asn Ala Gln Leu Asp Ala Asp Lys Ser Asn Val Met Ala
    210                 215                 220

Leu Gln Gln Gly Ile Gln Glu Arg Asp Ser Gln Ile Lys Met Leu Thr
225                 230                 235                 240

Glu Gln Val Glu Gln Tyr Thr Lys Glu Met Glu Lys His Leu Lys Ala
                245                 250                 255

Gln Val Asp Gln Leu Thr Gly Arg Asn Glu Glu Leu Arg Gln Glu Leu
            260                 265                 270

Arg Glu Ser Arg Lys Glu Ala Ile Asn Tyr Ser Gln Gln Leu Ala Lys
        275                 280                 285

Ala Asn Leu Lys Ile Asp His Leu Glu Lys Glu Thr Ser Leu Leu Arg
    290                 295                 300

Gln Ser Glu Gly Ser Asn Val Val Phe Lys Gly Ile Asp Leu Pro Asp
305                 310                 315                 320

Gly Ile Ala Pro Ser Ser Ala Ser Ile Ile Asn Ser Gln Asn Glu Tyr
                325                 330                 335

Leu Ile His Leu Leu Gln Glu Leu Glu Asn Lys Glu Lys Lys Leu Lys
            340                 345                 350

Asn Leu Glu Asp Ser Leu Glu Asp Tyr Asn Arg Lys Phe Ala Val Ile
        355                 360                 365

Arg His Gln Gln Ser Leu Leu Tyr Lys Glu Tyr Leu Ser Glu Lys Glu
    370                 375                 380

Thr Trp Lys Thr Glu Ser Lys Thr Ile Lys Glu Glu Lys Arg Lys Leu
385                 390                 395                 400

Glu Asp Gln Val Gln Gln Asp Ala Ile Lys Val Lys Glu Tyr Asn Asn
                405                 410                 415

Leu Leu Asn Ala Leu Gln Met Asp Ser Asp Glu Met Lys Lys Ile Leu
            420                 425                 430

Ala Glu Asn Ser Arg Lys Ile Thr Val Leu Gln Val Asn Glu Lys Ser
        435                 440                 445

Leu Ile Arg Gln Tyr Thr Thr Leu Val Glu Leu Glu Arg Gln Leu Arg
    450                 455                 460
```

```
Lys Glu Asn Glu Lys Gln Lys Asn Glu Leu Leu Ser Met Glu Ala Glu
465                 470                 475                 480

Val Cys Glu Lys Ile Gly Cys Leu Gln Arg Phe Lys Glu Met Ala Ile
            485                 490                 495

Phe Lys Ile Ala Ala Leu Gln Lys Val Val Asp Asn Ser Val Ser Leu
                500                 505                 510

Ser Glu Leu Glu Leu Ala Asn Lys Gln Tyr Asn Glu Leu Thr Ala Lys
        515                 520                 525

Tyr Arg Asp Ile Leu Gln Lys Asp Asn Met Leu Val Gln Arg Thr Ser
    530                 535                 540

Asn Leu Glu His Leu Glu Cys Glu Asn Ile Ser Leu Lys Glu Gln Val
545                 550                 555                 560

Glu Ser Ile Asn Lys Glu Leu Glu Ile Thr Lys Glu Lys Leu His Thr
                565                 570                 575

Ile Glu Gln Ala Trp Glu Gln Glu Thr Lys Leu Gly Asn Glu Ser Ser
                580                 585                 590

Met Ala Lys His Leu Arg Gln Thr Ile Gln Ser Leu Arg Arg Gln Phe
        595                 600                 605

Ser Gly Ala Leu Pro Leu Ala Gln Gln Glu Lys Phe Ser Lys Thr Met
    610                 615                 620

Ile Gln Leu Gln Asn Asp Lys Leu Lys Ile Met Gln Glu Met Lys Asn
625                 630                 635                 640

Ser Gln Gln Glu His Arg Asn Met Glu Asn Lys Thr Leu Glu Met Glu
                645                 650                 655

Leu Lys Leu Lys Gly Leu Glu Glu Leu Ile Ser Thr Leu Lys Asp Thr
                660                 665                 670

Lys Gly Ala Gln Lys Val Ile Asn Trp His Met Lys Ile Glu Glu Leu
        675                 680                 685

Arg Leu Gln Glu Leu Lys Leu Asn Arg Glu Leu Val Lys Asp Lys Glu
    690                 695                 700

Glu Ile Lys Tyr Leu Asn Asn Ile Ile Ser Glu Tyr Glu Arg Thr Ile
705                 710                 715                 720

Ser Ser Leu Glu Glu Glu Ile Val Gln Gln Asn Lys Phe His Glu Glu
                725                 730                 735

Arg Gln Met Ala Trp Asp Gln Arg Glu Val Asp Leu Glu Arg Gln Leu
            740                 745                 750

Asp Ile Phe Asp Arg Gln Gln Asn Glu Ile Leu Asn Ala Ala Gln Lys
    755                 760                 765

Phe Glu Glu Ala Thr Gly Ser Ile Pro Asp Pro Ser Leu Pro Leu Pro
770                 775                 780

Asn Gln Leu Glu Ile Ala Leu Arg Lys Ile Lys Glu Asn Ile Arg Ile
785                 790                 795                 800

Ile Leu Glu Thr Arg Ala Thr Cys Lys Ser Leu Glu Glu Lys Leu Lys
                805                 810                 815

Glu Lys Glu Ser Ala Leu Arg Leu Ala Glu Gln Asn Ile Leu Ser Arg
            820                 825                 830

Asp Lys Val Ile Asn Glu Leu Arg Leu Arg Leu Pro Ala Thr Ala Glu
    835                 840                 845

Arg Glu Lys Leu Ile Ala Glu Leu Gly Arg Lys Glu Met Glu Pro Lys
        850                 855                 860

Ser His His Thr Leu Lys Ile Ala His Gln Thr Ile Ala Asn Met Gln
865                 870                 875                 880

Ala Arg Leu Asn Gln Lys Glu Glu Val Leu Lys Lys Tyr Gln Arg Leu
```

```
                        885                 890                 895
Leu Glu Lys Ala Arg Glu Gln Arg Glu Ile Val Lys Lys His Glu
                900                 905                 910

Glu Asp Leu His Ile Leu His His Arg Leu Glu Leu Gln Ala Asp Ser
        915                 920                 925

Ser Leu Asn Lys Phe Lys Gln Thr Ala Trp Asp Asp Gln Ser Gln Lys
    930                 935                 940

Glu Ser Gln Cys Leu Lys Ser Glu Leu Gln Ala Gln Lys Glu Ala Asn
945                 950                 955                 960

Ser Arg Ala Pro Thr Thr Thr Met Arg Asn Leu Val Glu Arg Leu Lys
                965                 970                 975

Ser Gln Leu Ala Leu Lys Glu Lys Gln Gln Lys Ala Leu Ser Arg Ala
            980                 985                 990

Leu Leu Glu Leu Arg Ala Glu Met Thr Ala Ala Ala Glu Glu Arg Ile
            995                 1000                1005

Ile Ser Ala Thr Ser Gln Lys Glu Ala His Leu Asn Val Gln Gln
    1010                1015                1020

Ile Val Asp Arg His Thr Arg Glu Leu Lys Thr Gln Val Glu Asp
    1025                1030                1035

Leu Asn Glu Asn Leu Leu Lys Leu Lys Glu Ala Leu Lys Thr Ser
    1040                1045                1050

Lys Asn Arg Glu Asn Ser Leu Thr Asp Asn Leu Asn Asp Leu Asn
    1055                1060                1065

Asn Glu Leu Gln Lys Lys Gln Lys Ala Tyr Asn Lys Ile Leu Arg
    1070                1075                1080

Glu Lys Glu Glu Ile Asp Gln Glu Asn Asp Glu Leu Lys Arg Gln
    1085                1090                1095

Ile Lys Arg Leu Thr Ser Gly Leu Gln Gly Lys Pro Leu Thr Asp
    1100                1105                1110

Asn Lys Gln Ser Leu Ile Glu Glu Leu Gln Arg Lys Val Lys Lys
    1115                1120                1125

Leu Glu Asn Gln Leu Glu Gly Lys Val Glu Glu Val Asp Leu Lys
    1130                1135                1140

Pro Met Lys Glu Lys Asn Ala Lys Glu Glu Leu Ile Arg Trp Glu
    1145                1150                1155

Glu Gly Lys Lys Trp Gln Ala Lys Ile Glu Gly Ile Arg Asn Lys
    1160                1165                1170

Leu Lys Glu Lys Glu Gly Glu Val Phe Thr Leu Thr Lys Gln Leu
    1175                1180                1185

Asn Thr Leu Lys Asp Leu Phe Ala Lys Ala Asp Lys Glu Lys Leu
    1190                1195                1200

Thr Leu Gln Arg Lys Leu Lys Thr Thr Gly Met Thr Val Asp Gln
    1205                1210                1215

Val Leu Gly Ile Arg Ala Leu Glu Ser Glu Lys Glu Leu Glu Glu
    1220                1225                1230

Leu Lys
    1235

<210> SEQ ID NO 7
<211> LENGTH: 67
<212> TYPE: DNA
<213> ORGANISM: Homo sapiens

<400> SEQUENCE: 7
```

```
gggacaagt ttgtacaaaa aagcaggctt cgaaggagat agaaccatgc ccccaaacat    60
caattgg                                                             67

<210> SEQ ID NO 8
<211> LENGTH: 54
<212> TYPE: DNA
<213> ORGANISM: Homo sapiens

<400> SEQUENCE: 8 gggaccact ttgtacaaga aagctgggtc ctaatagatc gggaagttaa cagg          54

<210> SEQ ID NO 9
<211> LENGTH: 69
<212> TYPE: DNA
<213> ORGANISM: Homo sapiens

<400> SEQUENCE: 9 gggacaagt ttgtacaaaa aagcaggctt cgaaggagat agaaccatga cggagaacat    60
aagccaagg                                                           69

<210> SEQ ID NO 10
<211> LENGTH: 54
<212> TYPE: DNA
<213> ORGANISM: Homo sapiens

<400> SEQUENCE: 10 gggaccact ttgtacaaga aagctgggtc ctaatagatc gggaagttaa cagg          54

<210> SEQ ID NO 11
<211> LENGTH: 67
<212> TYPE: DNA
<213> ORGANISM: Homo sapiens

<400> SEQUENCE: 11 gggacaagt ttgtacaaaa aagcaggctt cgaaggagat agaaccatgc ccccaaacat    60
caattgg                                                             67

<210> SEQ ID NO 12
<211> LENGTH: 53
<212> TYPE: DNA
<213> ORGANISM: Homo sapiens

<400> SEQUENCE: 12 gggaccact ttgtacaaga aagctgggtc ctaaagattc agatcctcgg tag           53

<210> SEQ ID NO 13
<211> LENGTH: 67
<212> TYPE: DNA
<213> ORGANISM: Homo sapiens

<400> SEQUENCE: 13 gggacaagt ttgtacaaaa aagcaggctt cgaaggagat agaaccatgc ccccaaacat    60
caattgg                                                             67

<210> SEQ ID NO 14
<211> LENGTH: 55
<212> TYPE: DNA
<213> ORGANISM: Homo sapiens

<400> SEQUENCE: 14 gggaccact ttgtacaaga aagctgggtc ctaatcccctt tcttggattc cctgc        55
```

-continued

<210> SEQ ID NO 15
<211> LENGTH: 73
<212> TYPE: DNA
<213> ORGANISM: Homo sapiens

<400> SEQUENCE: 15
ggggacaagt ttgtacaaaa aagcaggctt cgaaggagat agaaccatga aaaacacttg    60
catcattgag gac                                                       73

<210> SEQ ID NO 16
<211> LENGTH: 53
<212> TYPE: DNA
<213> ORGANISM: Homo sapiens

<400> SEQUENCE: 16
ggggaccact ttgtacaaga aagctgggtc ctaaagattc agatcctcgg tag            53

<210> SEQ ID NO 17
<211> LENGTH: 67
<212> TYPE: DNA
<213> ORGANISM: Homo sapiens

<400> SEQUENCE: 17
ggggacaagt ttgtacaaaa aagcaggctt cgaaggagat agaaccatgc ccccaaacat    60
caattgg                                                              67

<210> SEQ ID NO 18
<211> LENGTH: 55
<212> TYPE: DNA
<213> ORGANISM: Homo sapiens

<400> SEQUENCE: 18
ggggaccact ttgtacaaga aagctgggtc ctaatccagc agatacttca aatcc          55

<210> SEQ ID NO 19
<211> LENGTH: 69
<212> TYPE: DNA
<213> ORGANISM: Homo sapiens

<400> SEQUENCE: 19
ggggacaagt ttgtacaaaa aagcaggctt cgaaggagat agaaccatga cggagaacat    60
aagccaagg                                                            69

<210> SEQ ID NO 20
<211> LENGTH: 55
<212> TYPE: DNA
<213> ORGANISM: Homo sapiens

<400> SEQUENCE: 20
ggggaccact ttgtacaaga aagctgggtc ctaatccagc agatacttca aatcc          55

<210> SEQ ID NO 21
<211> LENGTH: 67
<212> TYPE: DNA
<213> ORGANISM: Homo sapiens

<400> SEQUENCE: 21
ggggacaagt ttgtacaaaa aagcaggctt cgaaggagat agaaccatgc ccccaaacat    60
caattgg                                                              67

<210> SEQ ID NO 22
<211> LENGTH: 54
<212> TYPE: DNA
<213> ORGANISM: Homo sapiens

<400> SEQUENCE: 22
ggggaccact tgtacaaga aagctgggtc ctatgttttc agctttctct gcag    54

<210> SEQ ID NO 23
<211> LENGTH: 69
<212> TYPE: DNA
<213> ORGANISM: Homo sapiens

<400> SEQUENCE: 23
ggggacaagt ttgtacaaaa aagcaggctt cgaaggagat agaaccatga cggagaacat    60
aagccaagg    69

<210> SEQ ID NO 24
<211> LENGTH: 54
<212> TYPE: DNA
<213> ORGANISM: Homo sapiens

<400> SEQUENCE: 24
ggggaccact ttgtacaaga aagctgggtc ctaatagatc gggaagttaa cagg    54

<210> SEQ ID NO 25
<211> LENGTH: 69
<212> TYPE: DNA
<213> ORGANISM: Homo sapiens

<400> SEQUENCE: 25
ggggacaagt ttgtacaaaa aagcaggctt cgaaggagat agaaccatga cggagaacat    60
aagccaagg    69

<210> SEQ ID NO 26
<211> LENGTH: 54
<212> TYPE: DNA
<213> ORGANISM: Homo sapiens

<400> SEQUENCE: 26
ggggaccact ttgtacaaga aagctgggtc ctatgttttc agctttctct gcag    54

<210> SEQ ID NO 27
<211> LENGTH: 68
<212> TYPE: DNA
<213> ORGANISM: Homo sapiens

<400> SEQUENCE: 27
ggggacaagt ttgtacaaaa aagcaggctt cgaaggagat agaaccatgc agtcccagaa    60
ggagtcac    68

<210> SEQ ID NO 28
<211> LENGTH: 54
<212> TYPE: DNA
<213> ORGANISM: Homo sapiens

<400> SEQUENCE: 28
ggggaccact ttgtacaaga aagctgggtc ctatgttttc agctttctct gcag    54

<210> SEQ ID NO 29
<211> LENGTH: 67

-continued

<210> SEQ ID NO 29
<211> LENGTH: 67
<212> TYPE: DNA
<213> ORGANISM: Homo sapiens

<400> SEQUENCE: 29
ggggacaagt ttgtacaaaa aagcaggctt cgaaggagat agaaccatga caggcatgac    60
cgtggac                                                              67

<210> SEQ ID NO 30
<211> LENGTH: 54
<212> TYPE: DNA
<213> ORGANISM: Homo sapiens

<400> SEQUENCE: 30
ggggaccact ttgtacaaga aagctgggtc ctaatagatc gggaagttaa cagg           54

<210> SEQ ID NO 31
<211> LENGTH: 68
<212> TYPE: DNA
<213> ORGANISM: Homo sapiens

<400> SEQUENCE: 31
ggggacaagt ttgtacaaaa aagcaggctt cgaaggagat agaaccatgc agtcccagaa    60
ggagtcac                                                             68

<210> SEQ ID NO 32
<211> LENGTH: 57
<212> TYPE: DNA
<213> ORGANISM: Homo sapiens

<400> SEQUENCE: 32
ggggaccact ttgtacaaga aagctgggtc ctatttctct ttcatgggct taaggtc        57

<210> SEQ ID NO 33
<211> LENGTH: 68
<212> TYPE: DNA
<213> ORGANISM: Homo sapiens

<400> SEQUENCE: 33
ggggacaagt ttgtacaaaa aagcaggctt cgaaggagat agaaccatga caggcatgac    60
cgtggacc                                                             68

<210> SEQ ID NO 34
<211> LENGTH: 54
<212> TYPE: DNA
<213> ORGANISM: Homo sapiens

<400> SEQUENCE: 34
ggggaccact ttgtacaaga aagctgggtc ctaatagatc gggaagttaa cagg           54

<210> SEQ ID NO 35
<211> LENGTH: 36
<212> TYPE: PRT
<213> ORGANISM: Gallus gallus

<400> SEQUENCE: 35

Tyr Asn Lys Met Lys Leu Ile Val Gln Gln Ser Asp Ile Val Met Asp
1               5                   10                  15

Gln Leu Arg Lys Glu Asn Glu Gln Tyr Lys Phe Gln Val Gln Glu Leu
            20                  25                  30

Ser Asp Gln Leu
        35

```
<210> SEQ ID NO 36
<211> LENGTH: 36
<212> TYPE: PRT
<213> ORGANISM: Meleagris gallopavo

<400> SEQUENCE: 36

Tyr Asn Lys Met Lys Leu Ile Val Gln Gln Ser Asp Ile Val Met Asp
1               5                   10                  15

Gln Leu Arg Lys Glu Asn Glu Gln Tyr Lys Phe Gln Val Gln Glu Leu
            20                  25                  30

Ser Asp Gln Leu
        35

<210> SEQ ID NO 37
<211> LENGTH: 36
<212> TYPE: PRT
<213> ORGANISM: Rattus rattus

<400> SEQUENCE: 37

Tyr Asn Arg Met Lys Ala Ile Val His Gln Thr Asp Thr Val Met Asp
1               5                   10                  15

Gln Ile Lys Lys Glu Asn Glu His Tyr Arg Leu Gln Val Arg Glu Leu
            20                  25                  30

Thr Asp Leu Leu
        35

<210> SEQ ID NO 38
<211> LENGTH: 36
<212> TYPE: PRT
<213> ORGANISM: Mus musculus

<400> SEQUENCE: 38

Tyr Asn Arg Met Lys Ala Leu Val His Gln Ser Asp Ala Val Met Asp
1               5                   10                  15

Gln Ile Lys Lys Glu Asn Glu His Tyr Arg Leu Gln Val Arg Glu Leu
            20                  25                  30

Thr Asp Leu Leu
        35

<210> SEQ ID NO 39
<211> LENGTH: 36
<212> TYPE: PRT
<213> ORGANISM: Pongo pygmaeus

<400> SEQUENCE: 39

Tyr Asn Arg Met Lys Ala Ile Val His Gln Thr Asp Asn Val Ile Asp
1               5                   10                  15

Gln Ile Lys Lys Glu Asn Asp His Tyr Arg Leu Gln Val Gln Glu Leu
            20                  25                  30

Thr Asp Leu Leu
        35

<210> SEQ ID NO 40
<211> LENGTH: 36
<212> TYPE: PRT
<213> ORGANISM: Macaca mulatta

<400> SEQUENCE: 40

Tyr Asn Arg Met Lys Ala Ile Val His Gln Thr Asp Asn Val Ile Asp
1               5                   10                  15
```

-continued

Gln Leu Lys Lys Glu Asn Asp His Tyr Arg Leu Gln Val Gln Glu Leu
            20                  25                  30

Thr Asp Leu Leu
        35

<210> SEQ ID NO 41
<211> LENGTH: 36
<212> TYPE: PRT
<213> ORGANISM: Homo sapiens

<400> SEQUENCE: 41

Tyr Asn Arg Met Lys Ala Ile Val His Gln Thr Asp Asn Val Ile Asp
1               5                   10                  15

Gln Leu Lys Lys Glu Asn Asp His Tyr Gln Leu Gln Val Gln Glu Leu
            20                  25                  30

Thr Asp Leu Leu
        35

<210> SEQ ID NO 42
<211> LENGTH: 36
<212> TYPE: PRT
<213> ORGANISM: Felis catus

<400> SEQUENCE: 42

Tyr Asn Arg Met Lys Ala Ile Val His Gln Thr Asp Asn Ile Met Asp
1               5                   10                  15

Gln Leu Lys Lys Glu Asn Asp His Tyr Arg Leu Gln Val Gln Glu Leu
            20                  25                  30

Thr Asp Leu Leu
        35

<210> SEQ ID NO 43
<211> LENGTH: 36
<212> TYPE: PRT
<213> ORGANISM: Ailuropoda melanoleuca

<400> SEQUENCE: 43

Tyr Asn Arg Met Lys Ala Ile Val His Gln Thr Asp Asn Ile Met Asp
1               5                   10                  15

Gln Leu Lys Lys Glu Asn Asp His Tyr Arg Leu Gln Val Gln Glu Leu
            20                  25                  30

Thr Asp Leu Leu
        35

<210> SEQ ID NO 44
<211> LENGTH: 36
<212> TYPE: PRT
<213> ORGANISM: Danio tweediei

<400> SEQUENCE: 44

Tyr Asn Lys Met Lys Ile Ala Val Gln Gln Thr Asp Ala Ile Met Asp
1               5                   10                  15

Gln Leu Arg Lys Asp Arg Asp His Ala Lys Leu Gln Val Arg Glu Leu
            20                  25                  30

Thr Asp Gln Ile
        35

<210> SEQ ID NO 45
<211> LENGTH: 362
<212> TYPE: PRT

<213> ORGANISM: Homo sapiens

<400> SEQUENCE: 45

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
            85                  90                  95

Glu Leu Glu Met Ala Gln Gln Ser Ala Gly Gly Arg Asp Thr Arg Phe
        100                 105                 110

Leu Arg Asn Glu Ile Cys Gln Leu Glu Lys Gln Leu Glu Gln Lys Asp
    115                 120                 125

Arg Glu Leu Glu Asp Met Glu Lys Glu Leu Glu Lys Glu Lys Lys Val
130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
            165                 170                 175

Cys Gln Asp Ile Ile Asp Tyr Gln Lys Gln Ile Asp Ser Gln Lys Glu
        180                 185                 190

Thr Leu Leu Ser Arg Arg Gly Glu Asp Ser Asp Tyr Arg Ser Gln Leu
    195                 200                 205

Ser Lys Lys Asn Tyr Glu Leu Ile Gln Tyr Leu Asp Glu Ile Gln Thr
210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Lys Met Thr Asp Glu
            245                 250                 255

Tyr Asn Arg Met Lys Ala Ile Val His Gln Thr Asp Asn Val Ile Asp
        260                 265                 270

Gln Leu Lys Lys Glu Asn Asp His Tyr Gln Leu Gln Val Gln Glu Leu
    275                 280                 285

Thr Asp Leu Leu Lys Ser Lys Asn Glu Glu Asp Asp Pro Ile Met Val
290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
            325                 330                 335

Lys Leu Lys Asn Ala Gln Leu Asp Ala Asp Lys Ser Asn Val Met Ala
        340                 345                 350

Leu Gln Gln Gly Ile Gln Glu Arg Asp Ser
    355                 360

<210> SEQ ID NO 46
<211> LENGTH: 380
<212> TYPE: PRT
<213> ORGANISM: Homo sapiens

```
<400> SEQUENCE: 46

Met Pro Pro Asn Ile Asn Trp Lys Glu Ile Met Lys Val Asp Pro Asp
1               5                   10                  15

Asp Leu Pro Arg Gln Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Lys Glu Lys Lys Val
130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys
    370                 375                 380

<210> SEQ ID NO 47
<211> LENGTH: 580
<212> TYPE: PRT
<213> ORGANISM: Homo sapiens
```

<400> SEQUENCE: 47

```
Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Val Glu Lys Ala Gly Glu Gln
65                  70                  75                  80

Ala Lys Phe Glu Asn Gln Leu Lys Thr Lys Val Met Lys Leu Glu Asn
            85                  90                  95

Glu Leu Glu Met Ala Gln Gln Ser Ala Gly Gly Arg Asp Thr Arg Phe
                100                 105                 110

Leu Arg Asn Glu Ile Cys Gln Leu Glu Lys Gln Leu Glu Gln Lys Asp
            115                 120                 125

Arg Glu Leu Glu Asp Met Glu Lys Glu Leu Lys Glu Lys Lys Val
        130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Asn Glu Gln Leu
            165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
        210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
            245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Pro Ile Met Val
290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
            325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Cys Ile
        370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
```

```
                405                 410                 415
Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
            435                 440                 445

Lys Asp Tyr Glu Ser Gly Val Tyr Gly Leu Glu Asp Ala Val Val Glu
            450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
            485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
            515                 520                 525

Gln Gln Tyr Arg Ala Glu Asn Gln Ile Leu Leu Lys Glu Ile Glu Ser
            530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
            565                 570                 575

Leu Asn Leu Thr
            580

<210> SEQ ID NO 48
<211> LENGTH: 263
<212> TYPE: PRT
<213> ORGANISM: Homo sapiens

<400> SEQUENCE: 48

Met Ala Gln Gln Ser Ala Gly Gly Arg Asp Thr Arg Phe Leu Arg Asn
1               5                   10                  15

Glu Ile Cys Gln Leu Glu Lys Gln Leu Glu Gln Lys Asp Arg Glu Leu
            20                  25                  30

Glu Asp Met Glu Lys Glu Leu Glu Lys Glu Lys Val Asn Glu Gln
            35                  40                  45

Leu Ala Leu Arg Asn Glu Glu Ala Glu Asn Glu Asn Ser Lys Leu Arg
        50                  55                  60

Arg Glu Asn Lys Arg Leu Lys Lys Asn Glu Gln Leu Cys Gln Asp
65              70                  75                  80

Ile Ile Asp Tyr Gln Lys Gln Ile Asp Ser Gln Lys Glu Thr Leu Leu
            85                  90                  95

Ser Arg Arg Gly Glu Asp Ser Asp Tyr Arg Ser Gln Leu Ser Lys Lys
            100                 105                 110

Asn Tyr Glu Leu Ile Gln Tyr Leu Asp Glu Ile Gln Thr Leu Thr Glu
            115                 120                 125

Ala Asn Glu Lys Ile Glu Val Gln Asn Gln Glu Met Arg Lys Asn Leu
        130                 135                 140

Glu Glu Ser Val Gln Glu Met Glu Lys Met Thr Asp Glu Tyr Asn Arg
145             150                 155                 160

Met Lys Ala Ile Val His Gln Thr Asp Asn Val Ile Asp Gln Leu Lys
            165                 170                 175

Lys Glu Asn Asp His Tyr Gln Leu Gln Val Gln Glu Leu Thr Asp Leu
            180                 185                 190
```

-continued

```
Leu Lys Ser Lys Asn Glu Glu Asp Pro Ile Met Val Ala Val Asn
            195                 200                 205

Ala Lys Val Glu Glu Trp Lys Leu Ile Leu Ser Ser Lys Asp Asp Glu
210                 215                 220

Ile Ile Glu Tyr Gln Gln Met Leu His Asn Leu Arg Glu Lys Leu Lys
225                 230                 235                 240

Asn Ala Gln Leu Asp Ala Asp Lys Ser Asn Val Met Ala Leu Gln Gln
            245                 250                 255

Gly Ile Gln Glu Arg Asp Ser
            260

<210> SEQ ID NO 49
<211> LENGTH: 251
<212> TYPE: PRT
<213> ORGANISM: Homo sapiens

<400> SEQUENCE: 49

Glu Leu Glu Asp Met Glu Lys Glu Leu Glu Lys Glu Lys Lys Val Asn
1               5                   10                  15

Glu Gln Leu Ala Leu Arg Asn Glu Glu Ala Glu Asn Glu Asn Ser Lys
                20                  25                  30

Leu Arg Arg Glu Asn Lys Arg Leu Lys Lys Lys Asn Glu Gln Leu Cys
            35                  40                  45

Gln Asp Ile Ile Asp Tyr Gln Lys Gln Ile Asp Ser Gln Lys Glu Thr
50                  55                  60

Leu Leu Ser Arg Arg Gly Glu Asp Ser Asp Tyr Arg Ser Gln Leu Ser
65                  70                  75                  80

Lys Lys Asn Tyr Glu Leu Ile Gln Tyr Leu Asp Glu Ile Gln Thr Leu
                85                  90                  95

Thr Glu Ala Asn Glu Lys Ile Glu Val Gln Asn Gln Glu Met Arg Lys
            100                 105                 110

Asn Leu Glu Glu Ser Val Gln Glu Met Glu Lys Met Thr Asp Glu Tyr
            115                 120                 125

Asn Arg Met Lys Ala Ile Val His Gln Thr Asp Asn Val Ile Asp Gln
130                 135                 140

Leu Lys Lys Glu Asn Asp His Tyr Gln Leu Gln Val Gln Glu Leu Thr
145                 150                 155                 160

Asp Leu Leu Lys Ser Lys Asn Glu Glu Asp Pro Ile Met Val Ala
                165                 170                 175

Val Asn Ala Lys Val Glu Glu Trp Lys Leu Ile Leu Ser Ser Lys Asp
            180                 185                 190

Asp Glu Ile Ile Glu Tyr Gln Gln Met Leu His Asn Leu Arg Glu Lys
        195                 200                 205

Leu Lys Asn Ala Gln Leu Asp Ala Asp Lys Ser Asn Val Met Ala Leu
            210                 215                 220

Gln Gln Gly Ile Gln Glu Arg Asp Ser Gln Ile Lys Met Leu Thr Glu
225                 230                 235                 240

Gln Val Glu Gln Tyr Thr Lys Glu Met Glu Lys
                245                 250

<210> SEQ ID NO 50
<211> LENGTH: 36
<212> TYPE: PRT
<213> ORGANISM: Homo sapiens

<400> SEQUENCE: 50
```

```
Tyr Asn Arg Met Lys Ala Ile Val His Gln Thr Asp Asn Val Ile Asp
1               5                   10                  15

Gln Leu Lys Lys Glu Asn Asp His Tyr Gln Leu Gln Val Gln Glu Leu
            20                  25                  30

Thr Asp Leu Leu
        35

<210> SEQ ID NO 51
<211> LENGTH: 341
<212> TYPE: PRT
<213> ORGANISM: Homo sapiens

<400> SEQUENCE: 51

His Leu Lys Ala Gln Val Asp Gln Leu Thr Gly Arg Asn Glu Glu Leu
1               5                   10                  15

Arg Gln Glu Leu Arg Glu Ser Arg Lys Glu Ala Ile Asn Tyr Ser Gln
            20                  25                  30

Gln Leu Ala Lys Ala Asn Leu Lys Ile Asp His Leu Glu Lys Glu Thr
        35                  40                  45

Ser Leu Leu Arg Gln Ser Glu Gly Ser Asn Val Val Phe Lys Gly Ile
    50                  55                  60

Asp Leu Pro Asp Gly Ile Ala Pro Ser Ser Ala Ser Ile Ile Asn Ser
65                  70                  75                  80

Gln Asn Glu Tyr Leu Ile His Leu Leu Gln Glu Leu Asn Lys Glu
                85                  90                  95

Lys Lys Leu Lys Asn Leu Glu Asp Ser Leu Glu Asp Tyr Asn Arg Lys
            100                 105                 110

Phe Ala Val Ile Arg His Gln Gln Ser Leu Leu Tyr Lys Glu Tyr Leu
        115                 120                 125

Ser Glu Lys Glu Thr Trp Lys Thr Glu Ser Lys Thr Ile Lys Glu Glu
    130                 135                 140

Lys Arg Lys Leu Glu Asp Gln Val Gln Gln Asp Ala Ile Lys Val Lys
145                 150                 155                 160

Glu Tyr Asn Asn Leu Leu Asn Ala Leu Gln Met Asp Ser Asp Glu Met
                165                 170                 175

Lys Lys Ile Leu Ala Glu Asn Ser Arg Lys Ile Thr Val Leu Gln Val
            180                 185                 190

Asn Glu Lys Ser Leu Ile Arg Gln Tyr Thr Thr Leu Val Glu Leu Glu
        195                 200                 205

Arg Gln Leu Arg Lys Glu Asn Glu Lys Gln Lys Asn Glu Leu Leu Ser
    210                 215                 220

Met Glu Ala Glu Val Cys Glu Lys Ile Gly Cys Leu Gln Arg Phe Lys
225                 230                 235                 240

Glu Met Ala Ile Phe Lys Ile Ala Ala Leu Gln Lys Val Val Asp Asn
                245                 250                 255

Ser Val Ser Leu Ser Glu Leu Glu Leu Ala Asn Lys Gln Tyr Asn Glu
            260                 265                 270

Leu Thr Ala Lys Tyr Arg Asp Ile Leu Gln Lys Asp Asn Met Leu Val
        275                 280                 285

Gln Arg Thr Ser Asn Leu Glu His Leu Glu Cys Glu Asn Ile Ser Leu
    290                 295                 300

Lys Glu Gln Val Glu Ser Ile Asn Lys Glu Leu Glu Ile Thr Lys Glu
305                 310                 315                 320

Lys Leu His Thr Ile Glu Gln Ala Trp Glu Gln Glu Thr Lys Leu Gly
                325                 330                 335
```

Asn Glu Ser Ser Met
              340

<210> SEQ ID NO 52
<211> LENGTH: 346
<212> TYPE: PRT
<213> ORGANISM: Homo sapiens

<400> SEQUENCE: 52

Ala Lys His Leu Arg Gln Thr Ile Gln Ser Leu Arg Arg Gln Phe Ser
1               5                   10                  15

Gly Ala Leu Pro Leu Ala Gln Gln Glu Lys Phe Ser Lys Thr Met Ile
            20                  25                  30

Gln Leu Gln Asn Asp Lys Leu Lys Ile Met Gln Glu Met Lys Asn Ser
        35                  40                  45

Gln Gln Glu His Arg Asn Met Glu Asn Lys Thr Leu Glu Met Glu Leu
    50                  55                  60

Lys Leu Lys Gly Leu Glu Glu Leu Ile Ser Thr Leu Lys Asp Thr Lys
65                  70                  75                  80

Gly Ala Gln Lys Val Ile Asn Trp His Met Lys Ile Glu Glu Leu Arg
                85                  90                  95

Leu Gln Glu Leu Lys Leu Asn Arg Glu Leu Val Lys Asp Lys Glu Glu
            100                 105                 110

Ile Lys Tyr Leu Asn Asn Ile Ile Ser Glu Tyr Glu Arg Thr Ile Ser
        115                 120                 125

Ser Leu Glu Glu Glu Ile Val Gln Gln Asn Lys Phe His Glu Glu Arg
    130                 135                 140

Gln Met Ala Trp Asp Gln Arg Glu Val Asp Leu Glu Arg Gln Leu Asp
145                 150                 155                 160

Ile Phe Asp Arg Gln Gln Asn Glu Ile Leu Asn Ala Ala Gln Lys Phe
                165                 170                 175

Glu Glu Ala Thr Gly Ser Ile Pro Asp Pro Ser Leu Pro Leu Pro Asn
            180                 185                 190

Gln Leu Glu Ile Ala Leu Arg Lys Ile Lys Glu Asn Ile Arg Ile Ile
        195                 200                 205

Leu Glu Thr Arg Ala Thr Cys Lys Ser Leu Glu Lys Leu Lys Glu
    210                 215                 220

Lys Glu Ser Ala Leu Arg Leu Ala Glu Gln Asn Ile Leu Ser Arg Asp
225                 230                 235                 240

Lys Val Ile Asn Glu Leu Arg Leu Arg Leu Pro Ala Thr Ala Glu Arg
                245                 250                 255

Glu Lys Leu Ile Ala Glu Leu Gly Arg Lys Glu Met Glu Pro Lys Ser
            260                 265                 270

His His Thr Leu Lys Ile Ala His Gln Thr Ile Ala Asn Met Gln Ala
        275                 280                 285

Arg Leu Asn Gln Lys Glu Glu Val Leu Lys Lys Tyr Gln Arg Leu Leu
    290                 295                 300

Glu Lys Ala Arg Glu Glu Gln Arg Glu Ile Val Lys Lys His Glu Glu
305                 310                 315                 320

Asp Leu His Ile Leu His His Arg Leu Glu Leu Gln Ala Asp Ser Ser
                325                 330                 335

Leu Asn Lys Phe Lys Gln Thr Ala Trp Asp
            340                 345

-continued

<210> SEQ ID NO 53
<211> LENGTH: 272
<212> TYPE: PRT
<213> ORGANISM: Homo sapiens

<400> SEQUENCE: 53

Asp Gln Ser Gln Lys Glu Ser Gln Cys Leu Lys Ser Glu Leu Gln Ala
1               5                   10                  15

Gln Lys Glu Ala Asn Ser Arg Ala Pro Thr Thr Thr Met Arg Asn Leu
            20                  25                  30

Val Glu Arg Leu Lys Ser Gln Leu Ala Leu Lys Glu Lys Gln Gln Lys
        35                  40                  45

Ala Leu Ser Arg Ala Leu Leu Glu Leu Arg Ala Glu Met Thr Ala Ala
    50                  55                  60

Ala Glu Glu Arg Ile Ile Ser Ala Thr Ser Gln Lys Glu Ala His Leu
65                  70                  75                  80

Asn Val Gln Gln Ile Val Asp Arg His Thr Arg Glu Leu Lys Thr Gln
                85                  90                  95

Val Glu Asp Leu Asn Glu Asn Leu Leu Lys Leu Lys Glu Ala Leu Lys
            100                 105                 110

Thr Ser Lys Asn Arg Glu Asn Ser Leu Thr Asp Asn Leu Asn Asp Leu
        115                 120                 125

Asn Asn Glu Leu Gln Lys Lys Gln Lys Ala Tyr Asn Lys Ile Leu Arg
    130                 135                 140

Glu Lys Glu Glu Ile Asp Gln Glu Asn Asp Glu Leu Lys Arg Gln Ile
145                 150                 155                 160

Lys Arg Leu Thr Ser Gly Leu Gln Gly Lys Pro Leu Thr Asp Asn Lys
                165                 170                 175

Gln Ser Leu Ile Glu Glu Leu Gln Arg Lys Val Lys Lys Leu Glu Asn
            180                 185                 190

Gln Leu Glu Gly Lys Val Glu Val Asp Leu Lys Pro Met Lys Glu
        195                 200                 205

Lys Asn Ala Lys Glu Glu Leu Ile Arg Trp Glu Glu Gly Lys Lys Trp
    210                 215                 220

Gln Ala Lys Ile Glu Gly Ile Arg Asn Lys Leu Lys Glu Lys Glu Gly
225                 230                 235                 240

Glu Val Phe Thr Leu Thr Lys Gln Leu Asn Thr Leu Lys Asp Leu Phe
                245                 250                 255

Ala Lys Ala Asp Lys Glu Lys Leu Thr Leu Gln Arg Lys Leu Lys Thr
            260                 265                 270

<210> SEQ ID NO 54
<211> LENGTH: 296
<212> TYPE: PRT
<213> ORGANISM: Homo sapiens

<400> SEQUENCE: 54

Asp Gln Ser Gln Lys Glu Ser Gln Cys Leu Lys Ser Glu Leu Gln Ala
1               5                   10                  15

Gln Lys Glu Ala Asn Ser Arg Ala Pro Thr Thr Thr Met Arg Asn Leu
            20                  25                  30

Val Glu Arg Leu Lys Ser Gln Leu Ala Leu Lys Glu Lys Gln Gln Lys
        35                  40                  45

Ala Leu Ser Arg Ala Leu Leu Glu Leu Arg Ala Glu Met Thr Ala Ala
    50                  55                  60

Ala Glu Glu Arg Ile Ile Ser Ala Thr Ser Gln Lys Glu Ala His Leu

```
                65                  70                  75                  80
Asn Val Gln Gln Ile Val Asp Arg His Thr Arg Glu Leu Lys Thr Gln
                85                  90                  95
Val Glu Asp Leu Asn Glu Asn Leu Leu Lys Leu Lys Glu Ala Leu Lys
                100                 105                 110
Thr Ser Lys Asn Arg Glu Asn Ser Leu Thr Asp Asn Leu Asn Asp Leu
                115                 120                 125
Asn Asn Glu Leu Gln Lys Lys Gln Lys Ala Tyr Asn Lys Ile Leu Arg
                130                 135                 140
Glu Lys Glu Glu Ile Asp Gln Glu Asn Asp Glu Leu Lys Arg Gln Ile
145                 150                 155                 160
Lys Arg Leu Thr Ser Gly Leu Gln Gly Lys Pro Leu Thr Asp Asn Lys
                165                 170                 175
Gln Ser Leu Ile Glu Glu Leu Gln Arg Lys Val Lys Lys Leu Glu Asn
                180                 185                 190
Gln Leu Glu Gly Lys Val Glu Glu Val Asp Leu Lys Pro Met Lys Glu
                195                 200                 205
Lys Asn Ala Lys Glu Glu Leu Ile Arg Trp Glu Glu Gly Lys Lys Trp
                210                 215                 220
Gln Ala Lys Ile Glu Gly Ile Arg Asn Lys Leu Lys Glu Lys Glu Gly
225                 230                 235                 240
Glu Val Phe Thr Leu Thr Lys Gln Leu Asn Thr Leu Lys Asp Leu Phe
                245                 250                 255
Ala Lys Ala Asp Lys Leu Lys Leu Thr Leu Gln Arg Lys Leu Lys Thr
                260                 265                 270
Thr Gly Met Thr Val Asp Gln Val Leu Gly Ile Arg Ala Leu Glu Ser
                275                 280                 285
Glu Lys Glu Leu Glu Glu Leu Lys
                290                 295

<210> SEQ ID NO 55
<211> LENGTH: 301
<212> TYPE: PRT
<213> ORGANISM: Homo sapiens

<400> SEQUENCE: 55

Asp Gln Ser Gln Lys Glu Ser Gln Cys Leu Lys Ser Glu Leu Gln Ala
1               5                   10                  15
Gln Lys Glu Ala Asn Ser Arg Ala Pro Thr Thr Thr Met Arg Asn Leu
                20                  25                  30
Val Glu Arg Leu Lys Ser Gln Leu Ala Leu Lys Glu Lys Gln Gln Lys
                35                  40                  45
Ala Leu Ser Arg Ala Leu Leu Glu Leu Arg Ala Glu Met Thr Ala Ala
                50                  55                  60
Ala Glu Glu Arg Ile Ile Ser Ala Thr Ser Gln Lys Glu Ala His Leu
65                  70                  75                  80
Asn Val Gln Gln Ile Val Asp Arg His Thr Arg Glu Leu Lys Thr Gln
                85                  90                  95
Val Glu Asp Leu Asn Glu Asn Leu Leu Lys Leu Lys Glu Ala Leu Lys
                100                 105                 110
Thr Ser Lys Asn Arg Glu Asn Ser Leu Thr Asp Asn Leu Asn Asp Leu
                115                 120                 125
Asn Asn Glu Leu Gln Lys Lys Gln Lys Ala Tyr Asn Lys Ile Leu Arg
                130                 135                 140
```

```
Glu Lys Glu Glu Ile Asp Gln Glu Asn Asp Glu Leu Lys Arg Gln Ile
145                 150                 155                 160

Lys Arg Leu Thr Ser Gly Leu Gln Gly Lys Pro Leu Thr Asp Asn Lys
                165                 170                 175

Gln Ser Leu Ile Glu Glu Leu Gln Arg Lys Val Lys Lys Leu Glu Asn
            180                 185                 190

Gln Leu Glu Gly Lys Val Glu Val Asp Leu Lys Pro Met Lys Glu
        195                 200                 205

Lys Asn Ala Lys Glu Glu Leu Ile Arg Trp Glu Glu Gly Lys Lys Trp
210                 215                 220

Gln Ala Lys Ile Glu Gly Ile Arg Asn Lys Leu Lys Glu Lys Glu Gly
225                 230                 235                 240

Glu Val Phe Thr Leu Thr Lys Gln Leu Asn Thr Leu Lys Asp Leu Phe
            245                 250                 255

Ala Lys Ala Asp Lys Glu Lys Leu Thr Leu Gln Arg Lys Leu Lys Thr
                260                 265                 270

Thr Gly Met Thr Val Asp Gln Val Leu Gly Ile Arg Ala Leu Glu Ser
        275                 280                 285

Glu Lys Glu Leu Glu Glu Leu Lys Lys Arg Asn Leu Asp
290                 295                 300

<210> SEQ ID NO 56
<211> LENGTH: 306
<212> TYPE: PRT
<213> ORGANISM: Homo sapiens

<400> SEQUENCE: 56

Asp Gln Ser Gln Lys Glu Ser Gln Cys Leu Lys Ser Glu Leu Gln Ala
1               5                   10                  15

Gln Lys Glu Ala Asn Ser Arg Ala Pro Thr Thr Thr Met Arg Asn Leu
            20                  25                  30

Val Glu Arg Leu Lys Ser Gln Leu Ala Leu Lys Glu Lys Gln Gln Lys
        35                  40                  45

Ala Leu Ser Arg Ala Leu Leu Glu Leu Arg Ala Glu Met Thr Ala Ala
50                  55                  60

Ala Glu Glu Arg Ile Ile Ser Ala Thr Ser Gln Lys Glu Ala His Leu
65                  70                  75                  80

Asn Val Gln Gln Ile Val Asp Arg His Thr Arg Glu Leu Lys Thr Gln
                85                  90                  95

Val Glu Asp Leu Asn Glu Asn Leu Leu Lys Leu Lys Glu Ala Leu Lys
            100                 105                 110

Thr Ser Lys Asn Arg Glu Asn Ser Leu Thr Asp Asn Leu Asn Asp Leu
        115                 120                 125

Asn Asn Glu Leu Gln Lys Lys Gln Lys Ala Tyr Asn Lys Ile Leu Arg
130                 135                 140

Glu Lys Glu Glu Ile Asp Gln Glu Asn Asp Glu Leu Lys Arg Gln Ile
145                 150                 155                 160

Lys Arg Leu Thr Ser Gly Leu Gln Gly Lys Pro Leu Thr Asp Asn Lys
                165                 170                 175

Gln Ser Leu Ile Glu Glu Leu Gln Arg Lys Val Lys Lys Leu Glu Asn
            180                 185                 190

Gln Leu Glu Gly Lys Val Glu Val Asp Leu Lys Pro Met Lys Glu
        195                 200                 205

Lys Asn Ala Lys Glu Glu Leu Ile Arg Trp Glu Glu Gly Lys Lys Trp
210                 215                 220
```

Gln Ala Lys Ile Glu Gly Ile Arg Asn Lys Leu Lys Glu Lys Glu Gly
225                 230                 235                 240

Glu Val Phe Thr Leu Thr Lys Gln Leu Asn Thr Leu Lys Asp Leu Phe
                245                 250                 255

Ala Lys Ala Asp Lys Glu Lys Leu Thr Leu Gln Arg Lys Leu Lys Thr
            260                 265                 270

Thr Gly Met Thr Val Asp Gln Val Leu Gly Ile Arg Ala Leu Glu Ser
            275                 280                 285

Glu Lys Glu Leu Glu Glu Leu Lys Lys Arg Asn Leu Asp Leu Glu Asn
        290                 295                 300

Asp Ile
305

<210> SEQ ID NO 57
<211> LENGTH: 513
<212> TYPE: PRT
<213> ORGANISM: Homo sapiens

<400> SEQUENCE: 57

Thr Gly Met Thr Val Asp Gln Val Leu Gly Ile Arg Ala Leu Glu Ser
1               5                   10                  15

Glu Lys Glu Leu Glu Glu Leu Lys Lys Arg Asn Leu Asp Leu Glu Asn
            20                  25                  30

Asp Ile Leu Tyr Met Arg Ala His Gln Ala Leu Pro Arg Asp Ser Val
        35                  40                  45

Val Glu Asp Leu His Leu Gln Asn Arg Tyr Leu Gln Glu Lys Leu His
50                  55                  60

Ala Leu Glu Lys Gln Phe Ser Lys Asp Thr Tyr Ser Lys Pro Ser Ile
65                  70                  75                  80

Ser Gly Ile Glu Ser Asp Asp His Cys Gln Arg Gln Glu Leu Gln
                85                  90                  95

Lys Glu Asn Leu Lys Leu Ser Ser Glu Asn Ile Glu Leu Lys Phe Gln
            100                 105                 110

Leu Glu Gln Ala Asn Lys Asp Leu Pro Arg Leu Lys Asn Gln Val Arg
        115                 120                 125

Asp Leu Lys Glu Met Cys Glu Phe Leu Lys Lys Glu Lys Ala Glu Val
130                 135                 140

Gln Arg Lys Leu Gly His Val Arg Gly Ser Gly Arg Ser Gly Lys Thr
145                 150                 155                 160

Ile Pro Glu Leu Glu Lys Thr Ile Gly Leu Met Lys Lys Val Val Glu
                165                 170                 175

Lys Val Gln Arg Glu Asn Glu Gln Leu Lys Lys Ala Ser Gly Ile Leu
            180                 185                 190

Thr Ser Glu Lys Met Ala Asn Ile Glu Gln Glu Asn Glu Lys Leu Lys
        195                 200                 205

Ala Glu Leu Glu Lys Leu Lys Ala His Leu Gly His Gln Leu Ser Met
210                 215                 220

His Tyr Glu Ser Lys Thr Lys Gly Thr Glu Lys Ile Ile Ala Glu Asn
225                 230                 235                 240

Glu Arg Leu Arg Lys Glu Leu Lys Lys Glu Thr Asp Ala Ala Glu Lys
                245                 250                 255

Leu Arg Ile Ala Lys Asn Asn Leu Glu Ile Leu Asn Glu Lys Met Thr
            260                 265                 270

Val Gln Leu Glu Glu Thr Gly Lys Arg Leu Gln Phe Ala Glu Ser Arg

```
                275                 280                 285
Gly Pro Gln Leu Glu Gly Ala Asp Ser Lys Ser Trp Lys Ser Ile Val
        290                 295                 300
Val Thr Arg Met Tyr Glu Thr Lys Leu Lys Glu Leu Glu Thr Asp Ile
305                 310                 315                 320
Ala Lys Lys Asn Gln Ser Ile Thr Asp Leu Lys Gln Leu Val Lys Glu
                325                 330                 335
Ala Thr Glu Arg Glu Gln Lys Val Asn Lys Tyr Asn Glu Asp Leu Glu
            340                 345                 350
Gln Gln Ile Lys Ile Leu Lys His Val Pro Glu Gly Ala Glu Thr Glu
        355                 360                 365
Gln Gly Leu Lys Arg Glu Leu Gln Val Leu Arg Leu Ala Asn His Gln
    370                 375                 380
Leu Asp Lys Glu Lys Ala Glu Leu Ile His Gln Ile Glu Ala Asn Lys
385                 390                 395                 400
Asp Gln Ser Gly Ala Glu Ser Thr Ile Pro Asp Ala Asp Gln Leu Lys
                405                 410                 415
Glu Lys Ile Lys Asp Leu Glu Thr Gln Leu Lys Met Ser Asp Leu Glu
            420                 425                 430
Lys Gln His Leu Lys Glu Glu Ile Lys Leu Lys Lys Glu Leu Glu
        435                 440                 445
Asn Phe Asp Pro Ser Phe Phe Glu Glu Ile Glu Asp Leu Lys Tyr Asn
    450                 455                 460
Tyr Lys Glu Glu Val Lys Lys Asn Ile Leu Leu Glu Glu Lys Val Lys
465                 470                 475                 480
Lys Leu Ser Glu Gln Leu Gly Val Glu Leu Thr Ser Pro Val Ala Ala
                485                 490                 495
Ser Glu Glu Phe Glu Asp Glu Glu Ser Pro Val Asn Phe Pro Ile
            500                 505                 510
Tyr

<210> SEQ ID NO 58
<211> LENGTH: 480
<212> TYPE: PRT
<213> ORGANISM: Homo sapiens

<400> SEQUENCE: 58

Ile Leu Tyr Met Arg Ala His Gln Ala Leu Pro Arg Asp Ser Val Val
1               5                  10                  15
Glu Asp Leu His Leu Gln Asn Arg Tyr Leu Gln Glu Lys Leu His Ala
                20                  25                  30
Leu Glu Lys Gln Phe Ser Lys Asp Thr Tyr Ser Lys Pro Ser Ile Ser
            35                  40                  45
Gly Ile Glu Ser Asp Asp His Cys Gln Arg Glu Gln Glu Leu Gln Lys
        50                  55                  60
Glu Asn Leu Lys Leu Ser Ser Glu Asn Ile Glu Leu Lys Phe Gln Leu
65                  70                  75                  80
Glu Gln Ala Asn Lys Asp Leu Pro Arg Leu Lys Asn Gln Val Arg Asp
                85                  90                  95
Leu Lys Glu Met Cys Glu Phe Leu Lys Lys Glu Lys Ala Glu Val Gln
            100                 105                 110
Arg Lys Leu Gly His Val Arg Gly Ser Gly Arg Ser Gly Lys Thr Ile
        115                 120                 125
Pro Glu Leu Glu Lys Thr Ile Gly Leu Met Lys Lys Val Val Glu Lys
```

```
            130                 135                 140
Val Gln Arg Glu Asn Glu Gln Leu Lys Lys Ala Ser Gly Ile Leu Thr
145                 150                 155                 160

Ser Glu Lys Met Ala Asn Ile Glu Gln Glu Asn Glu Lys Leu Lys Ala
                165                 170                 175

Glu Leu Glu Lys Leu Lys Ala His Leu Gly His Gln Leu Ser Met His
            180                 185                 190

Tyr Glu Ser Lys Thr Lys Gly Thr Glu Lys Ile Ile Ala Glu Asn Glu
        195                 200                 205

Arg Leu Arg Lys Glu Leu Lys Lys Glu Thr Asp Ala Ala Glu Lys Leu
    210                 215                 220

Arg Ile Ala Lys Asn Asn Leu Glu Ile Leu Asn Glu Lys Met Thr Val
225                 230                 235                 240

Gln Leu Glu Glu Thr Gly Lys Arg Leu Gln Phe Ala Glu Ser Arg Gly
                245                 250                 255

Pro Gln Leu Glu Gly Ala Asp Ser Lys Ser Trp Lys Ser Ile Val Val
            260                 265                 270

Thr Arg Met Tyr Glu Thr Lys Leu Lys Glu Leu Glu Thr Asp Ile Ala
        275                 280                 285

Lys Lys Asn Gln Ser Ile Thr Asp Leu Lys Gln Leu Val Lys Glu Ala
    290                 295                 300

Thr Glu Arg Glu Gln Lys Val Asn Lys Tyr Asn Glu Asp Leu Glu Gln
305                 310                 315                 320

Gln Ile Lys Ile Leu Lys His Val Pro Glu Gly Ala Glu Thr Glu Gln
                325                 330                 335

Gly Leu Lys Arg Glu Leu Gln Val Leu Arg Leu Ala Asn His Gln Leu
            340                 345                 350

Asp Lys Glu Lys Ala Glu Leu Ile His Gln Ile Glu Ala Asn Lys Asp
        355                 360                 365

Gln Ser Gly Ala Glu Ser Thr Ile Pro Asp Ala Asp Gln Leu Lys Glu
    370                 375                 380

Lys Ile Lys Asp Leu Glu Thr Gln Leu Lys Met Ser Asp Leu Glu Lys
385                 390                 395                 400

Gln His Leu Lys Glu Glu Ile Lys Lys Leu Lys Glu Leu Glu Asn
                405                 410                 415

Phe Asp Pro Ser Phe Glu Glu Ile Glu Asp Leu Lys Tyr Asn Tyr
            420                 425                 430

Lys Glu Glu Val Lys Lys Asn Ile Leu Leu Glu Glu Lys Val Lys Lys
        435                 440                 445

Leu Ser Glu Gln Leu Gly Val Glu Leu Thr Ser Pro Val Ala Ala Ser
    450                 455                 460

Glu Glu Phe Glu Asp Glu Glu Ser Pro Val Asn Phe Pro Ile Tyr
465                 470                 475                 480

<210> SEQ ID NO 59
<211> LENGTH: 514
<212> TYPE: PRT
<213> ORGANISM: Homo sapiens

<400> SEQUENCE: 59

Thr Thr Gly Met Thr Val Asp Gln Val Leu Gly Ile Arg Ala Leu Glu
1               5                   10                  15

Ser Glu Lys Glu Leu Glu Glu Leu Lys Lys Arg Asn Leu Asp Leu Glu
            20                  25                  30
```

-continued

```
Asn Asp Ile Leu Tyr Met Arg Ala His Gln Ala Leu Pro Arg Asp Ser
         35                  40                  45
Val Val Glu Asp Leu His Leu Gln Asn Arg Tyr Leu Gln Glu Lys Leu
 50                  55                  60
His Ala Leu Glu Lys Gln Phe Ser Lys Asp Thr Tyr Ser Lys Pro Ser
 65                  70                  75                  80
Ile Ser Gly Ile Glu Ser Asp Asp His Cys Gln Arg Glu Gln Glu Leu
             85                  90                  95
Gln Lys Glu Asn Leu Lys Leu Ser Glu Asn Ile Glu Leu Lys Phe
                 100                 105                 110
Gln Leu Glu Gln Ala Asn Lys Asp Leu Pro Arg Leu Lys Asn Gln Val
             115                 120                 125
Arg Asp Leu Lys Glu Met Cys Glu Phe Leu Lys Lys Glu Lys Ala Glu
 130                 135                 140
Val Gln Arg Lys Leu Gly His Val Arg Gly Ser Gly Arg Ser Gly Lys
 145                 150                 155                 160
Thr Ile Pro Glu Leu Glu Lys Thr Ile Gly Leu Met Lys Lys Val Val
                 165                 170                 175
Glu Lys Val Gln Arg Glu Asn Glu Gln Leu Lys Lys Ala Ser Gly Ile
                 180                 185                 190
Leu Thr Ser Glu Lys Met Ala Asn Ile Glu Gln Glu Asn Glu Lys Leu
             195                 200                 205
Lys Ala Glu Leu Glu Lys Leu Lys Ala His Leu Gly His Gln Leu Ser
 210                 215                 220
Met His Tyr Glu Ser Lys Thr Lys Gly Thr Glu Lys Ile Ile Ala Glu
225                 230                 235                 240
Asn Glu Arg Leu Arg Lys Glu Leu Lys Lys Glu Thr Asp Ala Ala Glu
                 245                 250                 255
Lys Leu Arg Ile Ala Lys Asn Asn Leu Glu Ile Leu Asn Glu Lys Met
             260                 265                 270
Thr Val Gln Leu Glu Glu Thr Gly Lys Arg Leu Gln Phe Ala Glu Ser
             275                 280                 285
Arg Gly Pro Gln Leu Glu Gly Ala Asp Ser Lys Ser Trp Lys Ser Ile
 290                 295                 300
Val Val Thr Arg Met Tyr Glu Thr Lys Leu Lys Glu Leu Glu Thr Asp
305                 310                 315                 320
Ile Ala Lys Lys Asn Gln Ser Ile Thr Asp Leu Lys Gln Leu Val Lys
                 325                 330                 335
Glu Ala Thr Glu Arg Glu Gln Lys Val Asn Lys Tyr Asn Glu Asp Leu
             340                 345                 350
Glu Gln Gln Ile Lys Ile Leu Lys His Val Pro Glu Gly Ala Glu Thr
             355                 360                 365
Glu Gln Gly Leu Lys Arg Glu Leu Gln Val Leu Arg Leu Ala Asn His
 370                 375                 380
Gln Leu Asp Lys Glu Lys Ala Glu Leu Ile His Gln Ile Glu Ala Asn
385                 390                 395                 400
Lys Asp Gln Ser Gly Ala Glu Ser Thr Ile Pro Asp Ala Asp Gln Leu
                 405                 410                 415
Lys Glu Lys Ile Lys Asp Leu Glu Thr Gln Leu Lys Met Ser Asp Leu
             420                 425                 430
Glu Lys Gln His Leu Lys Glu Glu Ile Lys Lys Leu Lys Lys Glu Leu
             435                 440                 445
Glu Asn Phe Asp Pro Ser Phe Phe Glu Glu Ile Glu Asp Leu Lys Tyr
```

-continued

```
                450                 455                 460
Asn Tyr Lys Glu Glu Val Lys Asn Ile Leu Leu Glu Lys Val
465                 470                 475                 480

Lys Lys Leu Ser Glu Gln Leu Gly Val Glu Leu Thr Ser Pro Val Ala
                485                 490                 495

Ala Ser Glu Glu Phe Glu Asp Glu Glu Ser Pro Val Asn Phe Pro
                500                 505                 510

Ile Tyr

<210> SEQ ID NO 60
<211> LENGTH: 1900
<212> TYPE: PRT
<213> ORGANISM: Homo sapiens

<400> SEQUENCE: 60

Thr Glu Asn Ile Ser Gln Gly Asp Arg Ile Ser Glu Arg Lys Leu Asp
1               5                   10                  15

Leu Leu Ser Leu Lys Asn Met Ser Glu Ala Gln Ser Lys Asn Glu Phe
                20                  25                  30

Leu Ser Arg Glu Leu Ile Glu Lys Glu Arg Asp Leu Glu Arg Ser Arg
            35                  40                  45

Thr Val Ile Ala Lys Phe Gln Asn Lys Leu Lys Glu Leu Val Glu Glu
50                  55                  60

Asn Lys Gln Leu Glu Glu Gly Met Lys Glu Ile Leu Gln Ala Ile Lys
65                  70                  75                  80

Glu Met Gln Lys Asp Pro Asp Val Lys Gly Gly Glu Thr Ser Leu Ile
                85                  90                  95

Ile Pro Ser Leu Glu Arg Leu Val Asn Ala Ile Glu Ser Lys Asn Ala
            100                 105                 110

Glu Gly Ile Phe Asp Ala Ser Leu His Leu Lys Ala Gln Val Asp Gln
        115                 120                 125

Leu Thr Gly Arg Asn Glu Glu Leu Arg Gln Glu Leu Arg Glu Ser Arg
    130                 135                 140

Lys Glu Ala Ile Asn Tyr Ser Gln Gln Leu Ala Lys Ala Asn Leu Lys
145                 150                 155                 160

Ile Asp His Leu Glu Lys Glu Thr Ser Leu Leu Arg Gln Ser Glu Gly
                165                 170                 175

Ser Asn Val Val Phe Lys Gly Ile Asp Leu Pro Asp Gly Ile Ala Pro
            180                 185                 190

Ser Ser Ala Ser Ile Ile Asn Ser Gln Asn Glu Tyr Leu Ile His Leu
        195                 200                 205

Leu Gln Glu Leu Glu Asn Lys Glu Lys Lys Leu Lys Asn Leu Glu Asp
    210                 215                 220

Ser Leu Glu Asp Tyr Asn Arg Lys Phe Ala Val Ile Arg His Gln Gln
225                 230                 235                 240

Ser Leu Leu Tyr Lys Glu Tyr Leu Ser Glu Lys Glu Thr Trp Lys Thr
                245                 250                 255

Glu Ser Lys Thr Ile Lys Glu Glu Lys Arg Lys Leu Glu Asp Gln Val
            260                 265                 270

Gln Gln Asp Ala Ile Lys Val Lys Glu Tyr Asn Asn Leu Leu Asn Ala
        275                 280                 285

Leu Gln Met Asp Ser Asp Glu Met Lys Lys Ile Leu Ala Glu Asn Ser
    290                 295                 300

Arg Lys Ile Thr Val Leu Gln Val Asn Glu Lys Ser Leu Ile Arg Gln
```

-continued

```
            305                 310                 315                 320
        Tyr Thr Thr Leu Val Glu Leu Glu Arg Gln Leu Arg Lys Glu Asn Glu
                            325                 330                 335
        Lys Gln Lys Asn Glu Leu Leu Ser Met Glu Ala Glu Val Cys Glu Lys
                            340                 345                 350
        Ile Gly Cys Leu Gln Arg Phe Lys Glu Met Ala Ile Phe Lys Ile Ala
                            355                 360                 365
        Ala Leu Gln Lys Val Val Asp Asn Ser Val Ser Leu Ser Glu Leu Glu
                370                 375                 380
        Leu Ala Asn Lys Gln Tyr Asn Glu Leu Thr Ala Lys Tyr Arg Asp Ile
        385                 390                 395                 400
        Leu Gln Lys Asp Asn Met Leu Val Gln Arg Thr Ser Asn Leu Glu His
                            405                 410                 415
        Leu Glu Cys Glu Asn Ile Ser Leu Lys Glu Gln Val Glu Ser Ile Asn
                            420                 425                 430
        Lys Glu Leu Glu Ile Thr Lys Glu Lys Leu His Thr Ile Glu Gln Ala
                            435                 440                 445
        Trp Glu Gln Glu Thr Lys Leu Gly Asn Glu Ser Ser Met Asp Lys Ala
                            450                 455                 460
        Lys Lys Ser Ile Thr Asn Ser Asp Ile Val Ser Ile Ser Lys Lys Ile
        465                 470                 475                 480
        Thr Met Leu Glu Met Lys Glu Leu Asn Glu Arg Gln Arg Ala Glu His
                            485                 490                 495
        Cys Gln Lys Met Tyr Glu His Leu Arg Thr Ser Leu Lys Gln Met Glu
                            500                 505                 510
        Glu Arg Asn Phe Glu Leu Glu Thr Lys Phe Ala Glu Leu Thr Lys Ile
                            515                 520                 525
        Asn Leu Asp Ala Gln Lys Val Glu Gln Met Leu Arg Asp Glu Leu Ala
                            530                 535                 540
        Asp Ser Val Ser Lys Ala Val Ser Asp Ala Asp Arg Gln Arg Ile Leu
        545                 550                 555                 560
        Glu Leu Glu Lys Asn Glu Met Glu Leu Lys Val Glu Val Ser Lys Leu
                            565                 570                 575
        Arg Glu Ile Ser Asp Ile Ala Arg Arg Gln Val Glu Ile Leu Asn Ala
                            580                 585                 590
        Gln Gln Gln Ser Arg Asp Lys Glu Val Glu Ser Leu Arg Met Gln Leu
                            595                 600                 605
        Leu Asp Tyr Gln Ala Gln Ser Asp Glu Lys Ser Leu Ile Ala Lys Leu
                610                 615                 620
        His Gln His Asn Val Ser Leu Gln Leu Ser Glu Ala Thr Ala Leu Gly
        625                 630                 635                 640
        Lys Leu Glu Ser Ile Thr Ser Lys Leu Gln Lys Met Glu Ala Tyr Asn
                            645                 650                 655
        Leu Arg Leu Glu Gln Lys Leu Asp Glu Lys Glu Gln Ala Leu Tyr Tyr
                            660                 665                 670
        Ala Arg Leu Glu Gly Arg Asn Arg Ala Lys His Leu Arg Gln Thr Ile
                            675                 680                 685
        Gln Ser Leu Arg Arg Gln Phe Ser Gly Ala Leu Pro Leu Ala Gln Gln
                            690                 695                 700
        Glu Lys Phe Ser Lys Thr Met Ile Gln Leu Gln Asn Asp Lys Leu Lys
        705                 710                 715                 720
        Ile Met Gln Glu Met Lys Asn Ser Gln Gln Glu His Arg Asn Met Glu
                            725                 730                 735
```

```
Asn Lys Thr Leu Glu Met Glu Leu Lys Leu Lys Gly Leu Glu Glu Leu
                740                 745                 750

Ile Ser Thr Leu Lys Asp Thr Lys Gly Ala Gln Lys Val Ile Asn Trp
                755                 760                 765

His Met Lys Ile Glu Glu Leu Arg Leu Gln Leu Lys Leu Asn Arg
        770                 775                 780

Glu Leu Val Lys Asp Lys Glu Ile Lys Tyr Leu Asn Asn Ile Ile
785                 790                 795                 800

Ser Glu Tyr Glu Arg Thr Ile Ser Ser Leu Glu Glu Ile Val Gln
                805                 810                 815

Gln Asn Lys Phe His Glu Glu Arg Gln Met Ala Trp Asp Gln Arg Glu
                820                 825                 830

Val Asp Leu Glu Arg Gln Leu Asp Ile Phe Asp Arg Gln Gln Asn Glu
        835                 840                 845

Ile Leu Asn Ala Ala Gln Lys Phe Glu Glu Ala Thr Gly Ser Ile Pro
850                 855                 860

Asp Pro Ser Leu Pro Leu Pro Asn Gln Leu Glu Ile Ala Leu Arg Lys
865                 870                 875                 880

Ile Lys Glu Asn Ile Arg Ile Ile Leu Glu Thr Arg Ala Thr Cys Lys
                885                 890                 895

Ser Leu Glu Glu Lys Leu Lys Glu Lys Glu Ser Ala Leu Arg Leu Ala
                900                 905                 910

Glu Gln Asn Ile Leu Ser Arg Asp Lys Val Ile Asn Glu Leu Arg Leu
                915                 920                 925

Arg Leu Pro Ala Thr Ala Glu Arg Glu Lys Leu Ile Ala Glu Leu Gly
        930                 935                 940

Arg Lys Glu Met Glu Pro Lys Ser His His Thr Leu Lys Ile Ala His
945                 950                 955                 960

Gln Thr Ile Ala Asn Met Gln Ala Arg Leu Asn Gln Lys Glu Glu Val
                965                 970                 975

Leu Lys Lys Tyr Gln Arg Leu Leu Glu Lys Ala Arg Glu Glu Gln Arg
                980                 985                 990

Glu Ile Val Lys Lys His Glu Glu Asp Leu His Ile Leu His His Arg
                995                 1000                1005

Leu Glu Leu Gln Ala Asp Ser Ser Leu Asn Lys Phe Lys Gln Thr
        1010                1015                1020

Ala Trp Asp Leu Met Lys Gln Ser Pro Thr Pro Val Pro Thr Asn
        1025                1030                1035

Lys His Phe Ile Arg Leu Ala Glu Met Glu Gln Thr Val Ala Glu
        1040                1045                1050

Gln Asp Asp Ser Leu Ser Ser Leu Leu Val Lys Leu Lys Lys Val
        1055                1060                1065

Ser Gln Asp Leu Glu Arg Arg Glu Ile Thr Glu Leu Lys Val
        1070                1075                1080

Lys Glu Phe Glu Asn Ile Lys Leu Gln Leu Gln Glu Asn His Glu
        1085                1090                1095

Asp Glu Val Lys Lys Val Lys Ala Glu Val Glu Asp Leu Lys Tyr
        1100                1105                1110

Leu Leu Asp Gln Ser Gln Lys Glu Ser Gln Cys Leu Lys Ser Glu
        1115                1120                1125

Leu Gln Ala Gln Lys Glu Ala Asn Ser Arg Ala Pro Thr Thr Thr
        1130                1135                1140
```

```
Met Arg Asn Leu Val Glu Arg Leu Lys Ser Gln Leu Ala Leu Lys
    1145                1150                1155

Glu Lys Gln Gln Lys Ala Leu Ser Arg Ala Leu Leu Glu Leu Arg
    1160                1165                1170

Ala Glu Met Thr Ala Ala Ala Glu Glu Arg Ile Ile Ser Ala Thr
    1175                1180                1185

Ser Gln Lys Glu Ala His Leu Asn Val Gln Gln Ile Val Asp Arg
    1190                1195                1200

His Thr Arg Glu Leu Lys Thr Gln Val Glu Asp Leu Asn Glu Asn
    1205                1210                1215

Leu Leu Lys Leu Lys Glu Ala Leu Lys Thr Ser Lys Asn Arg Glu
    1220                1225                1230

Asn Ser Leu Thr Asp Asn Leu Asn Asp Leu Asn Asn Glu Leu Gln
    1235                1240                1245

Lys Lys Gln Lys Ala Tyr Asn Lys Ile Leu Arg Glu Lys Glu Glu
    1250                1255                1260

Ile Asp Gln Glu Asn Asp Glu Leu Lys Arg Gln Ile Lys Arg Leu
    1265                1270                1275

Thr Ser Gly Leu Gln Gly Lys Pro Leu Thr Asp Asn Lys Gln Ser
    1280                1285                1290

Leu Ile Glu Glu Leu Gln Arg Lys Val Lys Lys Leu Glu Asn Gln
    1295                1300                1305

Leu Glu Gly Lys Val Glu Glu Val Asp Leu Lys Pro Met Lys Glu
    1310                1315                1320

Lys Asn Ala Lys Glu Glu Leu Ile Arg Trp Glu Glu Gly Lys Lys
    1325                1330                1335

Trp Gln Ala Lys Ile Glu Gly Ile Arg Asn Lys Leu Lys Glu Lys
    1340                1345                1350

Glu Gly Glu Val Phe Thr Leu Thr Lys Gln Leu Asn Thr Leu Lys
    1355                1360                1365

Asp Leu Phe Ala Lys Ala Asp Lys Glu Lys Leu Thr Leu Gln Arg
    1370                1375                1380

Lys Leu Lys Thr Thr Gly Met Thr Val Asp Gln Val Leu Gly Ile
    1385                1390                1395

Arg Ala Leu Glu Ser Glu Lys Glu Leu Glu Glu Leu Lys Lys Arg
    1400                1405                1410

Asn Leu Asp Leu Glu Asn Asp Ile Leu Tyr Met Arg Ala His Gln
    1415                1420                1425

Ala Leu Pro Arg Asp Ser Val Val Glu Asp Leu His Leu Gln Asn
    1430                1435                1440

Arg Tyr Leu Gln Glu Lys Leu His Ala Leu Glu Lys Gln Phe Ser
    1445                1450                1455

Lys Asp Thr Tyr Ser Lys Pro Ser Ile Ser Gly Ile Glu Ser Asp
    1460                1465                1470

Asp His Cys Gln Arg Glu Gln Glu Leu Gln Lys Glu Asn Leu Lys
    1475                1480                1485

Leu Ser Ser Glu Asn Ile Glu Leu Lys Phe Gln Leu Glu Gln Ala
    1490                1495                1500

Asn Lys Asp Leu Pro Arg Leu Lys Asn Gln Val Arg Asp Leu Lys
    1505                1510                1515

Glu Met Cys Glu Phe Leu Lys Lys Glu Lys Ala Glu Val Gln Arg
    1520                1525                1530

Lys Leu Gly His Val Arg Gly Ser Gly Arg Ser Gly Lys Thr Ile
```

1535                1540                1545

Pro Glu Leu Glu Lys Thr Ile Gly Leu Met Lys Lys Val Val Glu
    1550                1555                1560

Lys Val Gln Arg Glu Asn Glu Gln Leu Lys Lys Ala Ser Gly Ile
    1565                1570                1575

Leu Thr Ser Glu Lys Met Ala Asn Ile Glu Gln Glu Asn Glu Lys
    1580                1585                1590

Leu Lys Ala Glu Leu Glu Lys Leu Lys Ala His Leu Gly His Gln
    1595                1600                1605

Leu Ser Met His Tyr Glu Ser Lys Thr Lys Gly Thr Glu Lys Ile
    1610                1615                1620

Ile Ala Glu Asn Glu Arg Leu Arg Lys Glu Leu Lys Lys Glu Thr
    1625                1630                1635

Asp Ala Ala Glu Lys Leu Arg Ile Ala Lys Asn Asn Leu Glu Ile
    1640                1645                1650

Leu Asn Glu Lys Met Thr Val Gln Leu Glu Glu Thr Gly Lys Arg
    1655                1660                1665

Leu Gln Phe Ala Glu Ser Arg Gly Pro Gln Leu Glu Gly Ala Asp
    1670                1675                1680

Ser Lys Ser Trp Lys Ser Ile Val Val Thr Arg Met Tyr Glu Thr
    1685                1690                1695

Lys Leu Lys Glu Leu Glu Thr Asp Ile Ala Lys Lys Asn Gln Ser
    1700                1705                1710

Ile Thr Asp Leu Lys Gln Leu Val Lys Glu Ala Thr Glu Arg Glu
    1715                1720                1725

Gln Lys Val Asn Lys Tyr Asn Glu Asp Leu Glu Gln Gln Ile Lys
    1730                1735                1740

Ile Leu Lys His Val Pro Glu Gly Ala Glu Thr Glu Gln Gly Leu
    1745                1750                1755

Lys Arg Glu Leu Gln Val Leu Arg Leu Ala Asn His Gln Leu Asp
    1760                1765                1770

Lys Glu Lys Ala Glu Leu Ile His Gln Ile Glu Ala Asn Lys Asp
    1775                1780                1785

Gln Ser Gly Ala Glu Ser Thr Ile Pro Asp Ala Asp Gln Leu Lys
    1790                1795                1800

Glu Lys Ile Lys Asp Leu Glu Thr Gln Leu Lys Met Ser Asp Leu
    1805                1810                1815

Glu Lys Gln His Leu Lys Glu Ile Lys Lys Leu Lys Lys Glu
    1820                1825                1830

Leu Glu Asn Phe Asp Pro Ser Phe Phe Glu Ile Glu Asp Leu
    1835                1840                1845

Lys Tyr Asn Tyr Lys Glu Glu Val Lys Lys Asn Ile Leu Leu Glu
    1850                1855                1860

Glu Lys Val Lys Lys Leu Ser Glu Gln Leu Gly Val Glu Leu Thr
    1865                1870                1875

Ser Pro Val Ala Ala Ser Glu Glu Phe Glu Asp Glu Glu Glu Ser
    1880                1885                1890

Pro Val Asn Phe Pro Ile Tyr
    1895                1900

<210> SEQ ID NO 61
<211> LENGTH: 201
<212> TYPE: PRT
<213> ORGANISM: Homo sapiens

<400> SEQUENCE: 61

```
Lys Asn Thr Cys Ile Ile Glu Asp Leu Lys Asn Glu Leu Gln Arg Asn
1               5                   10                  15
Lys Gly Ala Ser Thr Leu Ser Gln Gln Thr His Met Lys Ile Gln Ser
                20                  25                  30
Thr Leu Asp Ile Leu Lys Glu Lys Thr Lys Glu Ala Glu Arg Thr Ala
            35                  40                  45
Glu Leu Ala Glu Ala Asp Ala Arg Glu Lys Asp Lys Glu Leu Val Glu
        50                  55                  60
Ala Leu Lys Arg Leu Lys Asp Tyr Glu Ser Gly Val Tyr Gly Leu Glu
65                      70                  75                  80
Asp Ala Val Val Glu Ile Lys Asn Cys Lys Asn Gln Ile Lys Ile Arg
                85                  90                  95
Asp Arg Glu Ile Glu Ile Leu Thr Lys Glu Ile Asn Lys Leu Glu Leu
                100             105                 110
Lys Ile Ser Asp Phe Leu Asp Glu Asn Glu Ala Leu Arg Glu Arg Val
            115                 120                 125
Gly Leu Glu Pro Lys Thr Met Ile Asp Leu Thr Glu Phe Arg Asn Ser
        130                 135                 140
Lys His Leu Lys Gln Gln Gln Tyr Arg Ala Glu Asn Gln Ile Leu Leu
145                 150                 155                 160
Lys Glu Ile Glu Ser Leu Glu Glu Glu Arg Leu Asp Leu Lys Lys Lys
                165                 170                 175
Ile Arg Gln Met Ala Gln Glu Arg Gly Lys Arg Ser Ala Thr Ser Gly
                180                 185                 190
Leu Thr Thr Glu Asp Leu Asn Leu Thr
            195                 200
```